(12) United States Patent
Edwin et al.

(10) Patent No.: US 11,290,706 B2
(45) Date of Patent: *Mar. 29, 2022

(54) DISPLAY SYSTEMS AND METHODS FOR DETERMINING REGISTRATION BETWEEN A DISPLAY AND A USER'S EYES

(71) Applicant: Magic Leap, Inc., Plantation, FL (US)

(72) Inventors: Lionel Ernest Edwin, Plantation, FL (US); Zachary C. Nienstedt, Fort Lauderdale, FL (US); Ivan Li Chuen Yeoh, Tampa, FL (US); Samuel A. Miller, Hollywood, FL (US); Yan Xu, San Jose, CA (US); Jordan Alexander Cazamias, Menlo Park, CA (US)

(73) Assignee: Magic Leap, Inc., Plantation, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/125,932

(22) Filed: Dec. 17, 2020

(65) Prior Publication Data

US 2021/0105456 A1 Apr. 8, 2021

Related U.S. Application Data

(63) Continuation of application No. 16/251,017, filed on Jan. 17, 2019, now Pat. No. 10,917,634.

(Continued)

(51) Int. Cl.
*H04N 13/344* (2018.01)
*G02B 27/01* (2006.01)
(Continued)

(52) U.S. Cl.
CPC ....... *H04N 13/344* (2018.05); *G02B 27/0081* (2013.01); *G02B 27/0093* (2013.01);
(Continued)

(58) Field of Classification Search
CPC .... H04N 13/344; H04N 13/383; G02B 30/00; G02B 30/40; G02B 27/0081;
(Continued)

(56) References Cited

U.S. PATENT DOCUMENTS

| 5,844,656 A | * | 12/1998 | Ronzani | ............. | G02B 27/0176 |
| | | | | | 351/158 |
| 6,771,424 B1 | * | 8/2004 | Amafuji | ............. | G02B 27/0176 |
| | | | | | 345/53 |

(Continued)

FOREIGN PATENT DOCUMENTS

| WO | WO 2019/143864 | 7/2019 |
| WO | WO 2020/023542 | 1/2020 |

OTHER PUBLICATIONS

International Search Report and Written Opinion for PCT Application No. PCT/US2019/014086, dated Apr. 9, 2019.

(Continued)

*Primary Examiner* — Vijay Shankar
*Assistant Examiner* — Cory A Almeida
(74) *Attorney, Agent, or Firm* — Knobbe, Martens, Olson & Bear, LLP

(57) ABSTRACT

A wearable device may include a head-mounted display (HMD) for rendering a three-dimensional (3D) virtual object which appears to be located in an ambient environment of a user of the display. The relative positions of the HMD and one or more eyes of the user may not be in desired positions to receive, or register, image information outputted by the HMD. For example, the HMD-to-eye alignment vary for different users and may change over time (e.g., as a given user moves around or as the HMD slips or otherwise becomes displaced). The wearable device may determine a relative position or alignment between the HMD and the user's eyes. Based on the relative positions, the wearable device may determine if it is properly fitted to the user, may (Continued)

provide feedback on the quality of the fit to the user, and may take actions to reduce or minimize effects of any misalignment.

20 Claims, 45 Drawing Sheets

Related U.S. Application Data

(60) Provisional application No. 62/344,321, filed on Mar. 16, 2018, provisional application No. 62/618,559, filed on Jan. 17, 2018, provisional application No. 62/702,849, filed on Jul. 24, 2018.

(51) Int. Cl.
  *G02B 27/00* (2006.01)
  *G06F 3/04815* (2022.01)
  *H04N 13/383* (2018.01)
  *G06F 3/01* (2006.01)
  *G02B 30/40* (2020.01)

(52) U.S. Cl.
  CPC ..... *G02B 27/0172* (2013.01); *G02B 27/0176* (2013.01); *G02B 30/40* (2020.01); *G06F 3/013* (2013.01); *G06F 3/04815* (2013.01); *H04N 13/383* (2018.05); *G02B 2027/0134* (2013.01); *G02B 2027/0138* (2013.01); *G02B 2027/0174* (2013.01)

(58) Field of Classification Search
  CPC ............ G02B 27/0093; G02B 27/0172; G02B 27/0176; G02B 2027/0134; G02B 2027/0138; G02B 2027/0174; G06F 3/013; G06F 3/04815
  See application file for complete search history.

(56) References Cited

U.S. PATENT DOCUMENTS

| | | | |
|---|---|---|---|
| 6,850,221 B1 | 2/2005 | Tickle | |
| 9,081,426 B2 | 7/2015 | Armstrong | |
| 9,215,293 B2 | 12/2015 | Miller | |
| 9,348,143 B2 | 5/2016 | Gao et al. | |
| 9,417,452 B2 | 8/2016 | Schowengerdt et al. | |
| 9,470,906 B2 | 10/2016 | Kaji et al. | |
| 9,529,428 B1 | 12/2016 | Bhattacharya et al. | |
| 9,547,174 B2 | 1/2017 | Gao et al. | |
| 9,671,566 B2 | 6/2017 | Abovitz et al. | |
| 9,727,991 B2* | 8/2017 | Guenter ................. G06T 11/40 | |
| 9,740,006 B2* | 8/2017 | Gao ................... G02B 27/0025 | |
| 9,791,700 B2 | 10/2017 | Schowengerdt et al. | |
| 9,851,563 B2 | 12/2017 | Gao et al. | |
| 9,857,591 B2 | 1/2018 | Welch et al. | |
| 9,874,749 B2 | 1/2018 | Bradski | |
| 10,296,792 B2 | 5/2019 | Spizhevoy et al. | |
| 10,338,677 B2* | 7/2019 | Guenter ................. G02B 27/017 | |
| 10,521,025 B2 | 12/2019 | Powderly et al. | |
| 10,573,042 B2 | 2/2020 | Kaehler et al. | |
| 10,917,634 B2 | 2/2021 | Edwin et al. | |
| 2003/0030597 A1* | 2/2003 | Geist ................... G02B 27/0172 345/8 |
| 2003/0184868 A1* | 10/2003 | Geist ................... G02B 27/0172 359/630 |
| 2004/0174496 A1* | 9/2004 | Ji ........................... G06F 3/013 351/209 |
| 2006/0028436 A1 | 2/2006 | Armstrong | |
| 2006/0250322 A1* | 11/2006 | Hall ................... G02B 27/0172 345/8 |
| 2007/0081123 A1 | 4/2007 | Lewis | |
| 2007/0273983 A1 | 11/2007 | Herbert | |
| 2008/0002262 A1* | 1/2008 | Chirieleison ......... G02B 27/0093 359/630 |
| 2008/0106489 A1* | 5/2008 | Brown ............... G02B 27/0172 345/9 |
| 2008/0117289 A1* | 5/2008 | Schowengerdt ..... G02B 26/005 348/46 |
| 2009/0160872 A1* | 6/2009 | Gibbons .................. G02B 6/06 345/619 |
| 2009/0167673 A1 | 6/2009 | Kerofsky | |
| 2010/0283969 A1 | 11/2010 | Cooperstock et al. | |
| 2012/0068913 A1 | 3/2012 | Bar-Zeev et al. | |
| 2012/0127062 A1 | 5/2012 | Bar-Zeev et al. | |
| 2012/0139817 A1* | 6/2012 | Freeman ............ G02B 27/0101 345/8 |
| 2012/0162549 A1 | 6/2012 | Gao et al. | |
| 2012/0212484 A1 | 8/2012 | Haddick et al. | |
| 2012/0293407 A1* | 11/2012 | Lee ...................... H04N 13/344 345/156 |
| 2013/0022220 A1 | 1/2013 | Kozlowski et al. | |
| 2013/0038510 A1* | 2/2013 | Brin ..................... G02B 27/017 345/8 |
| 2013/0050833 A1 | 2/2013 | Lewis et al. | |
| 2013/0082922 A1 | 4/2013 | Miller | |
| 2013/0083003 A1 | 4/2013 | Perez et al. | |
| 2013/0117377 A1 | 5/2013 | Miller | |
| 2013/0125027 A1 | 5/2013 | Abovitz | |
| 2013/0128364 A1* | 5/2013 | Wheeler ................ A61B 3/113 359/630 |
| 2013/0208234 A1 | 8/2013 | Lewis | |
| 2013/0242262 A1 | 9/2013 | Lewis | |
| 2013/0285885 A1* | 10/2013 | Nowatzyk ............ G02B 3/0006 345/8 |
| 2013/0286053 A1* | 10/2013 | Fleck .................... G09G 3/3208 345/690 |
| 2013/0321925 A1 | 12/2013 | Jacobs et al. | |
| 2014/0002442 A1 | 1/2014 | Lamb et al. | |
| 2014/0071539 A1 | 3/2014 | Gao | |
| 2014/0146394 A1* | 5/2014 | Tout ...................... G09B 9/307 359/630 |
| 2014/0177023 A1 | 6/2014 | Gao et al. | |
| 2014/0218468 A1 | 8/2014 | Gao et al. | |
| 2014/0232988 A1 | 8/2014 | Kersting et al. | |
| 2014/0267420 A1 | 9/2014 | Schowengerdt | |
| 2014/0306866 A1 | 10/2014 | Miller et al. | |
| 2014/0354514 A1* | 12/2014 | Aronsson ................. G06F 3/013 345/7 |
| 2014/0375540 A1 | 12/2014 | Ackerman et al. | |
| 2015/0016777 A1 | 1/2015 | Abovitz et al. | |
| 2015/0035744 A1 | 2/2015 | Robbins et al. | |
| 2015/0103306 A1* | 4/2015 | Kaji ...................... G02C 5/045 351/128 |
| 2015/0178939 A1 | 6/2015 | Bradski et al. | |
| 2015/0205126 A1 | 7/2015 | Schowengerdt | |
| 2015/0220779 A1 | 8/2015 | Publicover et al. | |
| 2015/0222883 A1 | 8/2015 | Welch | |
| 2015/0222884 A1 | 8/2015 | Cheng | |
| 2015/0268415 A1 | 9/2015 | Schowengerdt et al. | |
| 2015/0287206 A1* | 10/2015 | Ebisawa .................. A61B 3/111 382/154 |
| 2015/0302652 A1* | 10/2015 | Miller ..................... G06F 3/011 345/419 |
| 2015/0309263 A2 | 10/2015 | Abovitz et al. | |
| 2015/0326570 A1 | 11/2015 | Publicover et al. | |
| 2015/0346494 A1 | 12/2015 | TeKolste et al. | |
| 2015/0346495 A1 | 12/2015 | Welch et al. | |
| 2016/0011419 A1* | 1/2016 | Gao .................... G02B 27/0172 359/471 |
| 2016/0026253 A1* | 1/2016 | Bradski .............. G02B 27/0172 345/8 |
| 2016/0055822 A1* | 2/2016 | Bell .................... G02B 27/0172 345/207 |
| 2016/0109709 A1 | 4/2016 | Osterhout | |
| 2016/0198949 A1* | 7/2016 | Spitzer ............... G02B 27/0172 351/204 |
| 2016/0209648 A1 | 7/2016 | Haddick et al. | |
| 2016/0270656 A1 | 9/2016 | Samec et al. | |
| 2017/0053165 A1 | 2/2017 | Kaehler | |
| 2017/0053166 A1 | 2/2017 | Amayeh et al. | |
| 2017/0122725 A1 | 5/2017 | Yeoh et al. | |
| 2017/0124928 A1 | 5/2017 | Edwin et al. | |

(56) References Cited

U.S. PATENT DOCUMENTS

| | | | |
|---|---|---|---|
| 2017/0160518 | A1 | 6/2017 | Lanman et al. |
| 2017/0206412 | A1 | 7/2017 | Kaehler |
| 2017/0212351 | A1 | 7/2017 | Schowengerdt et al. |
| 2017/0261610 | A1* | 9/2017 | Scally .................... G01S 13/66 |
| 2017/0285343 | A1* | 10/2017 | Belenkii ............ G02B 27/0172 |
| 2018/0004002 | A1 | 1/2018 | Rong et al. |
| 2018/0032133 | A1* | 2/2018 | Cho ........................ G06F 3/013 |
| 2018/0098056 | A1* | 4/2018 | Bohn .................. H04N 13/144 |
| 2019/0019023 | A1* | 1/2019 | Konttori .............. G06K 9/2027 |
| 2019/0137765 | A1* | 5/2019 | Chang ................ G02B 27/0176 |
| 2019/0141847 | A1* | 5/2019 | Chang ................ G02B 27/0176 |
| 2019/0222830 | A1 | 7/2019 | Edwin et al. |
| 2019/0243448 | A1* | 8/2019 | Miller .................... A61B 3/113 |
| 2020/0051320 | A1* | 2/2020 | Laffont .................. G06T 5/002 |
| 2021/0271091 | A1 | 9/2021 | Xu |

OTHER PUBLICATIONS

International Preliminary Report on Patentability for PCT Application No. PCT/US2019/014086, dated Jul. 21, 2020.

International Search Report and Written Opinion for PCT Application No. PCT/US 19/43096, dated Oct. 16, 2019.

ARToolKit: https://web.archive.org/web/20051013062315/http://www.hitl.washington.edu:80/artoolkit/documentation/hardware.htm, archived Oct. 13, 2005.

Azuma, "A Survey of Augmented Reality," Teleoperators and Virtual Environments 6, 4 (Aug. 1997), pp. 355-385. https://web.archive.org/web/20010604100006/http://www.cs.unc.edu/~azuma/ARpresence.pdf.

Azuma, "Predictive Tracking for Augmented Realty," TR95-007, Department of Computer Science, UNC-Chapel Hill, NC, Feb. 1995.

Bimber, et al., "Spatial Augmented Reality—Merging Real and Virtual Worlds," 2005 https://web.media.mit.edu/~raskar/book/BimberRaskarAugmentedRealityBook.pdf.

Jacob, "Eye Tracking in Advanced Interface Design," Human-Computer Interaction Lab Naval Research Laboratory, Washington, D.C. / paper/ in Virtual Environments and Advanced Interface Design, ed. by W. Barfield and T.A. Furness, pp. 258-288, Oxford University Press, New York (1995).

Tanriverdi and Jacob, "Interacting With Eye Movements in Virtual Environments," Department of Electrical Engineering and Computer Science, Tufts University, Medford, MA—paper/Proc. ACM CHI 2000 Human Factors in Computing Systems Conference, pp. 265-272, Addison-Wesley/ACM Press (2000).

International Preliminary Report on Patentability for PCT Application No. PCT/US 19/43096, dated Jan. 26, 2021.

* cited by examiner

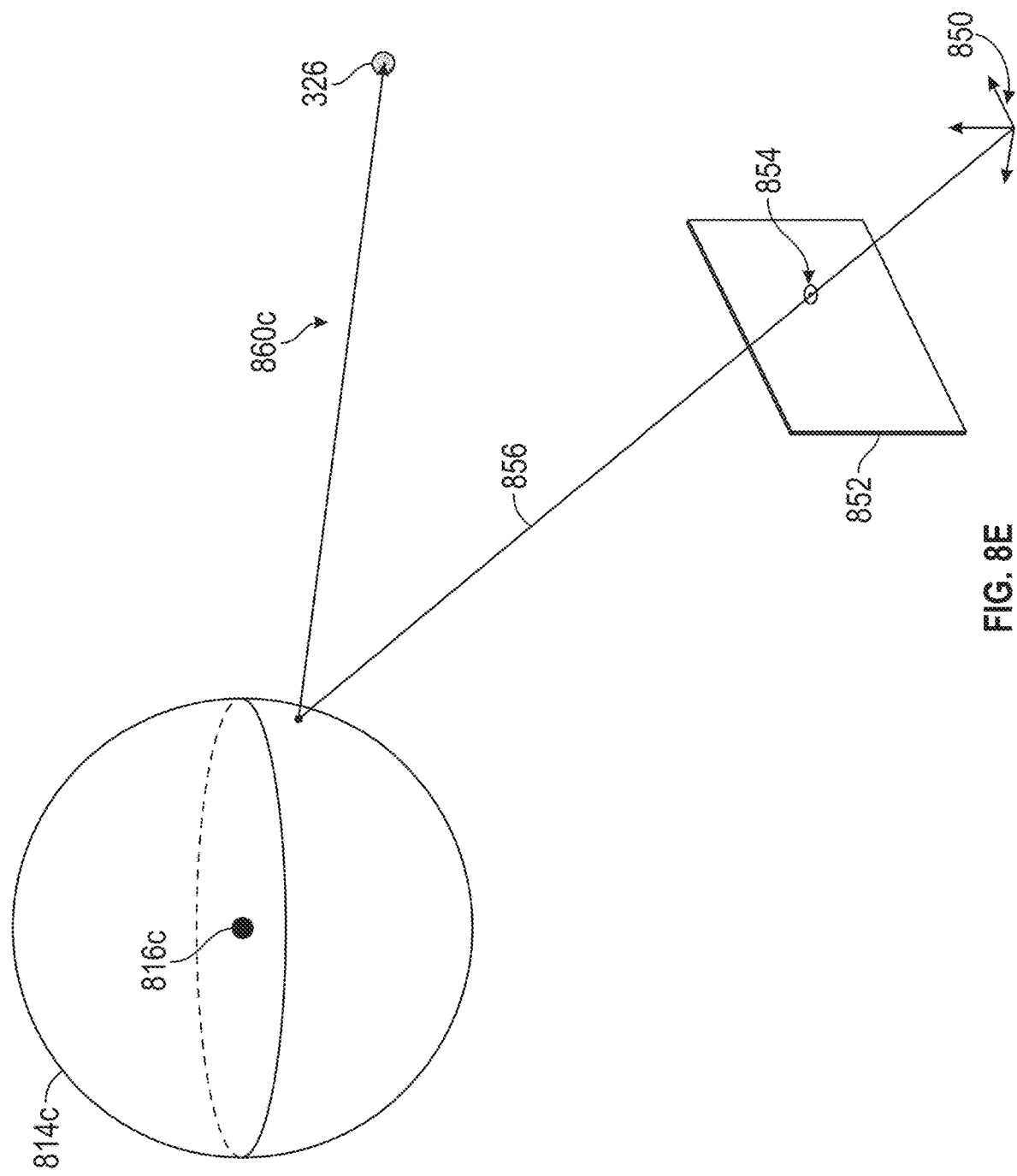

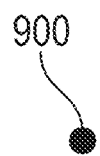
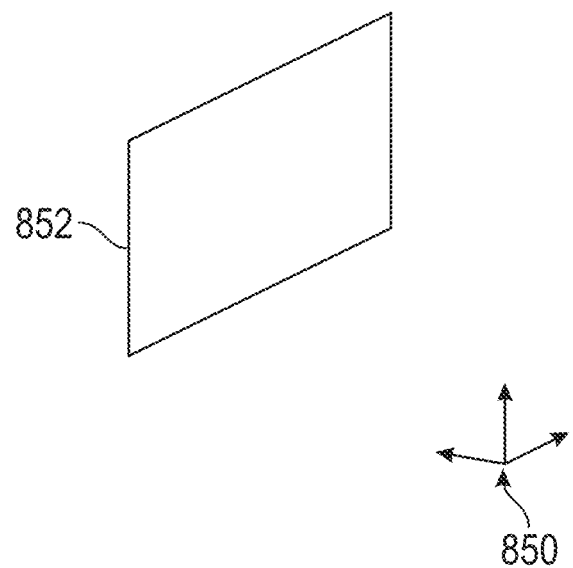
FIG. 9A

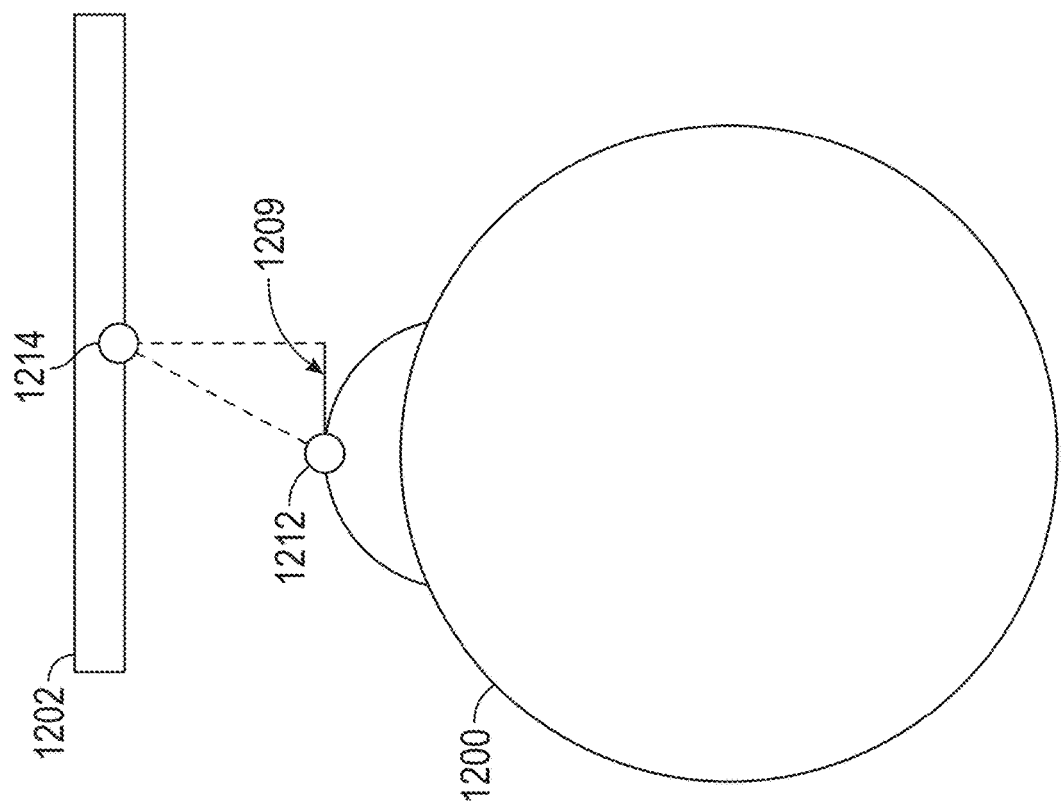
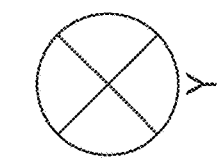
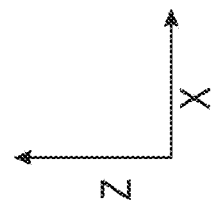
FIG. 12B

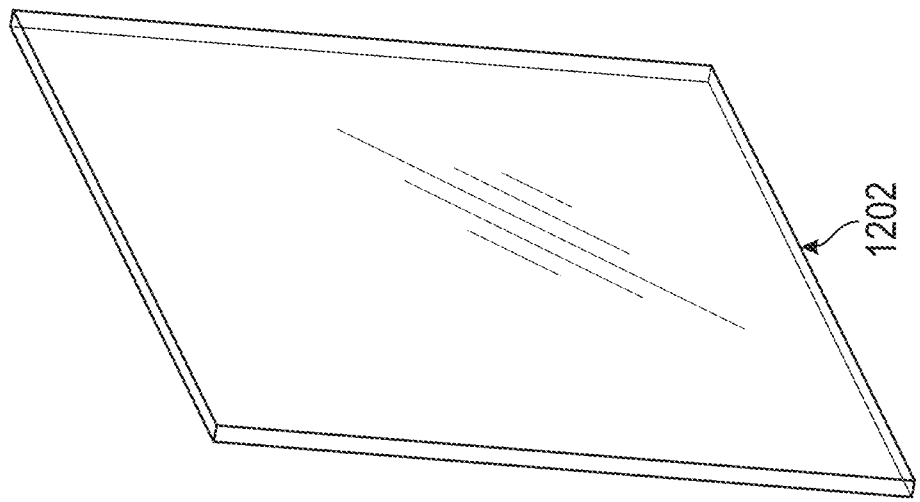
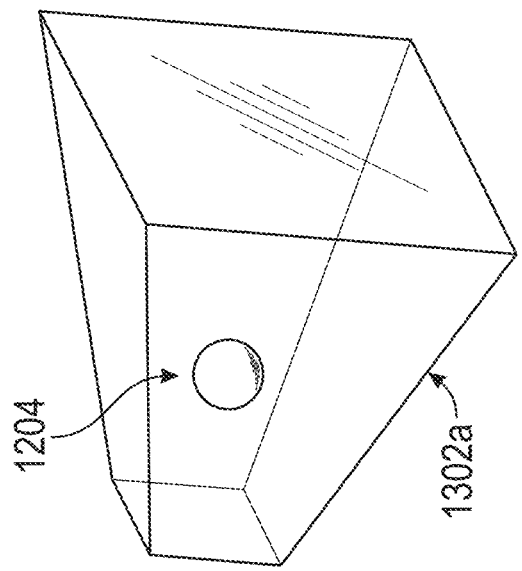
FIG. 13A

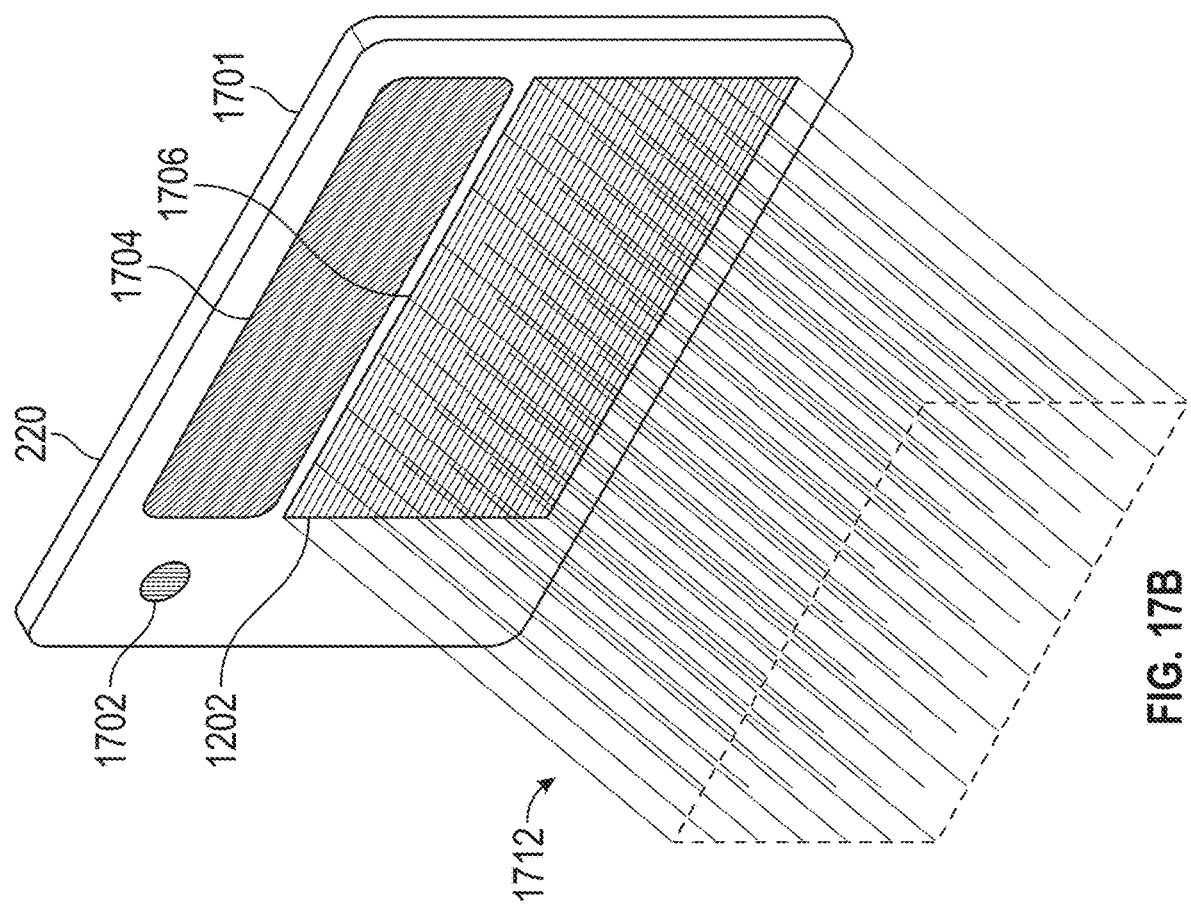

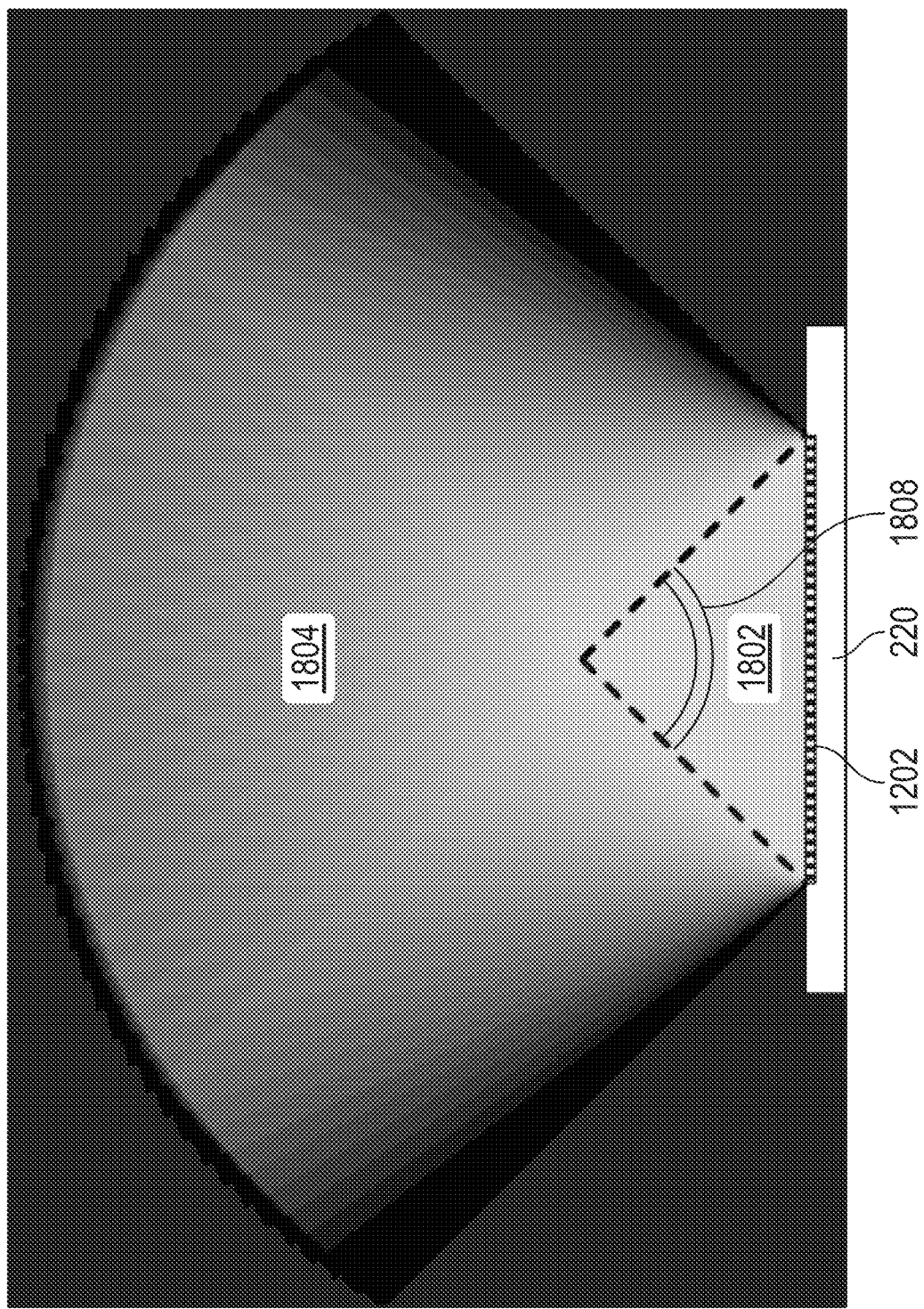

DISPLAY SYSTEMS AND METHODS FOR DETERMINING REGISTRATION BETWEEN A DISPLAY AND A USER'S EYES

PRIORITY CLAIM

This application is a continuation application of U.S. patent application Ser. No. 16/251,017, entitled "DISPLAY SYSTEMS AND METHODS FOR DETERMINING RESGISTRATION BETWEEN A DISPLAY AND A USER'S EYES" filed on Jan. 17, 2019, which claims priority to: U.S. Patent Prov. App. 62/644,321, entitled "DISPLAY SYSTEMS AND METHODS FOR DETERMINING REGISTRATION BETWEEN A DISPLAY AND A USER'S EYES" and filed on Mar. 16, 2018; U.S. Patent Prov. App. 62/618,559, entitled "EYE CENTER OF ROTATION DETERMINATION, DEPTH PLANE SELECTION, AND RENDER CAMERA POSITIONING IN DISPLAY SYSTEMS" filed on Jan. 17, 2018; and U.S. Patent Prov. App. 62/702,849, entitled "EYE CENTER OF ROTATION DETERMINATION, DEPTH PLANE SELECTION, AND RENDER CAMERA POSITIONING IN DISPLAY SYSTEMS" and filed on Jul. 24, 2018. Each of the above-recited applications is incorporated herein by reference in its entirety.

INCORPORATION BY REFERENCE

This application incorporates by reference the entirety of each of the following patent applications and publications: U.S. application Ser. No. 14/555,585 filed on Nov. 27, 2014, published on Jul. 23, 2015 as U.S. Publication No. 2015/0205126; U.S. application Ser. No. 14/690,401 filed on Apr. 18, 2015, published on Oct. 22, 2015 as U.S. Publication No. 2015/0302652; U.S. application Ser. No. 14/212,961 filed on Mar. 14, 2014, now U.S. Pat. No. 9,417,452 issued on Aug. 16, 2016; U.S. application Ser. No. 14/331,218 filed on Jul. 14, 2014, published on Oct. 29, 2015 as U.S. Publication No. 2015/0309263; U.S. Patent Publication No. 2016/0270656; U.S. Patent Publication No. 2015/0178939, published Jun. 25, 2015; U.S. Patent Publication No. 2015/0016777; U.S. patent application Ser. No. 15/274,823; U.S. patent application Ser. No. 15/296,869; U.S. patent application Ser. No. 15/717,747, filed Sep. 27, 2017; U.S. patent application Ser. No. 15/497,726, filed Apr. 26, 2017; U.S. Patent Publication No. 2017/0053165, published Feb. 23, 2017; U.S. Patent Publication No. 2017/0053166, published Feb. 23, 2017; U.S. application Ser. No. 15/341,760, filed on Nov. 2, 2016, published on May 4, 2017 as U.S. Publication No. 2017/0122725; U.S. application Ser. No. 15/341,822, filed on Nov. 2, 2016, published on May 4, 2017 as U.S. Publication No. 2017/0124928; U.S. Provisional Patent Application No. 62/618,559, filed Jan. 17, 2018; and U.S. Provisional Patent Application No. 62/642,761, filed Mar. 14, 2018.

FIELD

The present disclosure relates to display systems, including virtual reality and augmented reality display systems, and, more particularly, to systems and methods for evaluating fit of a display on a user.

BACKGROUND

Modern computing and display technologies have facilitated the development of systems for so called "virtual reality", "augmented reality", or "mixed reality" experiences, wherein digitally reproduced images or portions thereof are presented to a user in a manner wherein they seem to be, or may be perceived as, real. A virtual reality, or "VR", scenario typically involves presentation of digital or virtual image information without transparency to other actual real-world visual input; an augmented reality, or "AR", scenario typically involves presentation of digital or virtual image information as an augmentation to visualization of the actual world around the user; a mixed reality, or "MR", related to merging real and virtual worlds to produce new environments where physical and virtual objects coexist and interact in real time. As it turns out, the human visual perception system is very complex, and producing a VR, AR, or MR technology that facilitates a comfortable, natural-feeling, rich presentation of virtual image elements amongst other virtual or real-world imagery elements is challenging. Systems and methods disclosed herein address various challenges related to VR, AR and MR technology.

SUMMARY

Various examples of registration observation and response in a mixed reality system are disclosed.

In some embodiments, a display system is provided for projecting light to an eye of a user to display virtual image content. The display system comprises a frame configured to be supported on a head of the user, a head-mounted display disposed on the frame, the display configured to project light into the user's eye to display virtual image content with different amounts of wavefront divergence to present virtual image content appearing to be located at different depths at different periods of time, one or more eye-tracking cameras configured to image the user's eye, and processing electronics in communication with the display and the one or more eye-tracking cameras. The processing electronics are configured to determine a position of the eye based on images of the eye obtained with the one or more eye-tracking cameras, determine whether the position of the eye is within a display registration volume of the head-mounted display system, and provide a notification based on determining whether the position of the eye is within the display registration volume, where the notification indicates at least that the display and the eye are not properly registered.

In some other embodiments, a display system is configured to project light to an eye of a user to display virtual image content. The display system comprises a frame configured to be supported on a head of the user; a head-mounted display disposed on the frame, the display configured to project light into the user's eye to display virtual image content with different amounts of wavefront divergence to present virtual image content appearing to be located at different depths at different periods of time; one or more eye-tracking cameras configured to image the user's eye; and processing electronics in communication with the display and the one or more eye-tracking cameras. The processing electronics are configured to: determine a position of the eye based on images of the eye obtained with the one or more eye-tracking cameras; determine whether the position of the eye is more than a first threshold distance outside of a viewing volume of the head-mounted display system; and in response to a determination that the position of the eye is more than the first threshold distance outside of the viewing volume of the head-mounted display system, provide feedback to the user indicating that the display and the eye are not properly registered for output.

In some other embodiments, a display system is provided for projecting light to an eye of a user to display virtual image content. The display system comprises a frame configured to be supported on a head of the user, a head-mounted display disposed on the frame, the display configured to project light into the user's eye to display virtual image content with different amounts of wavefront divergence to present virtual image content appearing to be located at different depths at different periods of time, one or more eye-tracking cameras configured to image the user's eye, and processing electronics in communication with the display and the one or more eye-tracking cameras. The processing electronics are configured to determine whether the light projected by head-mounted display is properly registered by the eye of the user and provide feedback to the user if the head-mounted display is not properly adjusted to fit the user to register the light projected by the display system.

In yet other embodiments, a method is provided for evaluating registration of virtual image content from a head-mounted display system by a user's eye. The method comprises determining a first position of the eye, determining whether the first position of the eye is within a display registration volume of the head-mounted display system, where the display registration volume is an imaginary volume associated with proper fit of the head-mounted display system relative to the user's eye, and providing a notification based on determining whether the position of the eye is within the display registration volume, where the notification indicates at least that the display and the eye are not properly registered.

Additional examples of embodiments are enumerated below.

Example 1. A display system configured to project light to an eye of a user to display virtual image content, the display system comprising:
 a frame configured to be supported on a head of the user;
 a head-mounted display disposed on the frame, the display configured to project light into the user's eye to display virtual image content with different amounts of wavefront divergence to present virtual image content appearing to be located at different depths at different periods of time;
 one or more eye-tracking cameras configured to image the user's eye; and
 processing electronics in communication with the display and the one or more eye-tracking cameras, the processing electronics configured to:
  determine a position of the eye based on images of the eye obtained with the one or more eye-tracking cameras;
  determine whether the position of the eye is within a display registration volume of the head-mounted display system; and
  provide a notification based on determining whether the position of the eye is within the display registration volume, where the notification indicates at least that the display and the eye are not properly registered.

Example 2. The display system of Example 1, wherein the processing electronics are further configured to, upon determining that the position of the eye is outside of the display registration volume, provide feedback to the user that the head-mounted display is not properly adjusted to fit the user, wherein the feedback is the notification provided based on determining whether the position of the eyes within the display registration volume.

Example 3. The display system of Example 1, further comprising at least one interchangeable fit piece removably mounted to the frame and configured to adjust a fit of the frame.

Example 4. The display system of Example 3, wherein the interchangeable fit piece comprises an interchangeable nose bridge configured to adjust the fit of the frame between the frame and a nose bridge of the user.

Example 5. The display system of Example 3 or 4, wherein the interchangeable fit piece comprises an interchangeable forehead pad configured to adjust the fit of the frame between the frame and a forehead of the user.

Example 6. The display system of any of Examples 3 to 5, wherein the interchangeable fit piece comprises an interchangeable back pad configured to adjust the fit of the frame between the frame and a back of the head of the user.

Example 7. The display system of any of Examples 2 to 6, wherein the processing electronics is further configured such that providing the notification comprises providing feedback to the user that the head-mounted display is not properly adjusted to fit the user comprises providing a suggestion to the user to swap out a currently-installed interchangeable fit piece for another interchangeable fit piece.

Example 8. The display system of any of Examples 1 to 7, further comprising one or more light sources disposed on the frame with respect to the user's eye to illuminate the user's eye, the one or more eye-tracking cameras forming images of the eye using the light from the one or more light sources.

Example 9. The display system of Example 8, wherein the one or more light sources comprises at least two light sources disposed on the frame with respect to the user's eye to illuminate the user's eye.

Example 10. The display system of any of Examples 8 to 9, wherein the one or more light sources comprises infrared light emitters.

Example 11. The display system of any of Examples 8 to 10, wherein one or more light sources form one or more glints on the eye and the processing electronics is configured to determine a location of the cornea based on the one or more glints.

Example 12. The display system of any of Examples 1 to 11, wherein the position of the eye it is a location of a center of rotation of the eye.

Example 13. The display system of any of Examples 1 to 11, wherein the cornea has associated therewith a cornea sphere having a center of curvature and the processing electronics is configured to determine a location of the center of curvature of the cornea sphere.

Example 14. The display system of Example 1, wherein the processing electronics is configured to provide the notification by providing instructions causing the display to boost a brightness of a plurality of pixels of the display relative to other pixels of the display, wherein the plurality of pixels with a boosted brightness comprise pixels expected to undergo perceived dimming under improper registration.

Example 15. A display system configured to project light to an eye of a user to display virtual image content, the display system comprising:
 a frame configured to be supported on a head of the user;
 a head-mounted display disposed on the frame, the display configured to project light into the user's eye to display virtual image content with different amounts of wavefront divergence to present virtual image content appearing to be located at different depths at different periods of time;

one or more eye-tracking cameras configured to image the user's eye; and processing electronics in communication with the display and the one or more eye-tracking cameras, the processing electronics configured to:

determine a position of the eye based on images of the eye obtained with the one or more eye-tracking cameras;

determine whether the position of the eye is more than a first threshold distance outside of a viewing volume of the head-mounted display system; and in response to a determination that the position of the eye is more than the first threshold distance outside of the viewing volume of the head-mounted display system, provide feedback to the user indicating that the display and the eye are not properly registered for output.

Example 16. The display system of Example 15, wherein the processing electronics are configured to determine whether the position of the eye is more than the first threshold distance outside of a viewing volume by at least:

determining whether the position of the eye is less than a second threshold distance from the eyepiece; and in response to a determination that the position of the eye is less than the second threshold distance from the head-mounted display system, providing feedback to the user indicating that the display and the eye are not properly registered for output.

Example 17. The display system of Example 15, wherein the processing electronics are configured to determine whether the position of the eye is more than the first threshold distance outside of a viewing volume by at least:

determining whether the position of the eye is more than a second threshold distance from the eyepiece; and in response to a determination that the position of the eye is more than the second threshold distance from the head-mounted display system, providing feedback to the user indicating that the display and the eye are not properly registered for output.

Example 18. The display system of Example 15, wherein the processing electronics are configured to determine whether the position of the eye is more than the first threshold distance outside of a viewing volume by at least:

determining whether the position of the eye is more than a second threshold distance outside of a subspace of a field of view of the eye tracking camera; and in response to a determination that the position of the eye is more than the second threshold distance outside of the subspace of the viewing volume of the eye tracking camera, providing feedback to the user indicating that the display and the eye are not properly registered for output.

Example 19. The display system of Example 15 wherein the viewing volume of the head-mounted display is a volume through which light representing every pixel of virtual image content presented by the head-mounted display is expected to pass.

Example 20. A display system configured to project light to an eye of a user to display virtual image content, the display system comprising:

a frame configured to be supported on a head of the user;

a head-mounted display disposed on the frame, the display configured to project light into the user's eye to display virtual image content with different amounts of wavefront divergence to present virtual image content appearing to be located at different depths at different periods of time;

one or more eye-tracking cameras configured to image the user's eye; and processing electronics in communication with the display and the one or more eye-tracking cameras, the processing electronics configured to:

determine whether the light projected by head-mounted display is properly registered by the eye of the user; and provide feedback to the user if the head-mounted display is not properly adjusted to fit the user to register the light projected by the display system.

Example 21. The display system of Example 20, further comprising at least one interchangeable fit piece removably mounted to the frame and configured to adjust a fit of the frame.

Example 22. The display system of Example 21, wherein the interchangeable fit piece comprises an interchangeable nose bridge configured to adjust the fit of the frame between the frame and a nose bridge of the user.

Example 23. The display system of Example 20 or 22, wherein the interchangeable fit piece comprises an interchangeable forehead pad configured to adjust the fit of the frame between the frame and a forehead of the user.

Example 24. The display system of any of Examples 20 to 23, wherein the interchangeable fit piece comprises an interchangeable back pad configured to adjust the fit of the frame between the frame and a back of the head of the user.

Example 25. The display system of any of Examples 20 to 24, wherein the processing electronics is further configured such that providing feedback to the user that the head-mounted display is not properly adjusted to fit the user comprises providing a suggestion to the user to swap out a currently-installed interchangeable fit piece for another interchangeable fit piece.

Example 26. A method for evaluating registration of virtual image content from a head-mounted display system by a user's eye, the method comprising:

determining a first position of the eye;

determining whether the first position of the eye is within a display registration volume of the head-mounted display system, wherein the display registration volume is an imaginary volume associated with proper fit of the head-mounted display system relative to the user's eye; and providing a notification based on determining whether the position of the eye is within the display registration volume, where the notification indicates at least that the display and the eye are not properly registered.

Example 27. The method of Example 26, wherein the head-mounted display system comprises an eye-tracking camera, wherein determining the first position of the eye comprises utilizing the eye-tracking camera to image the eye of the user.

Example 28. The method of Example 27, wherein the first position of the eye is a position of the center of rotation of the eye, and further comprising calculating a center of rotation of the eye based upon imaging of the eye by the eye-tracking camera.

Example 29. The method of Example 26, wherein the head-mounted display system is configured to project light into the eye to display virtual image content in the field of view of the user, and further comprising displaying an indication that the wearable system is properly fitted.

Example 30. The method of any of Examples 26 to 29, further comprising automatically tracking the center of rotation of the eye over time with the head-mounted display system and notify the user when the center of rotation of the eye moves outside of the registration display volume.

Example 31. The method of Examples 26 or 29, further comprising:
   determining a second position of the eye;
   determining that the second position of the eye is within the display registration volume; and
   in response to determining that the second position of the eye is within the display registration volume, providing additional feedback to the user indicating that the wearable system is properly fitted to the user.

Example 32. The method of any of Examples 26 to 31, wherein, when the eye of the user is not within the display registration volume, at least some pixels of the head-mounted display system are dimmed or invisible to the user.

Example 33. The method of any of Examples 26 to 32, further comprising changing a field of view of the head-mounted display system when the position of the eye is outside the display registration volume,
   wherein the head-mounted display system comprises at least one display having a first field of field when the position of the eye is inside the display registration volume, wherein the display has a second field of view when the position of the eye is outside the display registration volume, and wherein the second field of view is smaller than the first field of view.

Example 34. The method of Example 33, wherein providing the notification comprises providing feedback to the user within the second field of view.

Example 35. The method of any of Examples 26 to 34, wherein the wearable system comprises at least one interchangeable fit piece, and further comprising:
   providing a notification to the user indicating that the wearable system is not properly fitted to the user,
   wherein the notification comprises a suggestion or an instruction to the user to replace a currently-installed interchangeable fit piece with an alternative interchangeable fit piece.

Example 36. The method of Example 35, wherein the interchangeable fit piece comprises at least one fit piece selected from the group consisting of: a nose bridge pad, a forehead pad, and a back pad that goes between the wearable system and a back of a user's head.

Example 37. The method of Example 36, wherein the wearable system comprises at least one interchangeable nose bridge pad, further comprising determining that a display of the head-mounted system is too low with respect to the eye, and wherein providing the notification to the user comprises prompting the user to install a larger nose bridge pad.

Example 38. The method of any of Examples 26 to 37, further comprising:
   identifying a plurality of pixels of a display of the head-mounted display system that the user is expected to perceive as dimmed as a result of the first position of the eye being outside the display registration volume; and
   boosting brightness of the plurality of pixels of the display relative to other pixels in the display to mitigate the expected dimming.

Example 39. A display system configured to project light to an eye of a user to display virtual image content, the display system comprising:
   a frame configured to be supported on a head of the user;
   a head-mounted display disposed on the frame, the display configured to project light into the user's eye to display virtual image content as rendered by a virtual render camera with different amounts of wavefront divergence to present virtual image content appearing to be located at different depths at different periods of time;
   one or more eye-tracking cameras configured to image the user's eye; and
   processing electronics in communication with the display and the one or more eye-tracking cameras, the processing electronics configured to:
      determine a distance away from the display at which the eye is located based on images of the eye obtained with the one or more eye-tracking cameras, and
      adjust a focal length of the virtual render camera based on the determined distance.

Example 40. A display system configured to project light to an eye of a user to display virtual image content, the display system comprising:
   a frame configured to be supported on a head of the user;
   a head-mounted display disposed on the frame, the display configured to project light into the user's eye to display virtual image content with different amounts of wavefront divergence to present virtual image content appearing to be located at different depths at different periods of time;
   one or more eye-tracking cameras configured to image the user's eye; and
   processing electronics in communication with the display and the one or more eye-tracking cameras, the processing electronics configured to:
      determine a position of the eye relative to the display based on images of the eye obtained with the one or more eye-tracking cameras;
      determine an amount of pixels of virtual image content that the user is expected to perceive as dimmed based on the position of the eye relative to the display; and
      control operation of the display based on the determined amount of pixels.

Example 41. The display system of Example 40, wherein the processing electronics are configured to determine an amount of pixels of virtual image content that the user is not expected to perceive as dimmed based on the position of the eye relative to the display.

Example 42. The display system of Examples 40 or 41, wherein the processing electronics are configured to control operation of the display by:
   boosting a brightness of the pixels of virtual image content that the user is expected to perceive as dimmed based on the position of the eye relative to the display.

Example 43. The display system of any of the Examples 40-42, wherein the amount of pixels of virtual image content comprises a percentage of pixels.

Example 44. The display system of any of the Examples 40-43, wherein the processing electronics are configured to compare the amount of pixels of virtual image content with one or more thresholds and, in response to a determination that the amount of pixels of virtual image content exceeds one or more thresholds, provide feedback to the user indicating that the display and the eye are not properly registered for output.

Example 45. A display system configured to project light to an eye of a user to display virtual image content, the display system comprising:
   a frame configured to be supported on a head of the user;
   a head-mounted display disposed on the frame, the display configured to project light into the user's eye to display virtual image content with different amounts of wavefront divergence to present virtual image content appearing to be located at different depths at different periods of time;

one or more eye-tracking cameras configured to image the user's eye; and processing electronics in communication with the display and the one or more eye-tracking cameras, the processing electronics configured to:

define a registration volume relative to the display based on one or more parameters;

determine a position of the eye based on images of the eye obtained with the one or more eye-tracking cameras;

determine whether the position of the eye is within the registration volume of the head-mounted display system; and control operation of the display based on determining whether the position of the eye is within the display registration volume.

Example 46. The display system of Example 45, wherein the one or more parameters comprise a type of application that is running on the display system.

Example 47. The display system of any of Examples 45-46, wherein the one or more parameters comprise one or more physical parameters of the head-mounted display.

Example 48. The display system of any of Examples 45-47, wherein the one or more physical parameters of the head-mounted display comprise one or more of a display field of view, a display surface size, a shape of the display, an outer housing of the display, an amount of optical power imparted by the display to light representing virtual image content.

Example 49. The display system of any of Examples 45-48, wherein the processing electronics are configured to control operation of the display by presenting virtual image content to the user indicating at least that the display and the eye are not properly registered.

Example 50. The display system of Example 15, wherein the processing electronics are configured to determine whether the position of the eye is more than the first threshold distance outside of the viewing volume by at least:

determining whether the position of the eye is more than a second threshold distance outside of a subspace of the viewing volume of an outer housing of the head-mounted display; and in response to a determination that the position of the eye is more than the second threshold distance outside of the subspace of the viewing volume of the outer housing of the head-mounted display, providing feedback to the user indicating that the display and the eye are not properly registered for output.

Example 52. The display system of Example 15, wherein the processing electronics are further configured to:

identify an application running on the display system; and determine the first threshold distance based on the identified application.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

FIGS. 8C-8E illustrate example stages of locating a user's corneal center with an eye tracking module in a wearable system.

FIGS. 9A-9C illustrate an example normalization of the coordinate system of eye tracking images.

FIGS. 12A and 12B illustrate a nominal position of a display element relative to a user's eye and illustrate a coordinate system for describing the positions of the display element and the user's eye relative to one another.

FIGS. 13A and 13B illustrate nominal positioning and positioning tolerances of a display element relative to a user's eye in a head-mounted display system.

FIGS. 17A-17H illustrate views of light fields projected by a display and how the intersections of the light fields may partly define a display registration volume.

FIG. 18 illustrates a top-down view of light fields projected by a display and how the intersections of the light fields may partly define a display registration volume.

Figure 1:
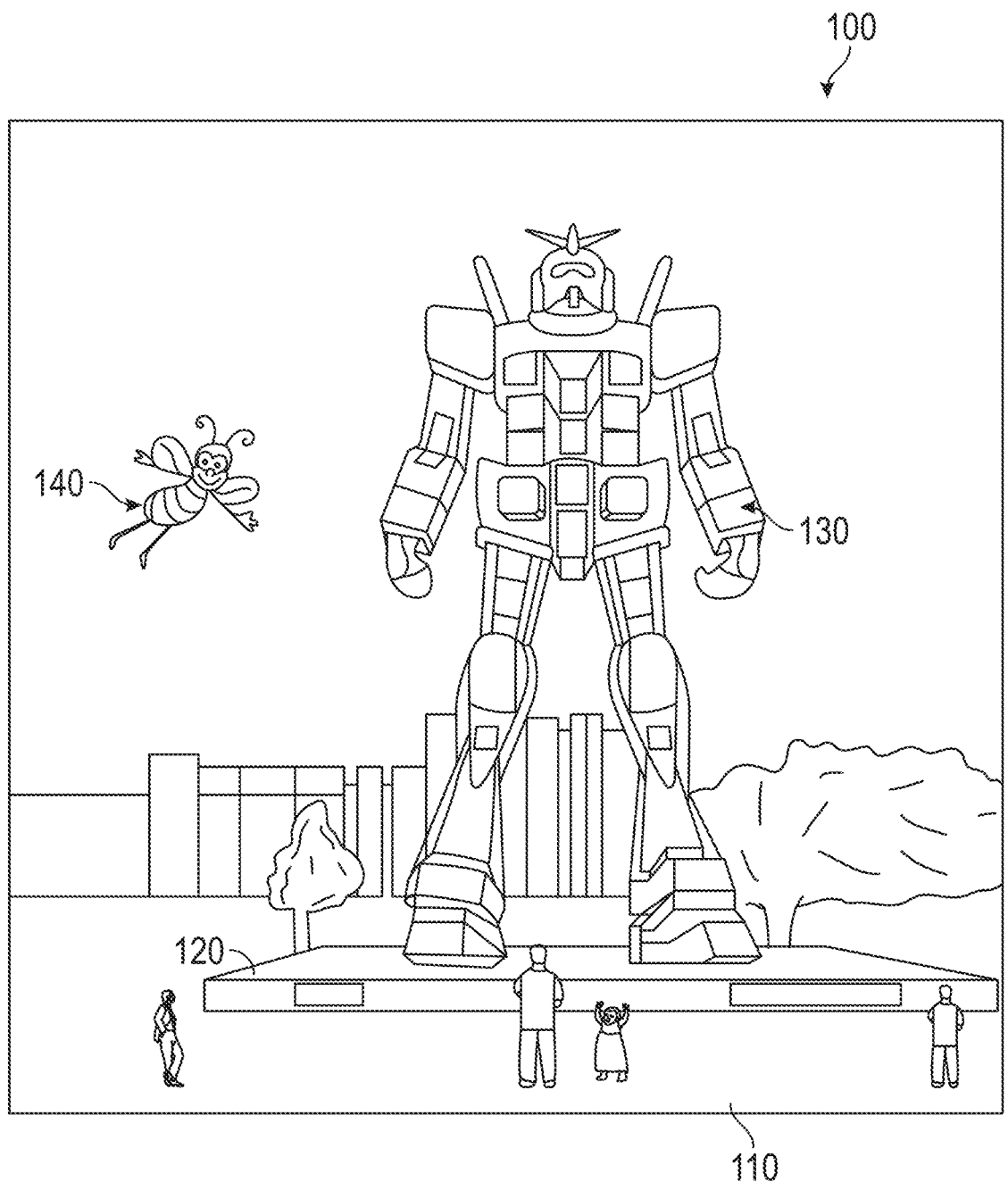
FIG. 1 depicts an illustration of a mixed reality scenario with certain virtual reality objects, and certain physical objects viewed by a person.

Throughout the drawings, reference numbers may be re-used to indicate correspondence between referenced elements. The drawings are provided to illustrate example embodiments described herein and are not intended to limit the scope of the disclosure.

DETAILED DESCRIPTION

The display portion of a display system may include a head-mounted display (HMD) which may display a three-dimensional (3D) virtual object such that the object appears to be located within the user's ambient environment. As a result, the 3D virtual object may be perceived by the user in a similar manner as real world objects.

The HMD may display images by outputting spatially modulated light to the user, with the light corresponding to the virtual object. The spatially modulated light may contain image information may be referred to as image light. To be perceived by the user, the image light travels from the HMD to an eye of the user, propagates through the pupil, and impinges on the eye's retina. It will be appreciated that if all or a portion of the image light for an image does not enter the pupil of the eye and/or does not impinge on the eye's retina, then the viewer would not see the image or the quality of the image may be degraded. As used herein, registration relates to the relative positioning of the display and the user's eyes. For example, a display may be said to be properly registered when the user's eyes and the display are positioned relative to one another for a desired amount of image light to enter the eye. A registration observer (e.g., a computer program) in the display device may be programmed to monitor whether the display is properly registered or positioned for the eye to receive the image light from the display.

In order to properly display content to users, e.g., by having the user's eyes positioned to receive image light, the user's eyes may need to be situated within a particular region or volume of space relative to the HMD. This volume may be referred to as the display registration volume. If the user's eyes are outside the display registration volume, display quality may be degraded (e.g., there may be dimming and/or displayed content that does not reach the users eyes). Various factors may combine to determine the positions of the user's eyes relative to the HMD and thus whether the user's eyes are situated within the desired display registration volume. As an example, anatomical variations between users may mean that the head-mounted display fits some users in a manner that places their eyes outside the display registration volume. As another example, the HMD may not be rigidly affixed to a user's head and may shift on the user's head over time, particularly when the user is moving around. As particular examples, the HMD may slip down the user's nose or tilt relative to a line (the interocular axis) between the user's eyes and, as a result, the HMD may not be able to provide desired virtual content (e.g., without some undesirable degradation) due to the shift of the display relative to the user's eyes.

Various systems and techniques described herein are at least in part directed to solving problems related to proper registration of a display to allow the viewer to view image content as desired. In some embodiments, a head-mounted display system may be configured to determine the position of an eye of the user. The display system may then determine whether the position of that eye is within a display registration volume of the head-mounted display system. Determining the position of the eye may include determining the position of a representative pointer volume associated with the eye e.g., the center of rotation of the eye. Determining whether the position of the eye is within the display registration volume may include determining whether the center of rotation of the eye is within the display registration volume. As discussed herein, the center of rotation of the eye may be determined using an inward-facing imaging system configured to image the eye. In addition, in some embodiments, the display registration volume is an imaginary volume associated with proper fit of the head-mounted display system relative to the user's eye. For example, the display registration volume may be a volume defined by a projection from the surface of the head-mounted display system outputting image light. More specifically, the display registration volume may be a three-dimensional geometric shape that tapers from a base towards an apex. The shape of the display registration volume's base may be defined at least in part by the geometry of the display, and the depth of the display registration volume (i.e., the distance from base to apex on the z-axis) may be at least in part defined by the field of view (FOV) of the display. For example, a round or circular display (e.g., the shape of the area on a surface from which image light is outputted to the viewer) may yield a conical display registration volume, and a polygonal display may yield a pyramidal display registration volume. As an additional example, a display with a larger FOV may yield a display registration volume having a smaller depth than a display with a smaller FOV. In some embodiments, the display registration volume may have the general shape of a truncated cone or pyramid. For example, the display registration volume may have the general shape of a frustum, e.g., a frustum of a pyramid such as a rectangular pyramid.

In some embodiments, an inward-facing imaging system of the head-mounted display system may acquire images of the user's face, including their eyes. The inward-facing imaging system may be an eye-tracking system, which may be mounted on a frame of the head-mounted display. The head-mounted display system may analyze the images to determine the relative position of the user's eyes and the HMD, and whether the position of each of the user's eyes falls within the display registration volume for that eye. Based on this information, the head-mounted display system may notify the user to adjust the fit of the HMD. For example, the notification may inform the user that the device has slipped and needs adjustment or a suggestion to make an adjustment of the HMD. In at least some embodiments, the head-mounted display system may take steps to mitigate any display degradation caused by misalignment of the HMD to the user, such as by boosting brightness or light output to the user in areas that would otherwise be dimmed by misalignment or by moving virtual content. Accordingly, such embodiments of the HMD may assist users with properly fitting the HMD and mitigating issues caused by improper fit of the HMD, such as when the HMD slips, moves, or tilts relative to the user's head. In some embodiments, it will be appreciated that the display system may be configured to notify the user of misalignment and to also take steps to mitigate display degradation caused by the misalignment. In some other embodiments, the display system may not provide a notification to the user; rather, the notification may simply be instructions or flags within the display system which trigger the display system to conduct actions to mitigate image degradation caused by misalignment.

Advantageously, the analysis of registration may be performed automatically utilizing images acquired from the inward-facing imaging system and information regarding the display registration volume stored or accessible by the display system. As a result, the fit of the HMD may be corrected upon first using the HMD, and optionally also during the course of continued usage of the HMD to ensure a high level of image quality in the use of the head-mounted display system.

Accordingly, a variety of implementations of systems and methods for observing registration of a head-mounted display system and taking action in response to the observed registration are provided herein.

Examples of 3D Display of a Wearable System

Reference will now be made to the drawings, in which like reference numerals refer to like parts throughout. Unless indicated otherwise, the drawings are schematic and not necessarily drawn to scale.

A wearable system (also referred to herein as a head-mounted display system or as an augmented reality (AR) system) may be configured to present 2D or 3D virtual images to a user. The images may be still images, frames of a video, or a video, in combination or the like. At least a portion of the wearable system may be implemented on a wearable device that may present a VR, AR, or MR environment, alone or in combination, for user interaction. The wearable device may be used interchangeably as an AR device (ARD). Further, for the purpose of the present disclosure, the term "AR" is used interchangeably with the term "MR".

FIG. 1 depicts an illustration of a mixed reality scenario with certain virtual reality objects, and certain physical objects viewed by a person. In FIG. 1, an MR scene 100 is depicted wherein a user of an MR technology sees a real-world park-like setting 110 featuring people, trees, buildings in the background, and a concrete platform 120. In addition to these items, the user of the MR technology also perceives that he "sees" a robot statue 130 standing upon the real-world platform 120, and a cartoon-like avatar character 140 flying by which seems to be a personification of a bumble bee, even though these elements do not exist in the real world.

In order for the 3D display to produce a true sensation of depth, and more specifically, a simulated sensation of surface depth, it may be desirable for each point in the display's visual field to generate an accommodative response corresponding to its virtual depth. If the accommodative response to a display point does not correspond to the virtual depth of that point, as determined by the binocular depth cues of convergence and stereopsis, the human eye may experience an accommodation conflict, resulting in unstable imaging, harmful eye strain, headaches, and, in the absence of accommodation information, almost a complete lack of surface depth.

VR, AR, and MR experiences may be provided by display systems having displays in which images corresponding to a plurality of depth planes are provided to a viewer. The images may be different for each depth plane (e.g., provide slightly different presentations of a scene or object) and may be separately focused by the viewer's eyes, thereby helping to provide the user with depth cues based on the accommodation of the eye required to bring into focus different image features for the scene located on different depth plane or based on observing different image features on different depth planes being out of focus. As discussed elsewhere herein, such depth cues provide credible perceptions of depth.

Figure 2:
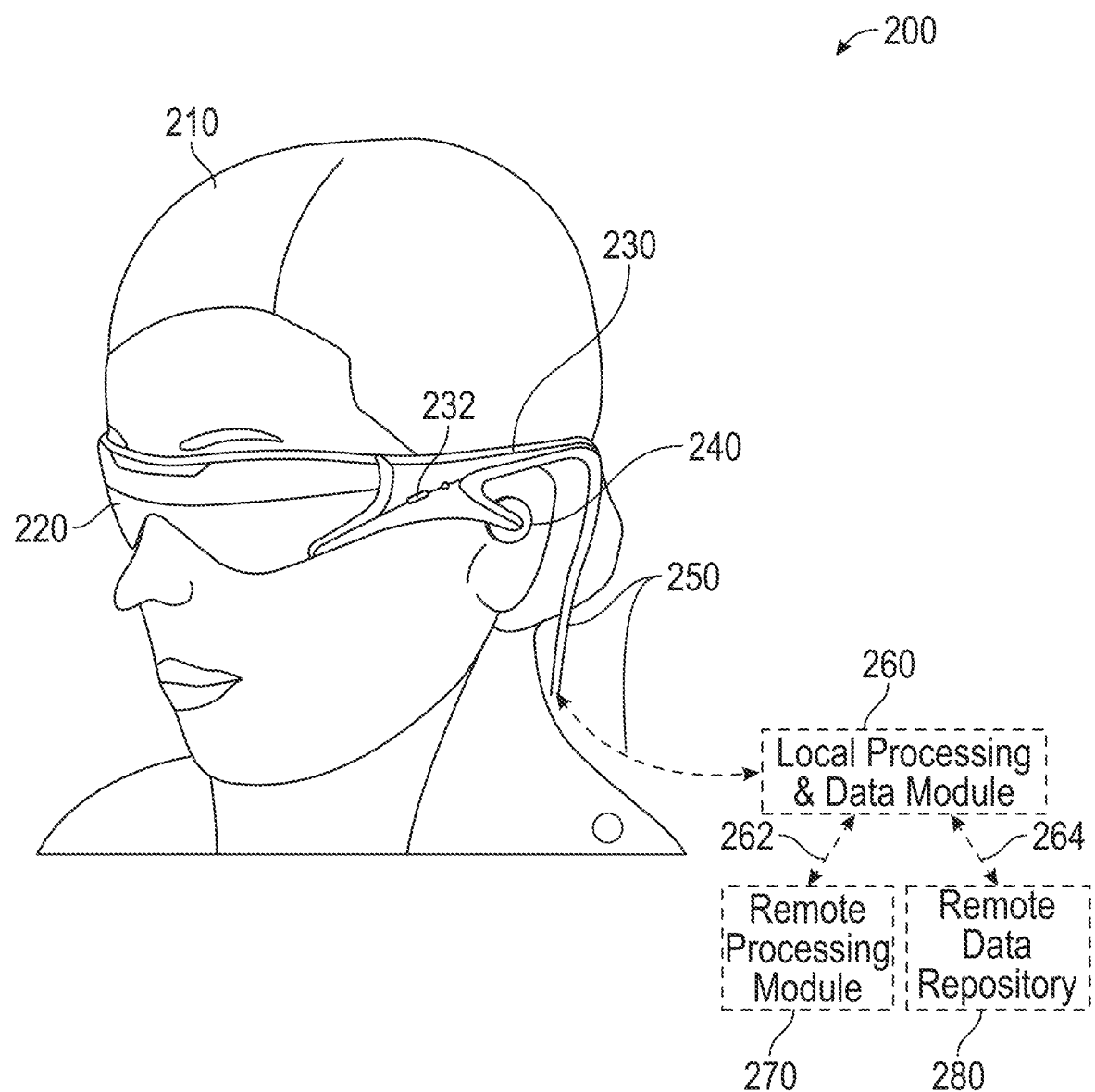
FIG. 2 schematically illustrates an example of a wearable system.

FIG. 2 illustrates an example of wearable system 200 which may be configured to provide an AR/VR/MR scene. The wearable system 200 may also be referred to as the AR system 200. The wearable system 200 includes a display 220, and various mechanical and electronic modules and systems to support the functioning of display 220. The display 220 may be coupled to a frame 230, which is wearable by a user, wearer, or viewer 210. The display 220 may be positioned in front of the eyes of the user 210. The display 220 may present AR/VR/MR content to a user. Because the display 220 may be configured to be worn on the head of the user 210, it may also be referred to as a head-mounted display (HMD) and the wearable system 200, comprising the display 220, may also be referred to as a head-mounted display system.

In some embodiments, a speaker 240 is coupled to the frame 230 and positioned adjacent the ear canal of the user (in some embodiments, another speaker, not shown, is positioned adjacent the other ear canal of the user to provide for stereo/shapeable sound control). The display 220 may include an audio sensor (e.g., a microphone) 232 for detecting an audio stream from the environment and capture ambient sound. In some embodiments, one or more other audio sensors, not shown, are positioned to provide stereo sound reception. Stereo sound reception may be used to determine the location of a sound source. The wearable system 200 may perform voice or speech recognition on the audio stream.

The wearable system 200 may include an outward-facing imaging system 464 (shown in FIG. 4) which observes the world in the environment around the user. The wearable system 200 may also include an inward-facing imaging system 462 (shown in FIG. 4) which may track the eye movements of the user. The inward-facing imaging system may track either one eye's movements or both eyes' movements. The inward-facing imaging system 462 may be attached to the frame 230 and may be in electrical communication with the processing modules 260 or 270, which may process image information acquired by the inward-facing imaging system to determine, e.g., the pupil diameters or orientations of the eyes, eye movements or eye pose of the user 210. The inward-facing imaging system 462 may include one or more cameras. For example, at least one camera may be used to image each eye. The images acquired by the cameras may be used to determine pupil size or eye pose for each eye separately, thereby allowing presentation of image information to each eye to be dynamically tailored to that eye.

As an example, the wearable system 200 may use the outward-facing imaging system 464 or the inward-facing imaging system 462 to acquire images of a pose of the user. The images may be still images, frames of a video, or a video.

The display 220 may be operatively coupled 250, such as by a wired lead or wireless connectivity, to a local data processing module 260 which may be mounted in a variety of configurations, such as fixedly attached to the frame 230, fixedly attached to a helmet or hat worn by the user, embedded in headphones, or otherwise removably attached to the user 210 (e.g., in a backpack-style configuration, in a belt-coupling style configuration).

The local processing and data module 260 may comprise a hardware processor, as well as digital memory, such as non-volatile memory (e.g., flash memory), both of which may be utilized to assist in the processing, caching, and storage of data. The data may include data a) captured from sensors (which may be, e.g., operatively coupled to the frame 230 or otherwise attached to the user 210), such as image capture devices (e.g., cameras in the inward-facing imaging system or the outward-facing imaging system), audio sensors (e.g., microphones), inertial measurement units (IMUs), accelerometers, compasses, global positioning system (GPS) units, radio devices, or gyroscopes; or b) acquired or processed using remote processing module 270 or remote data repository 280, possibly for passage to the display 220 after such processing or retrieval. The local processing and data module 260 may be operatively coupled by communication links 262 or 264, such as via wired or wireless communication links, to the remote processing module 270 or remote data repository 280 such that these remote modules are available as resources to the local processing and data module 260. In addition, remote processing module 280 and remote data repository 280 may be operatively coupled to each other.

In some embodiments, the remote processing module 270 may comprise one or more processors configured to analyze and process data or image information. In some embodiments, the remote data repository 280 may comprise a digital data storage facility, which may be available through the internet or other networking configuration in a "cloud" resource configuration. In some embodiments, all data is stored and all computations are performed in the local processing and data module, allowing fully autonomous use from a remote module.

Example Components of a Wearable System

Figure 3:
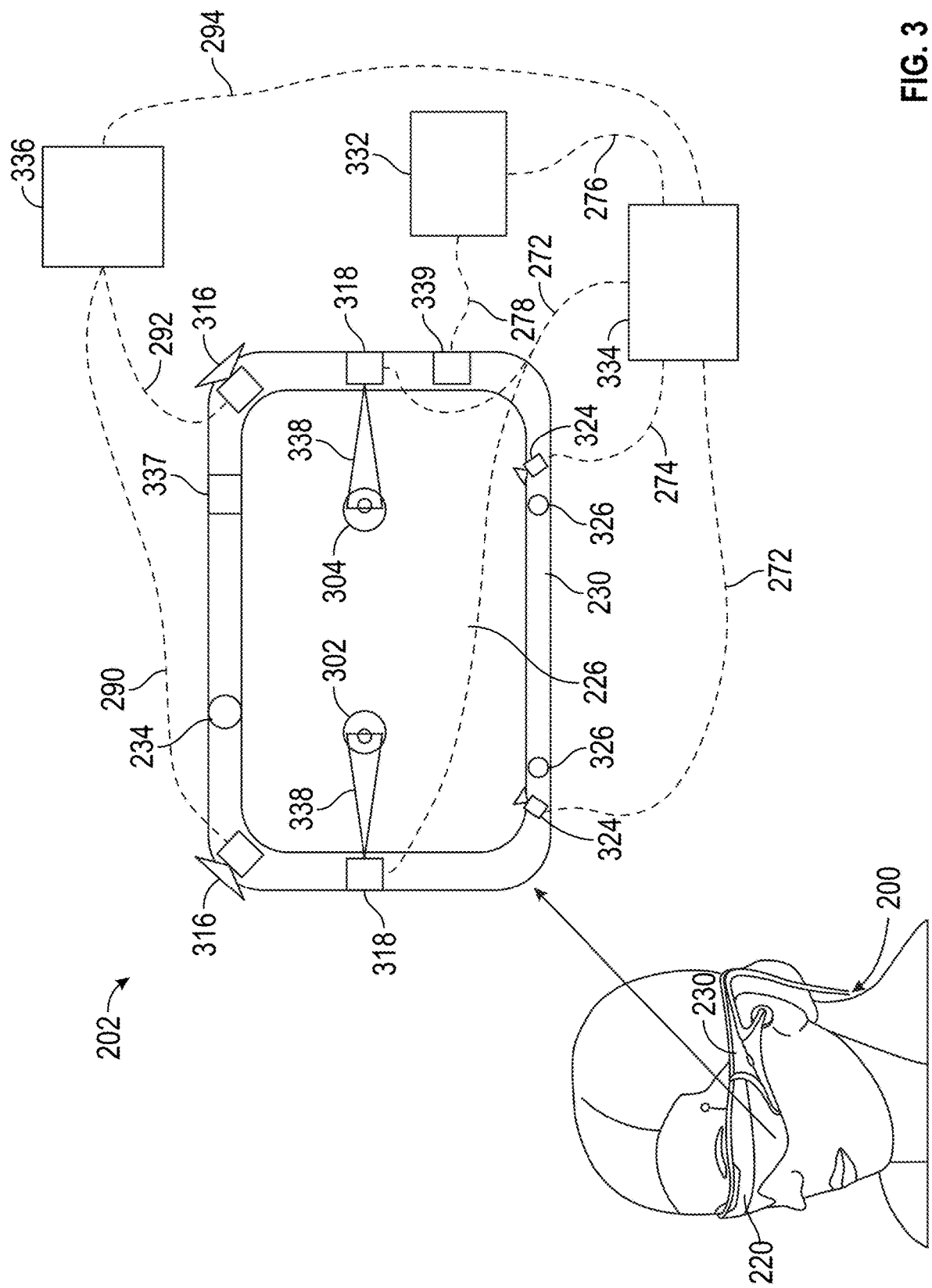
FIG. 3 schematically illustrates example components of a wearable system.

FIG. 3 schematically illustrates example components of a wearable system. FIG. 3 shows a wearable system 200 which may include a display 220 and a frame 230. A blown-up view 202 schematically illustrates various components of the wearable system 200. In certain implements, one or more of the components illustrated in FIG. 3 may be part of the display 220. The various components alone or in combination may collect a variety of data (such as e.g., audio or visual data) associated with the user of the wearable system 200 or the user's environment. It should be appreciated that other embodiments may have additional or fewer components depending on the application for which the wearable system is used. Nevertheless, FIG. 3 provides a basic idea of some of the various components and types of data that may be collected, analyzed, and stored through the wearable system.

FIG. 3 shows an example wearable system 200 which may include the display 220. The display 220 may comprise a display lens 226 that may be mounted to a user's head or a housing or frame 230, which corresponds to the frame 230. The display lens 226 may comprise one or more transparent mirrors positioned by the housing 230 in front of the user's eyes 302, 304 and may be configured to bounce projected light 338 into the eyes 302, 304 and facilitate beam shaping, while also allowing for transmission of at least some light from the local environment. The wavefront of the projected light beam 338 may be bent or focused to coincide with a desired focal distance of the projected light. As illustrated, two wide-field of view machine vision cameras 316 (also referred to as world cameras) may be coupled to the housing 230 to image the environment around the user. These cameras 316 may be dual capture visible light/non-visible (e.g., infrared) light cameras. The cameras 316 may be part of the outward-facing imaging system 464 shown in FIG. 4. Image acquired by the world cameras 316 may be processed by the pose processor 336. For example, the pose processor 336 may implement one or more object recognizers 708 (e.g., shown in FIG. 7) to identify a pose of a user or another person in the user's environment or to identify a physical object in the user's environment.

With continued reference to FIG. 3, a pair of light projector modules (e.g., scanned-laser shaped-wavefront (e.g., for depth) light projector modules) with display mirrors and optics configured to project light 338 into the eyes 302, 304 are shown. The depicted view also shows two miniature infrared cameras 324 paired with infrared light sources 326 (such as light emitting diodes "LED"s), which are configured to be able to track the eyes 302, 304 of the user to support rendering and user input. The cameras 324 may be part of the inward-facing imaging system 462 shown in FIG. 4. The wearable system 200 may further feature a sensor assembly 339, which may comprise X, Y, and Z axis accelerometer capability as well as a magnetic compass and X, Y, and Z axis gyro capability, preferably providing data at a relatively high frequency, such as 200 Hz. The sensor assembly 339 may be part of the IMU described with reference to FIG. 2A The depicted system 200 may also comprise a head pose processor 336, such as an ASIC (application specific integrated circuit), FPGA (field programmable gate array), or ARM processor (advanced reduced-instruction-set machine), which may be configured to calculate real or near-real time user head pose from wide field of view image information output from the capture devices 316. The head pose processor 336 may be a hardware processor and may be implemented as part of the local processing and data module 260 shown in FIG. 2A.

The wearable system may also include one or more depth sensors 234. The depth sensor 234 may be configured to measure the distance between an object in an environment to a wearable device. The depth sensor 234 may include a laser scanner (e.g., a lidar), an ultrasonic depth sensor, or a depth sensing camera. In certain implementations, where the cameras 316 have depth sensing ability, the cameras 316 may also be considered as depth sensors 234.

Also shown is a processor 332 configured to execute digital or analog processing to derive pose from the gyro, compass, or accelerometer data from the sensor assembly 339. The processor 332 may be part of the local processing and data module 260 shown in FIG. 2. The wearable system 200 as shown in FIG. 3 may also include a position system such as, e.g., a GPS 337 (global positioning system) to assist with pose and positioning analyses. In addition, the GPS may further provide remotely-based (e.g., cloud-based) information about the user's environment. This information may be used for recognizing objects or information in user's environment.

The wearable system may combine data acquired by the GPS 337 and a remote computing system (such as, e.g., the remote processing module 270, another user's ARD, etc.) which may provide more information about the user's environment. As one example, the wearable system may determine the user's location based on GPS data and retrieve a world map (e.g., by communicating with a remote processing module 270) including virtual objects associated with the user's location. As another example, the wearable system 200 may monitor the environment using the world cameras 316 (which may be part of the outward-facing imaging system 464 shown in FIG. 4). Based on the images acquired by the world cameras 316, the wearable system 200 may detect objects in the environment (e.g., by using one or more object recognizers 708 shown in FIG. 7). The wearable system may further use data acquired by the GPS 337 to interpret the characters.

The wearable system 200 may also comprise a rendering engine 334 which may be configured to provide rendering information that is local to the user to facilitate operation of the scanners and imaging into the eyes of the user, for the user's view of the world. The rendering engine 334 may be implemented by a hardware processor (such as, e.g., a central processing unit or a graphics processing unit). In some embodiments, the rendering engine is part of the local processing and data module 260. The rendering engine 334 may be communicatively coupled (e.g., via wired or wireless links) to other components of the wearable system 200. For example, the rendering engine 334, may be coupled to the eye cameras 324 via communication link 274, and be coupled to a projecting subsystem 318 (which may project light into user's eyes 302, 304 via a scanned laser arrangement in a manner similar to a retinal scanning display) via the communication link 272. The rendering engine 334 may also be in communication with other processing units such as, e.g., the sensor pose processor 332 and the image pose processor 336 via links 276 and 294 respectively.

The cameras 324 (e.g., mini infrared cameras) may be utilized to track the eye pose to support rendering and user input. Some example eye poses may include where the user is looking or at what depth he or she is focusing (which may be estimated with eye vergence). The GPS 337, gyros, compass, and accelerometers 339 may be utilized to provide coarse or fast pose estimates. One or more of the cameras 316 may acquire images and pose, which in conjunction with data from an associated cloud computing resource, may be utilized to map the local environment and share user views with others.

The example components depicted in FIG. 3 are for illustration purposes only. Multiple sensors and other functional modules are shown together for ease of illustration and description. Some embodiments may include only one or a subset of these sensors or modules. Further, the locations of these components are not limited to the positions depicted in FIG. 3. Some components may be mounted to or housed within other components, such as a belt-mounted component, a hand-held component, or a helmet component. As one example, the image pose processor 336, sensor pose processor 332, and rendering engine 334 may be positioned in a beltpack and configured to communicate with other components of the wearable system via wireless communication, such as ultra-wideband, Wi-Fi, Bluetooth, etc., or via wired communication. The depicted housing 230 preferably is head-mountable and wearable by the user. However, some components of the wearable system 200 may be worn to other portions of the user's body. For example, the speaker 240 may be inserted into the ears of a user to provide sound to the user.

Regarding the projection of light 338 into the eyes 302, 304 of the user, in some embodiment, the cameras 324 may be utilized to measure where the centers of a user's eyes are geometrically verged to, which, in general, coincides with a position of focus, or "depth of focus", of the eyes. A 3-dimensional surface of all points the eyes verge to may be referred to as the "horopter". The focal distance may take on a finite number of depths, or may be infinitely varying. Light projected from the vergence distance appears to be focused to the subject eye 302, 304, while light in front of or behind the vergence distance is blurred. Examples of wearable devices and other display systems of the present disclosure are also described in U.S. Patent Publication No. 2016/0270656, which is incorporated by reference herein in its entirety.

The human visual system is complicated and providing a realistic perception of depth is challenging. Viewers of an object may perceive the object as being three-dimensional due to a combination of vergence and accommodation. Vergence movements (e.g., rolling movements of the pupils toward or away from each other to converge the lines of sight of the eyes to fixate upon an object) of the two eyes relative to each other are closely associated with focusing (or "accommodation") of the lenses of the eyes. Under normal conditions, changing the focus of the lenses of the eyes, or accommodating the eyes, to change focus from one object to another object at a different distance will automatically cause a matching change in vergence to the same distance, under a relationship known as the "accommodation-vergence reflex." Likewise, a change in vergence will trigger a matching change in accommodation, under normal conditions. Display systems that provide a better match between accommodation and vergence may form more realistic and comfortable simulations of three-dimensional imagery.

Further spatially coherent light with a beam diameter of less than about 0.7 millimeters may be correctly resolved by the human eye regardless of where the eye focuses. Thus, to create an illusion of proper focal depth, the eye vergence may be tracked with the cameras 324, and the rendering engine 334 and projection subsystem 318 may be utilized to render all objects on or close to the horopter in focus, and all other objects at varying degrees of defocus (e.g., using intentionally-created blurring). Preferably, the system 220 renders to the user at a frame rate of about 60 frames per second or greater. As described above, preferably, the cameras 324 may be utilized for eye tracking, and software may be configured to pick up not only vergence geometry but also focus location cues to serve as user inputs. Preferably, such a display system is configured with brightness and contrast suitable for day or night use.

In some embodiments, the display system preferably has latency of less than about 20 milliseconds for visual object alignment, less than about 0.1 degree of angular alignment, and about 1 arc minute of resolution, which, without being limited by theory, is believed to be approximately the limit of the human eye. The display system 220 may be integrated with a localization system, which may involve GPS elements, optical tracking, compass, accelerometers, or other data sources, to assist with position and pose determination; localization information may be utilized to facilitate accurate rendering in the user's view of the pertinent world (e.g., such information would facilitate the glasses to know where they are with respect to the real world).

In some embodiments, the wearable system 200 is configured to display one or more virtual images based on the accommodation of the user's eyes. Unlike prior 3D display approaches that force the user to focus where the images are being projected, in some embodiments, the wearable system is configured to automatically vary the focus of projected virtual content to allow for a more comfortable viewing of one or more images presented to the user. For example, if the user's eyes have a current focus of 1 m, the image may be projected to coincide with the user's focus. If the user shifts focus to 3 m, the image is projected to coincide with the new focus. Thus, rather than forcing the user to a predetermined focus, the wearable system 200 of some embodiments allows the user's eye to a function in a more natural manner.

Such a wearable system 200 may eliminate or reduce the incidences of eye strain, headaches, and other physiological symptoms typically observed with respect to virtual reality devices. To achieve this, various embodiments of the wearable system 200 are configured to project virtual images at varying focal distances, through one or more variable focus elements (VFEs). In one or more embodiments, 3D perception may be achieved through a multi-plane focus system that projects images at fixed focal planes away from the user. Other embodiments employ variable plane focus, wherein the focal plane is moved back and forth in the z-direction to coincide with the user's present state of focus.

In both the multi-plane focus systems and variable plane focus systems, wearable system 200 may employ eye tracking to determine a vergence of the user's eyes, determine the user's current focus, and project the virtual image at the determined focus. In other embodiments, wearable system 200 comprises a light modulator that variably projects, through a fiber scanner, or other light generating source, light beams of varying focus in a raster pattern across the retina. Thus, the ability of the display of the wearable system 200 to project images at varying focal distances not only eases accommodation for the user to view objects in 3D, but may also be used to compensate for user ocular anomalies, as further described in U.S. Patent Publication No. 2016/0270656, which is incorporated by reference herein in its entirety. In some other embodiments, a spatial light modulator may project the images to the user through various optical components. For example, as described further below, the spatial light modulator may project the images onto one or more waveguides, which then transmit the images to the user.

Waveguide Stack Assembly

Figure 4:
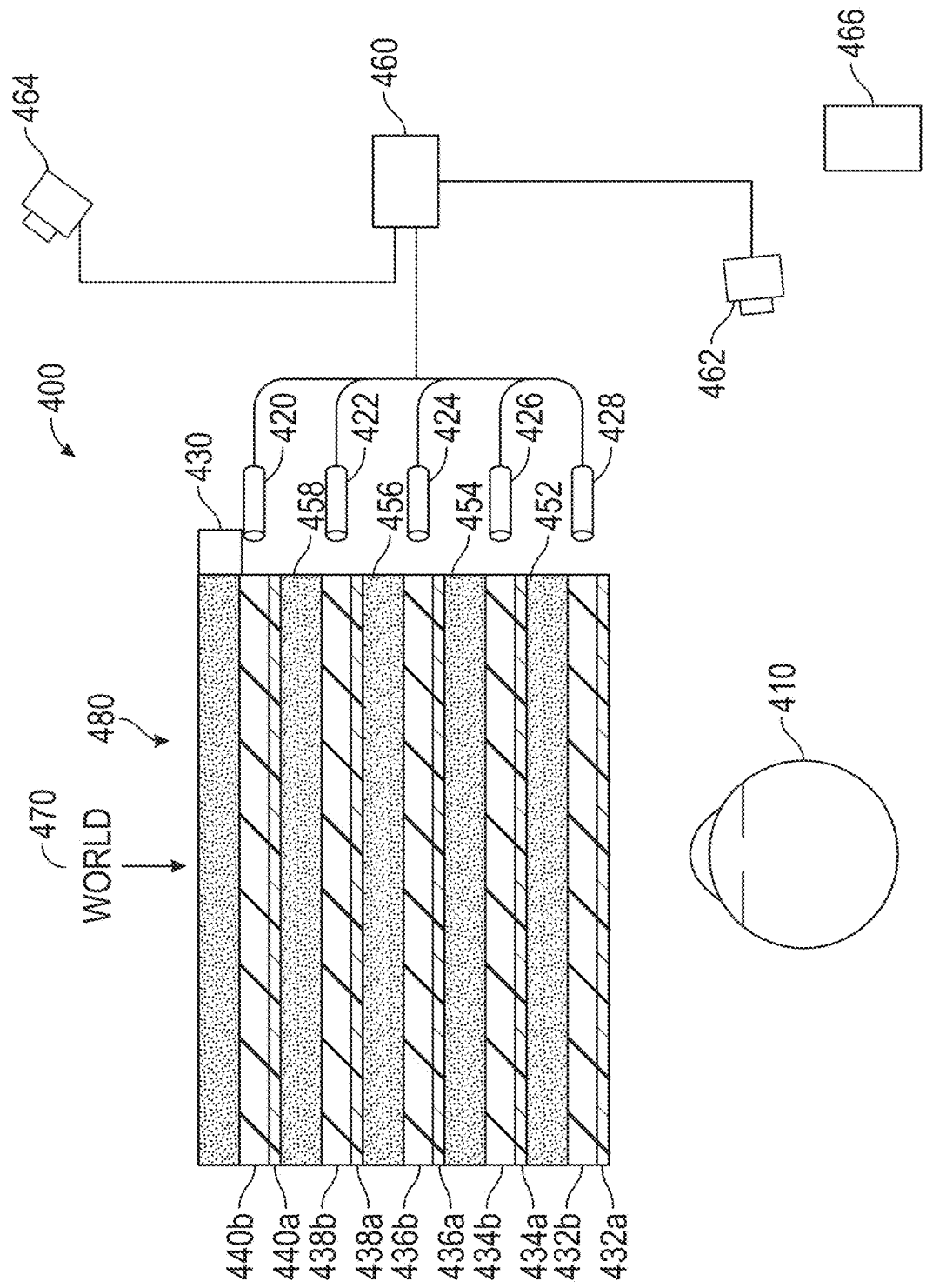
FIG. 4 schematically illustrates an example of a waveguide stack of a wearable device for outputting image information to a user.

FIG. 4 illustrates an example of a waveguide stack for outputting image information to a user. A wearable system 400 includes a stack of waveguides, or stacked waveguide assembly 480 that may be utilized to provide three-dimensional perception to the eye/brain using a plurality of waveguides 432b, 434b, 436b, 438b, 4400b. In some embodiments, the wearable system 400 may correspond to wearable system 200 of FIG. 2, with FIG. 4 schematically showing some parts of that wearable system 200 in greater detail. For example, in some embodiments, the waveguide assembly 480 may be integrated into the display 220 of FIG. 2.

With continued reference to FIG. 4, the waveguide assembly 480 may also include a plurality of features 458, 456, 454, 452 between the waveguides. In some embodiments, the features 458, 456, 454, 452 may be lenses. In other embodiments, the features 458, 456, 454, 452 may not be lenses. Rather, they may simply be spacers (e.g., cladding layers or structures for forming air gaps).

The waveguides 432b, 434b, 436b, 438b, 440b or the plurality of lenses 458, 456, 454, 452 may be configured to send image information to the eye with various levels of wavefront curvature or light ray divergence. Each waveguide level may be associated with a particular depth plane and may be configured to output image information corresponding to that depth plane. Image injection devices 420, 422, 424, 426, 428 may be utilized to inject image information into the waveguides 440b, 438b, 436b, 434b, 432b, each of which may be configured to distribute incoming light across each respective waveguide, for output toward the eye 410. Light exits an output surface of the image injection devices 420, 422, 424, 426, 428 and is injected into a corresponding input edge of the waveguides 440b, 438b, 436b, 434b, 432b. In some embodiments, a single beam of light (e.g., a collimated beam) may be injected into each waveguide to output an entire field of cloned collimated beams that are directed toward the eye 410 at particular angles (and amounts of divergence) corresponding to the depth plane associated with a particular waveguide.

In some embodiments, the image injection devices 420, 422, 424, 426, 428 are discrete displays that each produce image information for injection into a corresponding waveguide 440b, 438b, 436b, 434b, 432b, respectively. In some other embodiments, the image injection devices 420, 422, 424, 426, 428 are the output ends of a single multiplexed display which may, e.g., pipe image information via one or more optical conduits (such as fiber optic cables) to each of the image injection devices 420, 422, 424, 426, 428.

A controller 460 controls the operation of the stacked waveguide assembly 480 and the image injection devices 420, 422, 424, 426, 428. The controller 460 includes programming (e.g., instructions in a non-transitory computer-readable medium) that regulates the timing and provision of image information to the waveguides 440b, 438b, 436b, 434b, 432b. In some embodiments, the controller 460 may be a single integral device, or a distributed system connected by wired or wireless communication channels. The controller 460 may be part of the processing modules 260 or 270 (illustrated in FIG. 2) in some embodiments.

The waveguides 440b, 438b, 436b, 434b, 432b may be configured to propagate light within each respective waveguide by total internal reflection (TIR). The waveguides 440b, 438b, 436b, 434b, 432b may each be planar or have another shape (e.g., curved), with major top and bottom surfaces and edges extending between those major top and bottom surfaces. In the illustrated configuration, the waveguides 440b, 438b, 436b, 434b, 432b may each include light extracting optical elements 440a, 438a, 436a, 434a, 432a that are configured to extract light out of a waveguide by redirecting the light, propagating within each respective waveguide, out of the waveguide to output image information to the eye 410. Extracted light may also be referred to as outcoupled light, and light extracting optical elements may also be referred to as outcoupling optical elements. An extracted beam of light is outputted by the waveguide at locations at which the light propagating in the waveguide strikes a light redirecting element. The light extracting optical elements (440a, 438a, 436a, 434a, 432a) may, for example, be reflective or diffractive optical features. While illustrated disposed at the bottom major surfaces of the waveguides 440b, 438b, 436b, 434b, 432b for ease of description and drawing clarity, in some embodiments, the light extracting optical elements 440a, 438a, 436a, 434a, 432a may be disposed at the top or bottom major surfaces, or may be disposed directly in the volume of the waveguides 440b, 438b, 436b, 434b, 432b. In some embodiments, the light extracting optical elements 440a, 438a, 436a, 434a, 432a may be formed in a layer of material that is attached to a transparent substrate to form the waveguides 440b, 438b, 436b, 434b, 432b. In some other embodiments, the waveguides 440b, 438b, 436b, 434b, 432b may be a monolithic piece of material and the light extracting optical elements 440a, 438a, 436a, 434a, 432a may be formed on a surface or in the interior of that piece of material.

With continued reference to FIG. 4, as discussed herein, each waveguide 440b, 438b, 436b, 434b, 432b is configured to output light to form an image corresponding to a particular depth plane. For example, the waveguide 432b nearest the eye may be configured to deliver collimated light, as injected into such waveguide 432b, to the eye 410. The collimated light may be representative of the optical infinity focal plane. The next waveguide up 434b may be configured to send out collimated light which passes through the first lens 452 (e.g., a negative lens) before it may reach the eye 410. First lens 452 may be configured to create a slight convex wavefront curvature so that the eye/brain interprets light coming from that next waveguide up 434b as coming from a first focal plane closer inward toward the eye 410 from optical infinity. Similarly, the third up waveguide 436b passes its output light through both the first lens 452 and second lens 454 before reaching the eye 410. The combined optical power of the first and second lenses 452 and 454 may be configured to create another incremental amount of wavefront curvature so that the eye/brain interprets light coming from the third waveguide 436b as coming from a second focal plane that is even closer inward toward the person from optical infinity than was light from the next waveguide up 434b.

The other waveguide layers (e.g., waveguides 438b, 440b) and lenses (e.g., lenses 456, 458) are similarly configured, with the highest waveguide 440b in the stack sending its output through all of the lenses between it and the eye for an aggregate focal power representative of the closest focal plane to the person. To compensate for the stack of lenses 458, 456, 454, 452 when viewing/interpreting light coming from the world 470 on the other side of the stacked waveguide assembly 480, a compensating lens layer 430 may be disposed at the top of the stack to compensate for the aggregate power of the lens stack 458, 456, 454, 452 below. (Compensating lens layer 430 and the stacked waveguide assembly 480 as a whole may be configured such that light coming from the world 470 is conveyed to the eye 410 at substantially the same level of divergence (or collimation) as the light had when it was initially received by the stacked waveguide assembly 480.) Such a configuration provides as many perceived focal planes as there are available waveguide/lens pairings. Both the light extracting optical elements of the waveguides and the focusing aspects of the lenses may be static (e.g., not dynamic or electro-active). In some alternative embodiments, either or both may be dynamic using electro-active features.

With continued reference to FIG. 4, the light extracting optical elements 440a, 438a, 436a, 434a, 432a may be configured to both redirect light out of their respective waveguides and to output this light with the appropriate amount of divergence or collimation for a particular depth plane associated with the waveguide. As a result, waveguides having different associated depth planes may have different configurations of light extracting optical elements, which output light with a different amount of divergence depending on the associated depth plane. In some embodiments, as discussed herein, the light extracting optical elements 440a, 438a, 436a, 434a, 432a may be volumetric or surface features, which may be configured to output light at specific angles. For example, the light extracting optical elements 440a, 438a, 436a, 434a, 432a may be volume holograms, surface holograms, and/or diffraction gratings. Light extracting optical elements, such as diffraction gratings, are described in U.S. Patent Publication No. 2015/0178939, published Jun. 25, 2015, which is incorporated by reference herein in its entirety.

In some embodiments, the light extracting optical elements 440a, 438a, 436a, 434a, 432a are diffractive features that form a diffraction pattern, or "diffractive optical element" (also referred to herein as a "DOE"). Preferably, the DOE has a relatively low diffraction efficiency so that only a portion of the light of the beam is deflected away toward the eye 410 with each intersection of the DOE, while the rest continues to move through a waveguide via total internal reflection. The light carrying the image information may thus be divided into a number of related exit beams that exit the waveguide at a multiplicity of locations and the result is a fairly uniform pattern of exit emission toward the eye 304 for this particular collimated beam bouncing around within a waveguide.

In some embodiments, one or more DOEs may be switchable between "on" state in which they actively diffract, and "off" state in which they do not significantly diffract. For instance, a switchable DOE may comprise a layer of polymer dispersed liquid crystal, in which microdroplets comprise a diffraction pattern in a host medium, and the refractive index of the microdroplets may be switched to substantially match the refractive index of the host material (in which case the pattern does not appreciably diffract incident light) or the microdroplet may be switched to an index that does not match that of the host medium (in which case the pattern actively diffracts incident light).

In some embodiments, the number and distribution of depth planes or depth of field may be varied dynamically based on the pupil sizes or orientations of the eyes of the viewer. Depth of field may change inversely with a viewer's pupil size. As a result, as the sizes of the pupils of the viewer's eyes decrease, the depth of field increases such that one plane that is not discernible because the location of that plane is beyond the depth of focus of the eye may become discernible and appear more in focus with reduction of pupil size and commensurate with the increase in depth of field. Likewise, the number of spaced apart depth planes used to present different images to the viewer may be decreased with the decreased pupil size. For example, a viewer may not be able to clearly perceive the details of both a first depth plane and a second depth plane at one pupil size without adjusting the accommodation of the eye away from one depth plane and to the other depth plane. These two depth planes may, however, be sufficiently in focus at the same time to the user at another pupil size without changing accommodation.

In some embodiments, the display system may vary the number of waveguides receiving image information based upon determinations of pupil size or orientation, or upon receiving electrical signals indicative of particular pupil size or orientation. For example, if the user's eyes are unable to distinguish between two depth planes associated with two waveguides, then the controller 460 (which may be an embodiment of the local processing and data module 260) may be configured or programmed to cease providing image information to one of these waveguides. Advantageously, this may reduce the processing burden on the system, thereby increasing the responsiveness of the system. In embodiments in which the DOEs for a waveguide are switchable between the on and off states, the DOEs may be switched to the off state when the waveguide does receive image information.

In some embodiments, it may be desirable to have an exit beam meet the condition of having a diameter that is less than the diameter of the eye of a viewer. However, meeting this condition may be challenging in view of the variability in size of the viewer's pupils. In some embodiments, this condition is met over a wide range of pupil sizes by varying the size of the exit beam in response to determinations of the size of the viewer's pupil. For example, as the pupil size decreases, the size of the exit beam may also decrease. In some embodiments, the exit beam size may be varied using a variable aperture.

The wearable system 400 may include an outward-facing imaging system 464 (e.g., a digital camera) that images a portion of the world 470. This portion of the world 470 may be referred to as the field of view (FOV) of a world camera and the imaging system 464 is sometimes referred to as an FOV camera. The FOV of the world camera may or may not be the same as the FOV of a viewer 210 which encompasses a portion of the world 470 the viewer 210 perceives at a given time. For example, in some situations, the FOV of the world camera may be larger than the viewer 210 of the viewer 210 of the wearable system 400. The entire region available for viewing or imaging by a viewer may be referred to as the field of regard (FOR). The FOR may include 4π steradians of solid angle surrounding the wearable system 400 because the wearer may move his body, head, or eyes to perceive substantially any direction in space. In other contexts, the wearer's movements may be more constricted, and accordingly the wearer's FOR may subtend a smaller solid angle. Images obtained from the outward-facing imaging system 464 may be used to track gestures made by the user (e.g., hand or finger gestures), detect objects in the world 470 in front of the user, and so forth.

The wearable system 400 may include an audio sensor 232, e.g., a microphone, to capture ambient sound. As described above, in some embodiments, one or more other audio sensors may be positioned to provide stereo sound reception useful to the determination of location of a speech source. The audio sensor 232 may comprise a directional microphone, as another example, which may also provide such useful directional information as to where the audio source is located. The wearable system 400 may use information from both the outward-facing imaging system 464 and the audio sensor 230 in locating a source of speech, or to determine an active speaker at a particular moment in time, etc. For example, the wearable system 400 may use the voice recognition alone or in combination with a reflected image of the speaker (e.g., as seen in a mirror) to determine the identity of the speaker. As another example, the wearable system 400 may determine a position of the speaker in an environment based on sound acquired from directional microphones. The wearable system 400 may parse the sound coming from the speaker's position with speech recognition algorithms to determine the content of the speech and use voice recognition techniques to determine the identity (e.g., name or other demographic information) of the speaker.

The wearable system 400 may also include an inward-facing imaging system 466 (e.g., a digital camera), which observes the movements of the user, such as the eye movements and the facial movements. The inward-facing imaging system 466 may be used to capture images of the eye 410 to determine the size and/or orientation of the pupil of the eye 304. The inward-facing imaging system 466 may be used to obtain images for use in determining the direction the user is looking (e.g., eye pose) or for biometric identification of the user (e.g., via iris identification). In some embodiments, at least one camera may be utilized for each eye, to separately determine the pupil size or eye pose of each eye independently, thereby allowing the presentation of image information to each eye to be dynamically tailored to that eye. In some other embodiments, the pupil diameter or orientation of only a single eye 410 (e.g., using only a single camera per pair of eyes) is determined and assumed to be similar for both eyes of the user. The images obtained by the inward-facing imaging system 466 may be analyzed to determine the user's eye pose or mood, which may be used by the wearable system 400 to decide which audio or visual content should be presented to the user. The wearable system 400 may also determine head pose (e.g., head position or head orientation) using sensors such as IMUs, accelerometers, gyroscopes, etc.

The wearable system 400 may include a user input device 466 by which the user may input commands to the controller 460 to interact with the wearable system 400. For example, the user input device 466 may include a trackpad, a touchscreen, a joystick, a multiple degree-of-freedom (DOF) controller, a capacitive sensing device, a game controller, a keyboard, a mouse, a directional pad (D-pad), a wand, a haptic device, a totem (e.g., functioning as a virtual user input device), and so forth. A multi-DOF controller may sense user input in some or all possible translations (e.g., left/right, forward/backward, or up/down) or rotations (e.g., yaw, pitch, or roll) of the controller. A multi-DOF controller which supports the translation movements may be referred to as a 3DOF while a multi-DOF controller which supports the translations and rotations may be referred to as кDOF. In some cases, the user may use a finger (e.g., a thumb) to press or swipe on a touch-sensitive input device to provide input to the wearable system 400 (e.g., to provide user input to a user interface provided by the wearable system 400). The user input device 466 may be held by the user's hand during the use of the wearable system 400. The user input device 466 may be in wired or wireless communication with the wearable system 400.

Other Components of the Wearable System

In many implementations, the wearable system may include other components in addition or in alternative to the components of the wearable system described above. The wearable system may, for example, include one or more haptic devices or components. The haptic devices or components may be operable to provide a tactile sensation to a user. For example, the haptic devices or components may provide a tactile sensation of pressure or texture when touching virtual content (e.g., virtual objects, virtual tools, other virtual constructs). The tactile sensation may replicate a feel of a physical object which a virtual object represents, or may replicate a feel of an imagined object or character (e.g., a dragon) which the virtual content represents. In some implementations, haptic devices or components may be worn by the user (e.g., a user wearable glove). In some implementations, haptic devices or components may be held by the user.

The wearable system may, for example, include one or more physical objects which are manipulable by the user to allow input or interaction with the wearable system. These physical objects may be referred to herein as totems. Some totems may take the form of inanimate objects, such as for example, a piece of metal or plastic, a wall, a surface of table. In certain implementations, the totems may not actually have any physical input structures (e.g., keys, triggers, joystick, trackball, rocker switch). Instead, the totem may simply provide a physical surface, and the wearable system may render a user interface so as to appear to a user to be on one or more surfaces of the totem. For example, the wearable system may render an image of a computer keyboard and trackpad to appear to reside on one or more surfaces of a totem. For example, the wearable system may render a virtual computer keyboard and virtual trackpad to appear on a surface of a thin rectangular plate of aluminum which serves as a totem. The rectangular plate does not itself have any physical keys or trackpad or sensors. However, the wearable system may detect user manipulation or interaction or touches with the rectangular plate as selections or inputs made via the virtual keyboard or virtual trackpad. The user input device 466 (shown in FIG. 4) may be an embodiment of a totem, which may include a trackpad, a touchpad, a trigger, a joystick, a trackball, a rocker or virtual switch, a mouse, a keyboard, a multi-degree-of-freedom controller, or another physical input device. A user may use the totem, alone or in combination with poses, to interact with the wearable system or other users.

Examples of haptic devices and totems usable with the wearable devices, HMD, and display systems of the present disclosure are described in U.S. Patent Publication No. 2015/0016777, which is incorporated by reference herein in its entirety.

Example of an Eye Image

Figure 5:
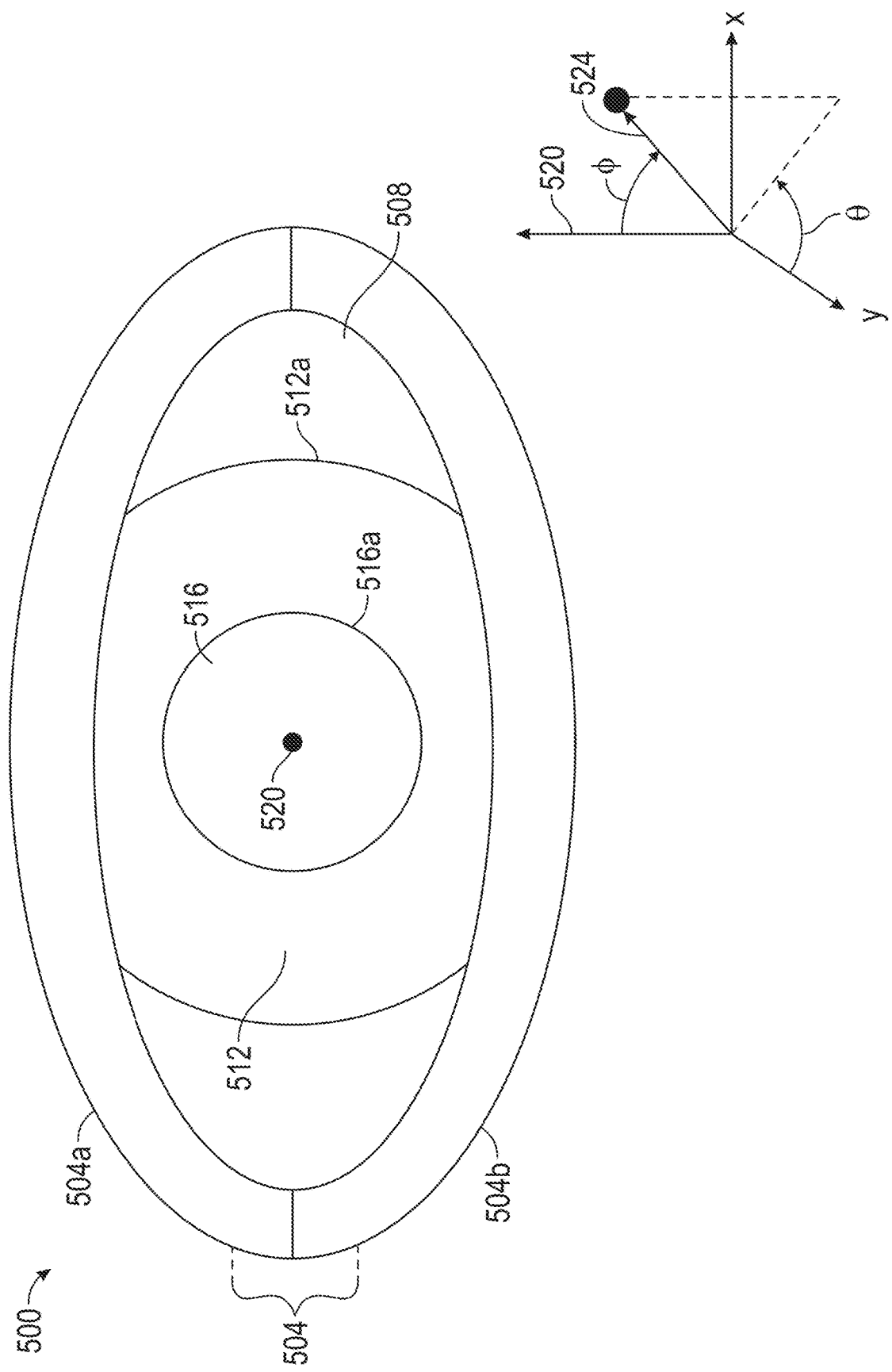
FIG. 5 schematically illustrates an example of an eye.

FIG. 5 illustrates an image of an eye 500 with eyelids 504, sclera 508 (the "white" of the eye), iris 512, and pupil 516. Curve 516a shows the pupillary boundary between the pupil 516 and the iris 512, and curve 512a shows the limbic boundary between the iris 512 and the sclera 508. The eyelids 504 include an upper eyelid 504a and a lower eyelid 504b. The eye 500 is illustrated in a natural resting pose (e.g., in which the user's face and gaze are both oriented as they would be toward a distant object directly ahead of the user). The natural resting pose of the eye 500 may be indicated by a natural resting direction 520, which is a direction orthogonal to the surface of the eye 500 when in the natural resting pose (e.g., directly out of the plane for the eye 500 shown in FIG. 5) and in this example, centered within the pupil 516.

As the eye 500 moves to look toward different objects, the eye pose will change relative to the natural resting direction 520. The current eye pose may be determined with reference to an eye pose direction 524, which is a direction orthogonal to the surface of the eye (and centered in within the pupil 516) but oriented toward the object at which the eye is currently directed. With reference to an example coordinate system shown in FIG. 5, the pose of the eye 500 may be expressed as two angular parameters indicating an azimuthal deflection and a zenithal deflection of the eye pose direction 524 of the eye, both relative to the natural resting direction 520 of the eye. For purposes of illustration, these angular parameters may be represented as θ (azimuthal deflection, determined from a fiducial azimuth) and φ (zenithal deflection, sometimes also referred to as a polar deflection). In some implementations, angular roll of the eye around the eye pose direction 524 may be included in the determination of eye pose, and angular roll may be included in the following analysis. In other implementations, other techniques for determining the eye pose may be used, for example, a pitch, yaw, and optionally roll system.

An eye image may be obtained from a video using any appropriate process, for example, using a video processing algorithm that may extract an image from one or more sequential frames. The pose of the eye may be determined from the eye image using a variety of eye-tracking techniques. For example, an eye pose may be determined by considering the lensing effects of the cornea on light sources that are provided. Any suitable eye tracking technique may be used for determining eye pose in the eyelid shape estimation techniques described herein.

Example of an Eye Tracking System

Figure 6:
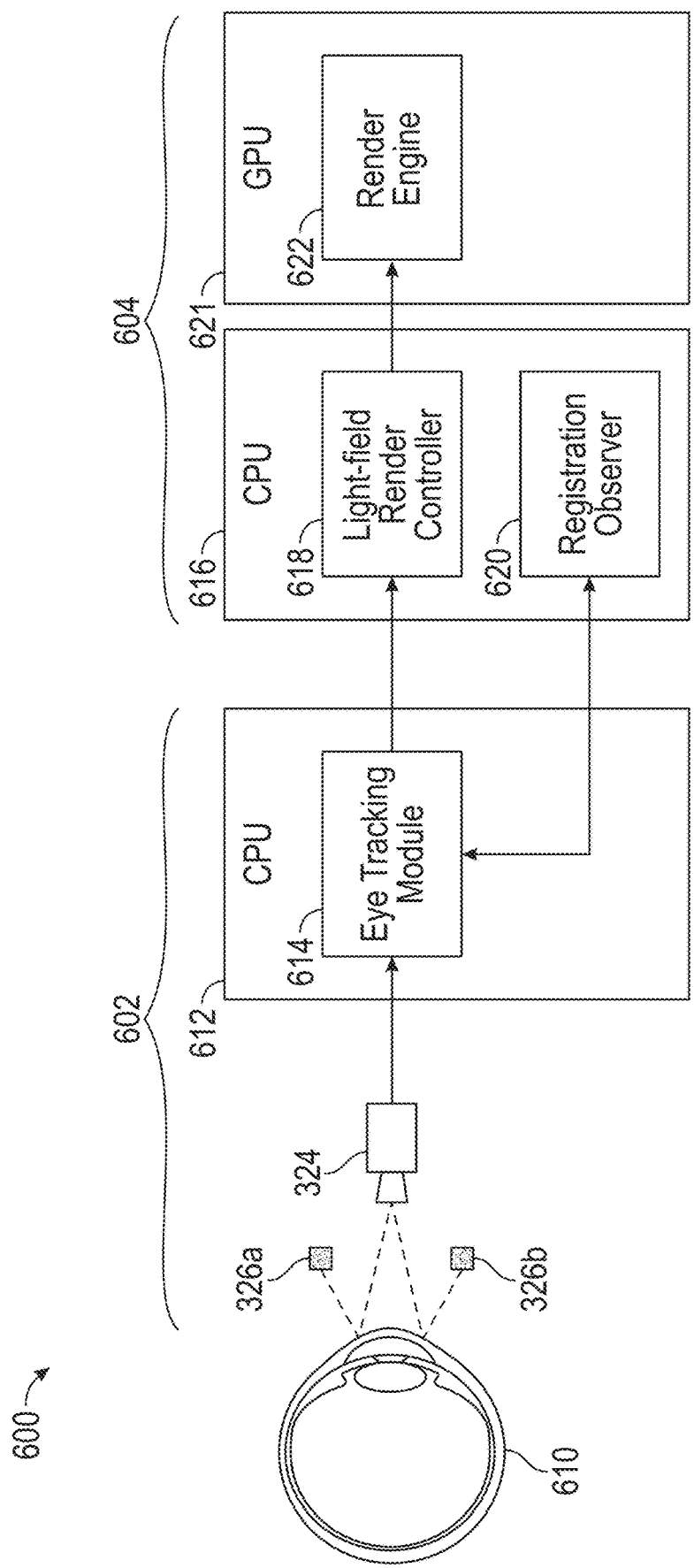
FIG. 6 is a schematic diagram of a wearable system that includes an eye tracking system.

FIG. 6 illustrates a schematic diagram of a wearable, or a head-mounted, display system 600 that includes an eye tracking system. The head-mounted display system 600 may, in at least some embodiments, include components located in a head-mounted unit 602 and components located in a non-head-mounted unit 604. Non-head mounted unit 604 may be, as examples, a belt-mounted component, a hand-held component, a component in a backpack, a remote component, etc. Incorporating some of the components of the head-mounted display system 600 in non-head-mounted unit 604 may help to reduce the size, weight, complexity, and cost of the head-mounted unit 602. In some implementations, some or all of the functionality described as being performed by one or more components of head-mounted unit 602 and/or non-head mounted 604 may be provided by way of one or more components included elsewhere in the head-mounted display system 600. For example, some or all of the functionality described below in association with a CPU 612 of head-mounted unit 602 may be provided by way of a CPU 616 of non-head mounted unit 604, and vice versa. In some examples, some or all of such functionality may be provided by way of peripheral devices of head-mounted display system 600. Furthermore, in some implementations, some or all of such functionality may be provided by way of one or more cloud computing devices or other remotely-located computing devices in a manner similar to that which has been described above with reference to FIG. 2.

As shown in FIG. 6, head-mounted display system 600 may include an eye tracking system including a camera 324 that captures images of a user's eye 610. If desired, the eye tracking system may also include light sources 326a and 326b (such as light emitting diodes "LED"s). The light sources 326a and 326b may generate glints (i.e., reflections off of the user's eyes that appear in images of the eye captured by camera 324). The positions of the light sources 326a and 326b relative to the camera 324 may be known and, as a consequence, the positions of the glints within images captured by camera 324 may be used in tracking the user's eyes (as will be discussed in more detail below in connection with FIGS. 7-11). In at least one embodiment, there may be one light source 326 and one camera 324 associated with a single one of the user's eyes 610. In another embodiment, there may be one light source 326 and one camera 324 associated with each of a user's eyes. 610. In yet other embodiments, there may be one or more cameras 324 and one or more light sources 326 associated with one or each of a user's eyes 610. As a specific example, there may be two light sources 326a and 326b and one or more cameras 324 associated with each of a user's eyes 610. As another example, there may be three or more light sources such as light sources 326a and 326b and one or more cameras 324 associated with each of a user's eyes 610.

Eye tracking module 614 may receive images from eye-tracking camera(s) 324 and may analyze the images to extract various pieces of information. As examples, the eye tracking module 614 may detect the user's eye poses, a three-dimensional position of the user's eye relative to the eye-tracking camera 324 (and to the head-mounted unit 602), the direction one or both of the user's eyes 610 are focused on, the user's vergence depth (i.e., the depth from the user at which the user is focusing on), the positions of the user's pupils, the positions of the user's cornea and cornea sphere, the center of rotation of each of the user's eyes, and the center of perspective of each of the user's eyes. The eye tracking module 614 may extract such information using techniques described below in connection with FIGS. 7-11. As shown in FIG. 6, eye tracking module 614 may be a software module implemented using a CPU 612 in a head-mounted unit 602.

Data from eye tracking module 614 may be provided to other components in the wearable system. As example, such data may be transmitted to components in a non-head-mounted unit 604 such as CPU 616 including software modules for a light-field render controller 618 and a registration observer 620, which may be configured to evaluate whether the display of the head-mounted display system 600 is properly registered with the eyes of the user.

Render controller 618 may use information from eye tracking module 614 to adjust images displayed to the user by render engine 622 (e.g., a render engine that may be a software module in GPU 621 and that may provide images to display 220). As an example, the render controller 618 may adjust images displayed to the user based on the user's center of rotation or center of perspective. In particular, the render controller 618 may use information on the user's center of perspective to simulate a render camera (i.e., to simulate collecting images from the user's perspective) and may adjust images displayed to the user based on the simulated render camera.

A "render camera," which is sometimes also referred to as a "pinhole perspective camera" (or simply "perspective camera") or "virtual pinhole camera" (or simply "virtual camera"), is a simulated camera for use in rendering virtual image content possibly from a database of objects in a virtual world. The objects may have locations and orientations relative to the user or wearer and possibly relative to real objects in the environment surrounding the user or wearer. In other words, the render camera may represent a perspective within render space from which the user or wearer is to view 3D virtual contents of the render space (e.g., virtual objects). The render camera may be managed by a render engine to render virtual images based on the database of virtual objects to be presented to the eye. The virtual images may be rendered as if taken from the perspective the user or wearer. For example, the virtual images may be rendered as if captured by a pinhole camera (corresponding to the "render camera") having a specific set of intrinsic parameters (e.g., focal length, camera pixel size, principal point coordinates, skew/distortion parameters, etc.), and a specific set of extrinsic parameters (e.g., translational components and rotational components relative to the virtual world). The virtual images are taken from the perspective of such a camera having the position and orientation of the render camera (e.g., extrinsic parameters of the render camera). It follows that the system may define and/or adjust intrinsic and extrinsic render camera parameters. For example, the system may define a particular set of extrinsic render camera parameters such that virtual images may be rendered as if captured from the perspective of a camera having a specific location with respect to the user's or wearer's eye so as to provide images that appear to be from the perspective of the user or wearer. The system may later dynamically adjust extrinsic render camera parameters on-the-fly so as to maintain registration with the specific location. Similarly, intrinsic render camera parameters may be defined and dynamically adjusted over time. In some implementations, the images are rendered as if captured from the perspective of a camera having an aperture (e.g., pinhole) at a specific location with respect to the user's or wearer's eye (such as the center of perspective or center of rotation, or elsewhere).

In some embodiments, the system may create or dynamically reposition and/or reorient one render camera for the user's left eye, and another render camera for the user's right eye, as the user's eyes are physically separated from one another and thus consistently positioned at different locations. It follows that, in at least some implementations, virtual content rendered from the perspective of a render camera associated with the viewer's left eye may be presented to the user through an eyepiece on the left side of a head-mounted display (e.g., head-mounted unit 602), and that virtual content rendered from the perspective of a render camera associated with the user's right eye may be presented to the user through an eyepiece on the right side of such a head-mounted display. Further details discussing the creation, adjustment, and use of render cameras in rendering processes are provided in U.S. patent application Ser. No. 15/274,823, entitled "METHODS AND SYSTEMS FOR DETECTING AND COMBINING STRUCTURAL FEATURES IN 3D RECONSTRUCTION," which is expressly incorporated herein by reference in its entirety for all purposes.

In some examples, one or more modules (or components) of the system 600 (e.g., light-field render controller 618, render engine 622, etc.) may determine the position and orientation of the render camera within render space based on the position and orientation of the user's head and eyes (e.g., as determined based on head pose and eye tracking data, respectively). That is, the system 600 may effectively map the position and orientation of the user's head and eyes to particular locations and angular positions within a 3D virtual environment, place and orient render cameras at the particular locations and angular positions within the 3D virtual environment, and render virtual content for the user as it would be captured by the render camera. Further details discussing real world to virtual world mapping processes are provided in U.S. patent application Ser. No. 15/296,869, entitled "SELECTING VIRTUAL OBJECTS IN A THREE-DIMENSIONAL SPACE," which is expressly incorporated herein by reference in its entirety for all purposes. As an example, the render controller 618 may adjust the depths at which images are displayed by selecting which depth plane (or depth planes) are utilized at any given time to display the images. In some implementations, such a depth plane switch may be carried out through an adjustment of one or more intrinsic render camera parameters.

Registration observer 620 may use information from eye tracking module 614 to identify whether the head-mounted unit 602 is properly positioned on a user's head. As an example, the eye tracking module 614 may provide eye location information, such as the positions of the centers of rotation of the user's eyes, indicative of the three-dimensional position of the user's eyes relative to camera 324 and head-mounted unit 602 and the eye tracking module 614 may use the location information to determine if display 220 is properly aligned in the user's field of view, or if the head-mounted unit 602 (or headset) has slipped or is otherwise misaligned with the user's eyes. As examples, the registration observer 620 may be able to determine if the head-mounted unit 602 has slipped down the user's nose bridge, thus moving display 220 away and down from the user's eyes (which may be undesirable), if the head-mounted unit 602 has been moved up the user's nose bridge, thus moving display 220 closer and up from the user's eyes, if the head-mounted unit 602 has been shifted left or right relative the user's nose bridge, if the head-mounted unit 602 has been lifted above the user's nose bridge, or if the head-mounted unit 602 has been moved in these or other ways away from a desired position or range of positions. In general, registration observer 620 may be able to determine if head-mounted unit 602, in general, and displays 220, in particular, are properly positioned in front of the user's eyes. In other words, the registration observer 620 may determine if a left display in display system 220 is appropriately aligned with the user's left eye and a right display in display system 220 is appropriately aligned with the user's right eye. The registration observer 620 may determine if the head-mounted unit 602 is properly positioned by determining if the head-mounted unit 602 is positioned and oriented within a desired range of positions and/or orientations relative to the user's eyes.

In at least some embodiments, registration observer 620 may generate user feedback in the form of alerts, messages, or other content. Such feedback may be provided to the user to inform the user of any misalignment of the head-mounted unit 602, along with optional feedback on how to correct the misalignment (such as a suggestion to adjust the head-mounted unit 602 in a particular manner).

Example registration observation and feedback techniques, which may be utilized by registration observer 620, are described in U.S. patent application Ser. No. 15/717,747, filed Sep. 27, 2017, which is incorporated by reference herein in its entirety.

Example of an Eye Tracking Module

Figure 7A:
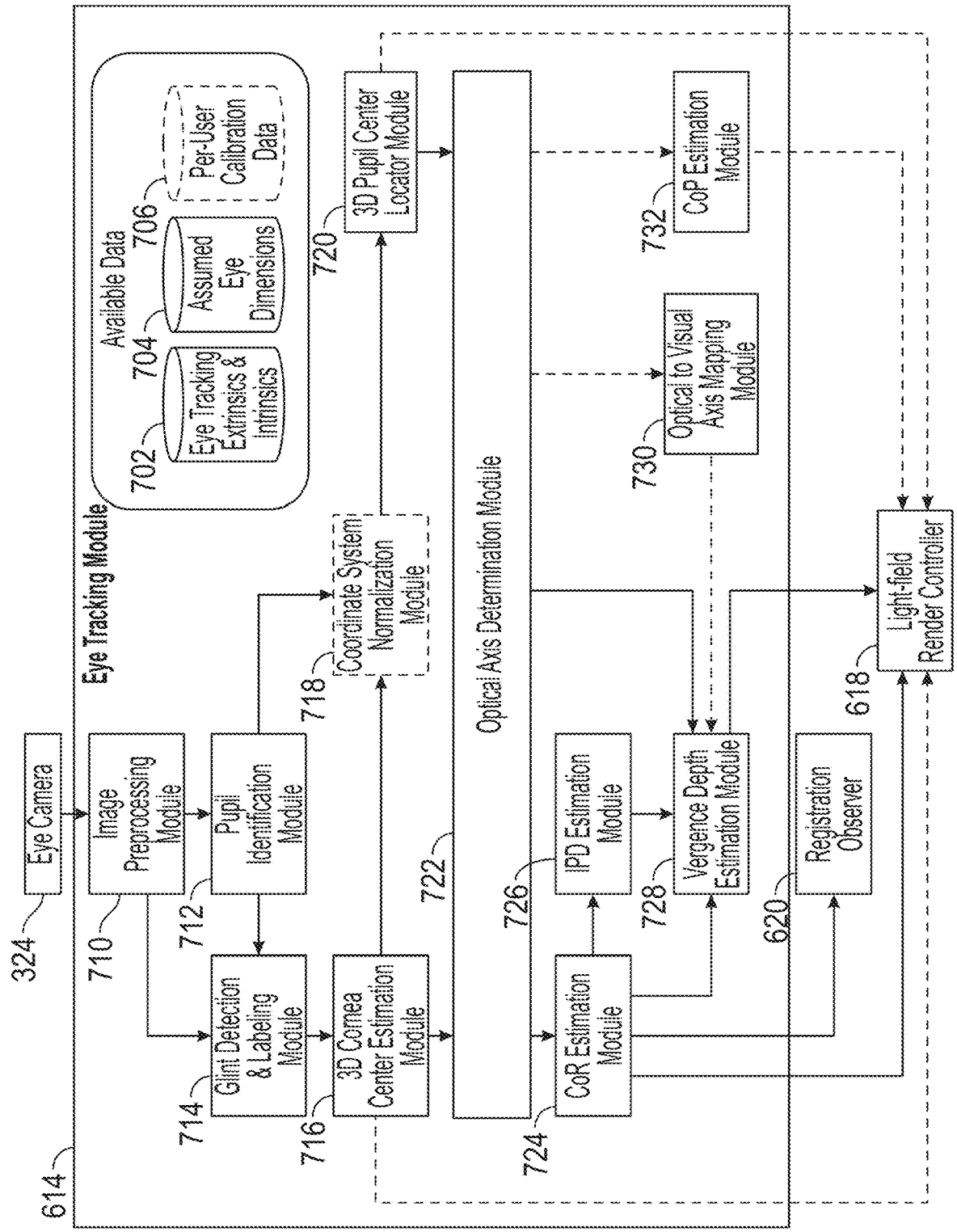
FIG. 7A is a block diagram of a wearable system that may include an eye tracking system.

A detailed block diagram of an example eye tracking module 614 is shown in FIG. 7A. As shown in FIG. 7A, eye tracking module 614 may include a variety of different submodules, may provide a variety of different outputs, and may utilize a variety of available data in tracking the user's eyes. As examples, eye tracking module 614 may utilize available data including eye tracking extrinsics and intrinsics, such as the geometric arrangements of the eye-tracking camera 324 relative to the light sources 326 and the head-mounted-unit 602; assumed eye dimensions 704 such as a typical distance of approximately 4.7 mm between a user's center of cornea curvature and the average center of rotation of the user's eye or typical distances between a user's center of rotation and center of perspective; and per-user calibration data 706 such as a particular user's interpupillary distance. Additional examples of extrinsics, intrinsics, and other information that may be employed by the eye tracking module 614 are described in U.S. patent application Ser. No. 15/497,726, filed Apr. 26, 2017, which is incorporated by reference herein in its entirety.

Image preprocessing module 710 may receive images from an eye camera such as eye camera 324 and may perform one or more preprocessing (i.e., conditioning) operations on the received images. As examples, image preprocessing module 710 may apply a Gaussian blur to the images, may down sample the images to a lower resolution, may applying an unsharp mask, may apply an edge sharpening algorithm, or may apply other suitable filters that assist with the later detection, localization, and labelling of glints, a pupil, or other features in the images from eye camera 324. The image preprocessing module 710 may apply a low-pass filter or a morphological filter such as an open filter, which may remove high-frequency noise such as from the pupillary boundary 516a (see FIG. 5), thereby removing noise that may hinder pupil and glint determination. The image preprocessing module 710 may output preprocessed images to the pupil identification module 712 and to the glint detection and labeling module 714.

Pupil identification module 712 may receive preprocessed images from the image preprocessing module 710 and may identify regions of those images that include the user's pupil. The pupil identification module 712 may, in some embodiments, determine the coordinates of the position, or coordinates, of the center, or centroid, of the user's pupil in the eye tracking images from camera 324. In at least some embodiments, pupil identification module 712 may identify contours in eye tracking images (e.g., contours of pupil iris boundary), identify contour moments (i.e., centers of mass), apply a starburst pupil detection and/or a canny edge detection algorithm, reject outliers based on intensity values, identify sub-pixel boundary points, correct for eye-camera distortion (i.e., distortion in images captured by eye camera 324), apply a random sample consensus (RANSAC) iterative algorithm to fit an ellipse to boundaries in the eye tracking images, apply a tracking filter to the images, and identify sub-pixel image coordinates of the user's pupil centroid. The pupil identification module 712 may output pupil identification data, which may indicate which regions of the preprocessing images module 712 identified as showing the user's pupil, to glint detection and labeling module 714. The pupil identification module 712 may provide the 2D coordinates of the user's pupil (i.e., the 2D coordinates of the centroid of the user's pupil) within each eye tracking image to glint detection module 714. In at least some embodiments, pupil identification module 712 may also provide pupil identification data of the same sort to coordinate system normalization module 718.

Pupil detection techniques, which may be utilized by pupil identification module 712, are described in U.S. Patent Publication No. 2017/0053165, published Feb. 23, 2017 and in U.S. Patent Publication No. 2017/0053166, published Feb. 23, 2017, each of which is incorporated by reference herein in its entirety.

Glint detection and labeling module 714 may receive preprocessed images from module 710 and pupil identification data from module 712. Glint detection module 714 may use this data to detect and/or identify glints (i.e., reflections off of the user's eye of the light from light sources 326) within regions of the preprocessed images that show the user's pupil. As an example, the glint detection module 714 may search for bright regions within the eye tracking image, sometimes referred to herein as "blobs" or local intensity maxima, that are in the vicinity of the user's pupil. In at least some embodiments, the glint detection module 714 may rescale (e.g., enlarge) the pupil ellipse to encompass additional glints. The glint detection module 714 may filter glints by size and/or by intensity. The glint detection module 714 may also determine the 2D positions of each of the glints within the eye tracking image. In at least some examples, the glint detection module 714 may determine the 2D positions of the glints relative to the user's pupil, which may also be referred to as the pupil-glint vectors. Glint detection and labeling module 714 may label the glints and output the preprocessing images with labeled glints to the 3D cornea center estimation module 716. Glint detection and labeling module 714 may also pass along data such as preprocessed images from module 710 and pupil identification data from module 712.

Pupil and glint detection, as performed by modules such as modules 712 and 714, may use any suitable techniques. As examples, edge detection may be applied to the eye image to identify glints and pupils. Edge detection may be applied by various edge detectors, edge detection algorithms, or filters. For example, a Canny Edge detector may be applied to the image to detect edges such as in lines of the image. Edges may include points located along a line that correspond to the local maximum derivative. For example, the pupillary boundary 516a (see FIG. 5) may be located using a Canny edge detector. With the location of the pupil determined, various image processing techniques may be used to detect the "pose" of the pupil 116. Determining an eye pose of an eye image may also be referred to as detecting an eye pose of the eye image. The pose may also be referred to as the gaze, pointing direction, or the orientation of the eye. For example, the pupil may be looking leftwards towards an object, and the pose of the pupil could be classified as a leftwards pose. Other methods may be used to detect the location of the pupil or glints. For example, a concentric ring may be located in an eye image using a Canny Edge detector. As another example, an integro-differential operator may be used to find the pupillary or limbus boundaries of the iris. For example, the Daugman integro-differential operator, the Hough transform, or other iris segmentation techniques may be used to return a curve that estimates the boundary of the pupil or the iris.

3D cornea center estimation module 716 may receive preprocessed images including detected glint data and pupil identification data from modules 710, 712, 714. 3D cornea center estimation module 716 may use these data to estimate the 3D position of the user's cornea. In some embodiments, the 3D cornea center estimation module 716 may estimate the 3D position of an eye's center of cornea curvature or a user's corneal sphere, i.e., the center of an imaginary sphere having a surface portion generally coextensive with the user's cornea. The 3D cornea center estimation module 716 may provide data indicating the estimated 3D coordinates of the corneal sphere and/or user's cornea to the coordinate system normalization module 718, the optical axis determination module 722, and/or the light-field render controller 618. Further details of the operation of the 3D cornea center estimation module 716 are provided herein in connection with FIGS. 8A-8E. Techniques for estimating the positions of eye features such as a cornea or corneal sphere, which may be utilized by 3D cornea center estimation module 716 and other modules in the wearable systems of the present disclosure are discussed in U.S. patent application Ser. No. 15/497,726, filed Apr. 26, 2017, which is incorporated by reference herein in its entirety.

Coordinate system normalization module 718 may optionally (as indicated by its dashed outline) be included in eye tracking module 614. Coordinate system normalization module 718 may receive data indicating the estimated 3D coordinates of the center of the user's cornea (and/or the center of the user's corneal sphere) from the 3D cornea center estimation module 716 and may also receive data from other modules. Coordinate system normalization module 718 may normalize the eye camera coordinate system, which may help to compensate for slippages of the wearable device (e.g., slippages of the head-mounted component from its normal resting position on the user's head, which may be identified by registration observer 620). Coordinate system normalization module 718 may rotate the coordinate system to align the z-axis (i.e., the vergence depth axis) of the coordinate system with the cornea center (e.g., as indicated by the 3D cornea center estimation module 716) and may translate the camera center (i.e., the origin of the coordinate system) to a predetermined distance away from the cornea center such as 30 mm (i.e., module 718 may enlarge or shrink the eye tracking image depending on whether the eye camera 324 was determined to be nearer or further than the predetermined distance). With this normalization process, the eye tracking module 614 may be able to establish a consistent orientation and distance in the eye tracking data, relatively independent of variations of headset positioning on the user's head. Coordinate system normalization module 718 may provide 3D coordinates of the center of the cornea (and/or corneal sphere), pupil identification data, and preprocessed eye tracking images to the 3D pupil center locator module 720. Further details of the operation of the coordinate system normalization module 718 are provided herein in connection with FIGS. 9A-9C.

3D pupil center locator module 720 may receive data, in the normalized or the unnormalized coordinate system, including the 3D coordinates of the center of the user's cornea (and/or corneal sphere), pupil location data, and preprocessed eye tracking images. 3D pupil center locator module 720 may analyze such data to determine the 3D coordinates of the center of the user's pupil in the normalized or unnormalized eye camera coordinate system. The 3D pupil center locator module 720 may determine the location of the user's pupil in three-dimensions based on the 2D position of the pupil centroid (as determined by module 712), the 3D position of the cornea center (as determined by module 716), assumed eye dimensions 704 such as the size of the a typical user's corneal sphere and the typical distance from the cornea center to the pupil center, and optical properties of eyes such as the index of refraction of the cornea (relative to the index of refraction of air) or any combination of these. Further details of the operation of the 3D pupil center locator module 720 are provided herein in connection with FIGS. 9D-9G. Techniques for estimating the positions of eye features such as a pupil, which may be utilized by 3D pupil center locator module 720 and other modules in the wearable systems of the present disclosure are discussed in U.S. patent application Ser. No. 15/497,726, filed Apr. 26, 2017, which is incorporated by reference herein in its entirety.

Optical axis determination module 722 may receive data from modules 716 and 720 indicating the 3D coordinates of the center of the user's cornea and the user's pupil. Based on such data, the optical axis determination module 722 may identify a vector from the position of the cornea center (i.e., from the center of the corneal sphere) to the center of the user's pupil, which may define the optical axis of the user's eye. Optical axis determination module 722 may provide outputs specifying the user's optical axis to modules 724, 728, 730, and 732, as examples.

Center of rotation (CoR) estimation module 724 may receive data from module 722 including parameters of the optical axis of the user's eye (i.e., data indicating the direction of the optical axis in a coordinate system with a known relation to the head-mounted unit 602). CoR estimation module 724 may estimate the center of rotation of a user's eye (i.e., the point around which the user's eye rotates when the user eye rotates left, right, up, and/or down). While eyes may not rotate perfectly around a singular point, assuming a singular point may be sufficient. In at least some embodiments, CoR estimation module 724 may estimate an eye's center of rotation by moving from the center of the pupil (identified by module 720) or the center of curvature of the cornea (as identified by module 716) toward the retina along the optical axis (identified by module 722) a particular distance. This particular distance may be an assumed eye dimension 704. As one example, the particular distance between the center of curvature of the cornea and the CoR may be approximately 4.7 mm. This distance may be varied for a particular user based on any relevant data including the user's age, sex, vision prescription, other relevant characteristics, etc.

In at least some embodiments, the CoR estimation module 724 may refine its estimate of the center of rotation of each of the user's eyes over time. As an example, as time passes, the user will eventually rotate their eyes (to look somewhere else, at something closer, further, or sometime left, right, up, or down) causing a shift in the optical axis of each of their eyes. CoR estimation module 724 may then analyze two (or more) optical axes identified by module 722 and locate the 3D point of intersection of those optical axes. The CoR estimation module 724 may then determine the center of rotation lies at that 3D point of intersection. Such a technique may provide for an estimate of the center of rotation, with an accuracy that improves over time. Various techniques may be employed to increase the accuracy of the CoR estimation module 724 and the determined CoR positions of the left and right eyes. As an example, the CoR estimation module 724 may estimate the CoR by finding the average point of intersection of optical axes determined for various different eye poses over time. As additional examples, module 724 may filter or average estimated CoR positions over time, may calculate a moving average of estimated CoR positions over time, and/or may apply a Kalman filter and known dynamics of the eyes and eye tracking system to estimate the CoR positions over time. As a specific example, module 724 may calculate a weighted average of determined points of optical axes intersection and assumed CoR positions (such as 4.7 mm from an eye's center of cornea curvature), such that the determined CoR may slowly drift from an assumed CoR position (i.e., 4.7 mm behind an eye's center of cornea curvature) to a slightly different location within the user's eye over time as eye tracking data for the user is obtain and thereby enables per-user refinement of the CoR position.

Interpupillary distance (IPD) estimation module 726 may receive data from CoR estimation module 724 indicating the estimated 3D positions of the centers of rotation of the user's left and right eyes. IPD estimation module 726 may then estimate a user's IPD by measuring the 3D distance between the centers of rotation of the user's left and right eyes. In general, the distance between the estimated CoR of the user's left eye and the estimated CoR of the user's right eye may be roughly equal to the distance between the centers of a user's pupils, when the user is looking at optical infinity (i.e., the optical axes of the user's eyes are substantially parallel to one another), which is the typical definition of interpupillary distance (IPD). A user's IPD may be used by various components and modules in the wearable system. As example, a user's IPD may be provided to registration observer 620 and used in assessing how well the wearable device is aligned with the user's eyes (e.g., whether the left and right display lenses are properly spaced in accordance with the user's IPD). As another example, a user's IPD may be provided to vergence depth estimation module 728 and be used in determining a user's vergence depth. Module 726 may employ various techniques, such as those discussed in connection with CoR estimation module 724, to increase the accuracy of the estimated IPD. As examples, IPD estimation module 724 may apply filtering, averaging over time, weighted averaging including assumed IPD distances, Kalman filters, etc. as part of estimating a user's IPD in an accurate manner.

Vergence depth estimation module 728 may receive data from various modules and submodules in the eye tracking module 614 (as shown in connection with FIG. 7A). In particular, vergence depth estimation module 728 may employ data indicating estimated 3D positions of pupil centers (e.g., as provided by module 720 described above), one or more determined parameters of optical axes (e.g., as provided by module 722 described above), estimated 3D positions of centers of rotation (e.g., as provided by module 724 described above), estimated IPD (e.g., Euclidean distance(s) between estimated 3D positions of centers of rotations) (e.g., as provided by module 726 described above), and/or one or more determined parameters of optical and/or visual axes (e.g., as provided by module 722 and/or module 730 described below). Vergence depth estimation module 728 may detect or otherwise obtain a measure of a user's vergence depth, which may be the distance from the user at which the user's eyes are focused. As examples, when the user is looking at an object three feet in front of them, the user's left and right eyes have a vergence depth of three feet; and, while when the user is looking at a distant landscape (i.e., the optical axes of the user's eyes are substantially parallel to one another such that the distance between the centers of the user's pupils may be roughly equal to the distance between the centers of rotation of the user's left and right eyes), the user's left and right eyes have a vergence depth of infinity. In some implementations, the vergence depth estimation module 728 may utilize data indicating the estimated centers of the user's pupils (e.g., as provided by module 720) to determine the 3D distance between the estimated centers of the user's pupils. The vergence depth estimation module 728 may obtain a measure of vergence depth by comparing such a determined 3D distance between pupil centers to estimated IPD (e.g., Euclidean distance(s) between estimated 3D positions of centers of rotations) (e.g., as indicated by module 726 described above). In addition to the 3D distance between pupil centers and estimated IPD, the vergence depth estimation module 728 may utilize known, assumed, estimated, and/or determined geometries to calculate vergence depth. As an example, module 728 may combine 3D distance between pupil centers, estimated IPD, and 3D CoR positions in a trigonometric calculation to estimate (i.e., determine) a user's vergence depth. Indeed, an evaluation of such a determined 3D distance between pupil centers against estimated IPD may serve to indicate a measure of the user's current vergence depth relative to optical infinity. In some examples, the vergence depth estimation module 728 may simply receive or access data indicating an estimated 3D distance between the estimated centers of the user's pupils for purposes of obtaining such a measure of vergence depth. In some embodiments, the vergence depth estimation module 728 may estimate vergence depth by comparing a user's left and right optical axis. In particular, vergence depth estimation module 728 may estimate vergence depth by locating the distance from a user at which the user's left and right optical axes intersect (or where projections of the user's left and right optical axes on a plane such as a horizontal plane intersect). Module 728 may utilize a user's IPD in this calculation, by setting the zero depth to be the depth at which the user's left and right optical axes are separated by the user's IPD. In at least some embodiments, vergence depth estimation module 728 may determine vergence depth by triangulating eye tracking data together with known or derived spatial relationships.

In some embodiments, vergence depth estimation module 728 may estimate a user's vergence depth based on the intersection of the user's visual axes (instead of their optical axes), which may provide a more accurate indication of the distance at which the user is focused on. In at least some embodiments, eye tracking module 614 may include optical to visual axis mapping module 730. As discussed in further detail in connection with FIG. 10, a user's optical and visual axis are generally not aligned. A visual axis is the axis along which a person is looking, while an optical axis is defined by the center of that person's lens and pupil, and may go through the center of the person's retina. In particular, a user's visual axis is generally defined by the location of the user's fovea, which may be offset from the center of a user's retina, thereby resulting in different optical and visual axis. In at least some of these embodiments, eye tracking module 614 may include optical to visual axis mapping module 730. Optical to visual axis mapping module 730 may correct for the differences between a user's optical and visual axis and provide information on the user's visual axis to other components in the wearable system, such as vergence depth estimation module 728 and light-field render controller 618. In some examples, module 730 may use assumed eye dimensions 704 including a typical offset of approximately 5.2° inwards (nasally, towards a user's nose) between an optical axis and a visual axis. In other words, module 730 may shift a user's left optical axis (nasally) rightwards by 5.2° towards the nose and a user's right optical axis (nasally) leftwards by 5.2° towards the nose in order to estimate the directions of the user's left and right optical axes. In other examples, module 730 may utilize per-user calibration data 706 in mapping optical axes (e.g., as indicated by module 722 described above) to visual axes. As additional examples, module 730 may shift a user's optical axes nasally by between 4.0° and 6.5°, by between 4.5° and 6.0°, by between 5.0° and 5.4°, etc., or any ranges formed by any of these values. In some arrangements, the module 730 may apply a shift based at least in part upon characteristics of a particular user such as their age, sex, vision prescription, or other relevant characteristics and/or may apply a shift based at least in part upon a calibration process for a particular user (i.e., to determine a particular user's optical-visual axis offset). In at least some embodiments, module 730 may also shift the origins of the left and right optical axes to correspond with the user's CoP (as determined by module 732) instead of the user's CoR.

Optional center of perspective (CoP) estimation module 732, when provided, may estimate the location of the user's left and right centers of perspective (CoP). A CoP may be a useful location for the wearable system and, in at least some embodiments, is a position just in front of a pupil. In at least some embodiments, CoP estimation module 732 may estimate the locations of a user's left and right centers of perspective based on the 3D location of a user's pupil center, the 3D location of a user's center of cornea curvature, or such suitable data or any combination thereof. As an example, a user's CoP may be approximately 5.01 mm in front of the center of cornea curvature (i.e., 5.01 mm from the corneal sphere center in a direction that is towards the eye's cornea and that is along the optical axis) and may be approximately 2.97 mm behind the outer surface of a user's cornea, along the optical or visual axis. A user's center of perspective may be just in front of the center of their pupil. As examples, a user's CoP may be less than approximately 2.0 mm from the user's pupil, less than approximately 1.0 mm from the user's pupil, or less than approximately 0.5 mm from the user's pupil or any ranges between any of these values. As another example, the center of perspective may correspond to a location within the anterior chamber of the eye. As other examples, the CoP may be between 1.0 mm and 2.0 mm, about 1.0 mm, between 0.25 mm and 1.0 mm, between 0.5 mm and 1.0 mm, or between 0.25 mm and 0.5 mm.

The center of perspective described herein (as a potentially desirable position for a pinhole of a render camera and an anatomical position in a user's eye) may be a position that serves to reduce and/or eliminate undesired parallax shifts. In particular, the optical system of a user's eye is very roughly equivalent to theoretical system formed by a pinhole in front of a lens, projecting onto a screen, with the pinhole, lens, and screen roughly corresponding to a user's pupil/iris, lens, and retina, respectively. Moreover, it may be desirable for there to be little or no parallax shift when two point light sources (or objects) at different distances from the user's eye are rigidly rotated about the opening of the pinhole (e.g., rotated along radii of curvature equal to their respective distance from the opening of the pinhole). Thus, it would seem that the CoP should be located at the center of the pupil of an eye (and such a CoP may be used in some embodiments). However, the human eye includes, in addition to the lens and pinhole of the pupil, a cornea that imparts additional optical power to light propagating toward the retina). Thus, the anatomical equivalent of the pinhole in the theoretical system described in this paragraph may be a region of the user's eye positioned between the outer surface of the cornea of the user's eye and the center of the pupil or iris of the user's eye. For instance, the anatomical equivalent of the pinhole may correspond to a region within the anterior chamber of a user's eye. For various reasons discussed herein, it may be desired to set the CoP to such a position within the anterior chamber of the user's eye.

As discussed above, eye tracking module 614 may provide data, such as estimated 3D positions of left and right eye centers of rotation (CoR), vergence depth, left and right eye optical axis, 3D positions of a user's eye, 3D positions of a user's left and right centers of cornea curvature, 3D positions of a user's left and right pupil centers, 3D positions of a user's left and right center of perspective, a user's IPD, etc., to other components, such as light-field render controller 618 and registration observer 620, in the wearable system. Eye tracking module 614 may also include other submodules that detect and generate data associated with other aspects of a user's eye. As examples, eye tracking module 614 may include a blink detection module that provides a flag or other alert whenever a user blinks and a saccade detection module that provides a flag or other alert whenever a user's eye saccades (i.e., quickly shifts focus to another point).

Example of a Render Controller

Figure 7B:
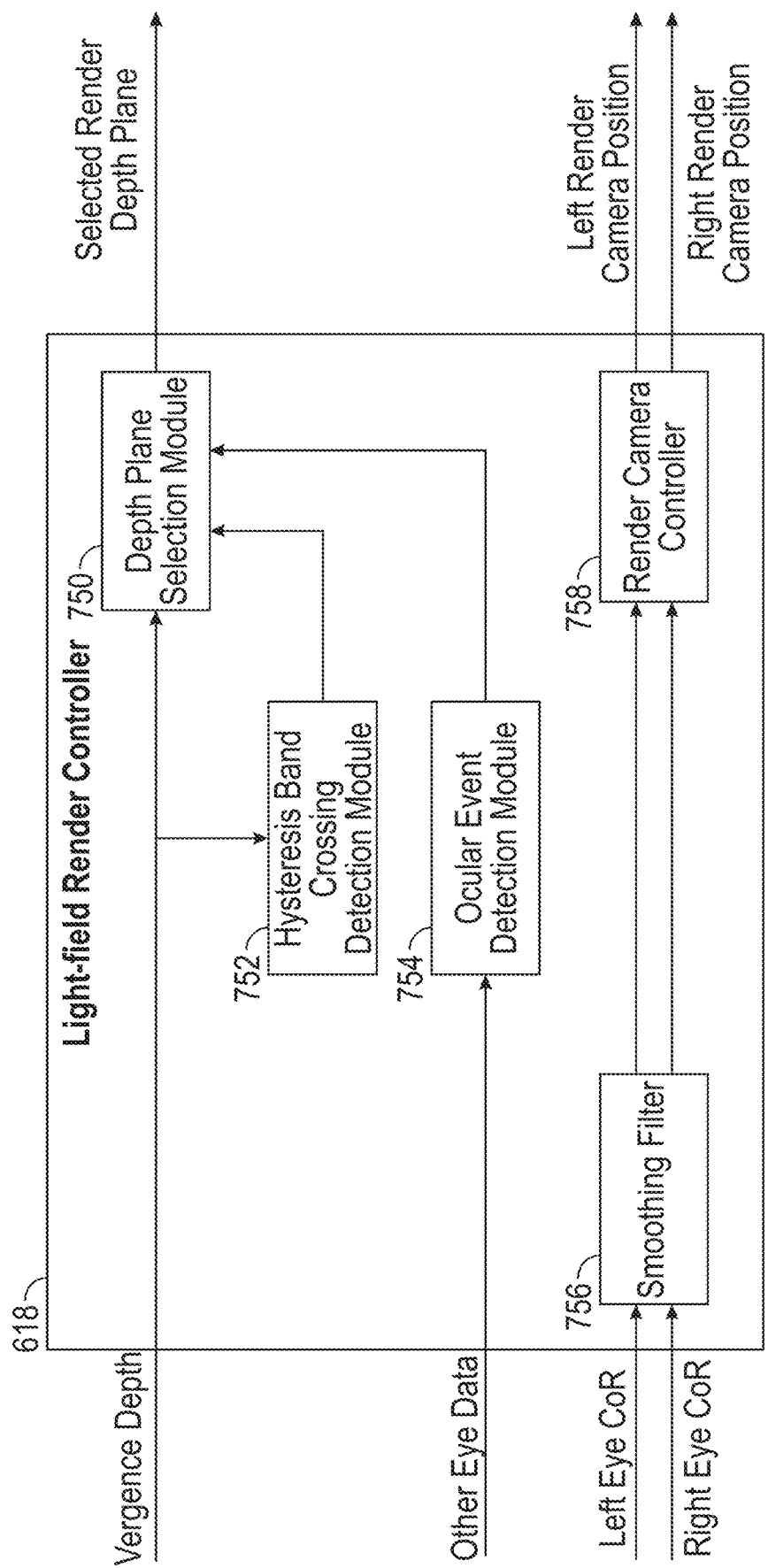
FIG. 7B is a block diagram of a render controller in a wearable system.

A detailed block diagram of an example light-field render controller 618 is shown in FIG. 7B. As shown in FIGS. 6 and 7B, render controller 618 may receive eye tracking information from eye tracking module 614 and may provide outputs to render engine 622, which may generate images to be displayed for viewing by a user of the wearable system. As examples, render controller 618 may receive information regarding a vergence depth, left and right eye centers of rotation (and/or centers of perspective), and other eye data such as blink data, saccade data, etc.

Depth plane selection module 750 may receive vergence depth information and, based on such data, may cause render engine 622 to provide content to a user, with the content appearing to be located on a particular depth plane (i.e., at a particular accommodation or focal distance). As discussed in connection with FIG. 4, a wearable system may include a plurality of discrete depth planes formed by a plurality of waveguides, each conveying image information with a varying level of wavefront curvature. In some embodiments, a wearable system may include one or more variable depth planes, such as an optical element that conveys image information with a level of wavefront curvature that varies over time. In these and other embodiments, depth plane selection module 750 may cause render engine 622 to convey content to a user at a selected depth (i.e., cause render engine 622 to direct display 220 to switch depth planes), based in part of the user's vergence depth. In at least some embodiments, depth plane selection module 750 and render engine 622 may render content at different depths and also generate and/or provide depth plane selection data to display hardware such as display 220. Display hardware such as display 220 may perform an electrical depth plane switching in response to depth plane selection data (which may be control signals) generated by and/or provided by modules such as depth plane selection module 750 and render engine 622.

In general, it may be desirable for depth plane selection module 750 to select a depth plane matching the user's current vergence depth, such that the user is provided with accurate accommodation cues. However, it may also be desirable to switch depth planes in a discreet and unobtrusive manner. As examples, it may be desirable to avoid excessive switching between depth planes and/or it may be desire to switch depth planes at a time when the user is less likely to notice the switch, such as during a blink or eye saccade.

Hysteresis band crossing detection module 752 may help to avoid excessive switching between depth planes, particularly when a user's vergence depth fluctuates at the midpoint or transition point between two depth planes. In particular, module 752 may cause depth plane selection module 750 to exhibit hysteresis in its selection of depth planes. As an example, modules 752 may cause depth plane selection module 750 to switch from a first farther depth plane to a second closer depth plane only after a user's vergence depth passes a first threshold. Similarly, module 752 may cause depth plane selection module 750 (which may in turn direct displays such as display 220) to switch to the first farther depth plane only after the user's vergence depth passes a second threshold that is farther from the user than the first threshold. In the overlapping region between the first and second thresholds, module 750 may cause depth plane selection module 750 to maintain whichever depth plane is currently select as the selected depth plane, thus avoiding excessive switching between depth planes.

Ocular event detection module 750 may receive other eye data from the eye tracking module 614 of FIG. 7A and may cause depth plane selection module 750 to delay some depth plane switches until an ocular event occurs. As an example, ocular event detection module 750 may cause depth plane selection module 750 to delay a planned depth plane switch until a user blink is detected; may receive data from a blink detection component in eye tracking module 614 that indicates when the user is currently blinking; and, in response, may cause depth plane selection module 750 to execute the planned depth plane switch during the blink event (such by causing module 750 to direct display 220 to execute the depth plane switch during the blink event). In at least some embodiments, the wearable system may be able to shift content onto a new depth plane during a blink event such that the user is unlikely to perceive the shift. As another example, ocular event detection module 750 may delay planned depth plane switches until an eye saccade is detected. As discussed in connection with eye blinks, such as an arrangement may facilitate the discrete shifting of depth planes.

If desired, depth plane selection module 750 may delay planned depth plane switches only for a limited period of time before executing the depth plane switch, even in the absence of an ocular event. Similarly, depth plane selection module 750 may execute a depth plane switch when the user's vergence depth is substantially outside of a currently-selected depth plane (i.e., when the user's vergence depth has exceeded a predetermined threshold beyond the regular threshold for a depth plane switch), even in the absence of an ocular event. These arrangements may help ensure that ocular event detection module 754 does not indefinitely delay depth plane switches and does not delay depth plane switches when a large accommodation error is present.

Render camera controller 758 may provide information to render engine 622 indicating where the user's left and right eyes are. Render engine 622 may then generate content by simulating cameras at the positions of the user's left and right eyes and generating content based on the perspectives of the simulated cameras. As discussed above, the render camera is a simulated camera for use in rendering virtual image content possibly from a database of objects in a virtual world. The objects may have locations and orientations relative to the user or wearer and possibly relative to real objects in the environment surrounding the user or wearer. The render camera may be included in a render engine to render virtual images based on the database of virtual objects to be presented to the eye. The virtual images may be rendered as if taken from the perspective the user or wearer. For example, the virtual images may be rendered as if captured by a camera (corresponding to the "render camera") having an aperture, lens, and detector viewing the objects in the virtual world. The virtual images are taken from the perspective of such a camera having a position of the "render camera." For example, the virtual images may be rendered as if captured from the perspective of a camera having a specific location with respect to the user's or wearer's eye so as to provide images that appear to be from the perspective of the user or wearer. In some implementations, the images are rendered as if captured from the perspective of a camera having an aperture at a specific location with respect to the user's or wearer's eye (such as the center of perspective or center of rotation as discussed herein, or elsewhere).

Render camera controller 758 may determine the positions of the left and right cameras based on the left and right eye centers of rotation (CoR), determined by CoR estimation module 724, and/or based on the left and right eye centers of perspective (CoP), determined by CoP estimation module 732. In some embodiments, render camera controller 758 may switch between the CoR and CoP locations based on various factors. As examples, the render camera controller 758 may, in various modes, register the render camera to the CoR locations at all times, register the render camera to the CoP locations at all times, toggle or discretely switch between registering the render camera to the CoR locations and registering the render camera to the CoP locations over time based on various factors, or dynamically register the render camera to any of a range of different positions along the optical (or visual) axis between the CoR and CoP locations over time based on various factors. The CoR and CoP positions may optionally pass through smoothing filter 756 (in any of the aforementioned modes for render camera positioning) which may average the CoR and CoP locations over time to reduce noise in these positions and prevent jitter in the render simulated render cameras.

In at least some embodiments, the render camera may be simulated as a pinhole camera with the pinhole disposed at the position of the estimated CoR or CoP identified by eye tracking module 614. As the CoP is offset from the CoR, the location of the render camera and its pinhole both shift as the user's eye rotates, whenever the render camera's position is based on a user's CoP. In contrast, whenever the render camera's position is based on a user's CoR, the location of the render camera's pinhole does not move with eye rotations, although the render camera (which is behind the pinhole) may, in some embodiments, move with eye rotation. In other embodiments where the render camera's position is based on a user's CoR, the render camera may not move (i.e., rotate) with a user's eye.

Example of a Registration Observer

Figure 7C:
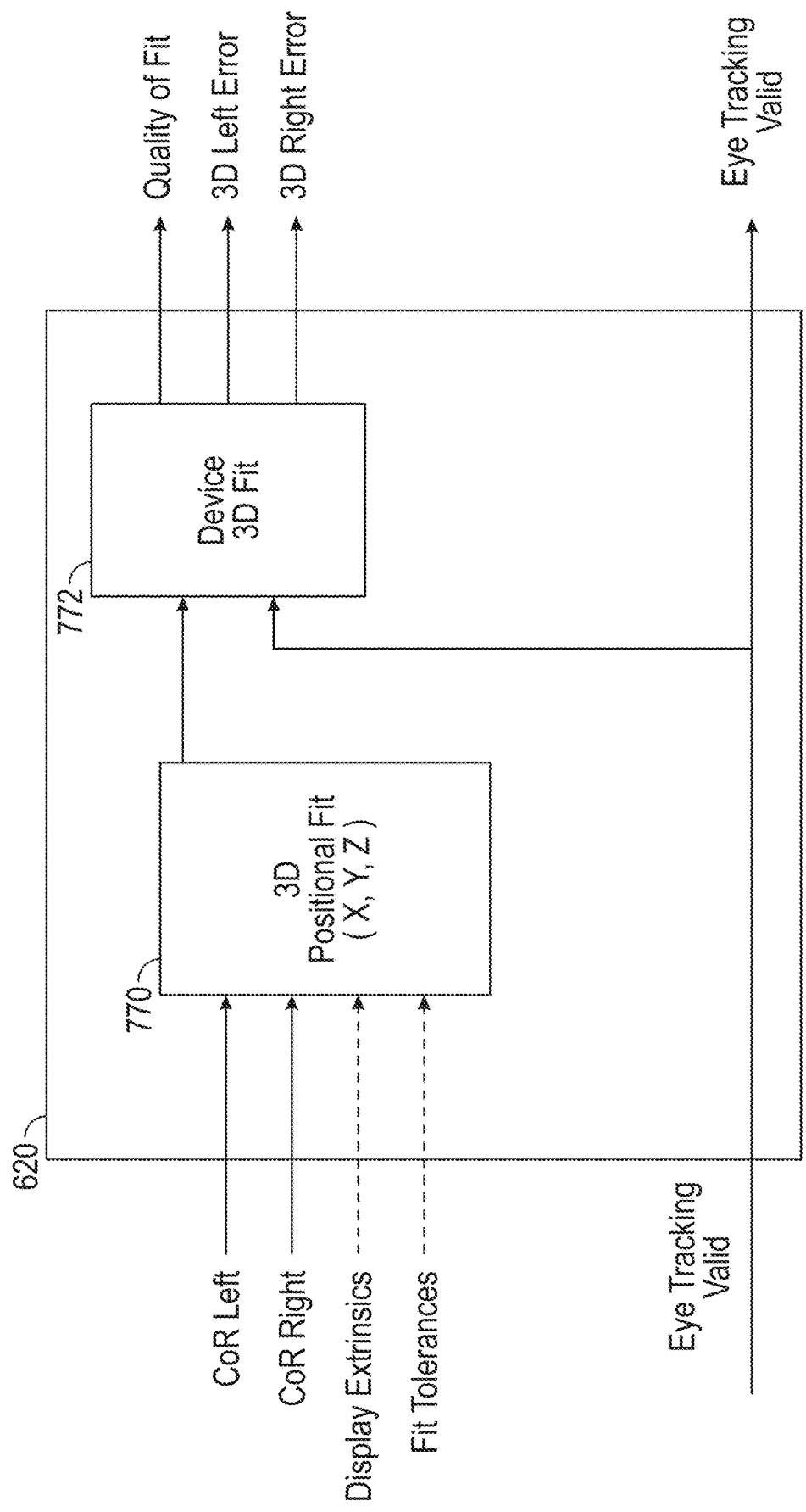
FIG. 7C is a block diagram of a registration observer in a head-mounted display system.

A block diagram of an example registration observer 620 is shown in FIG. 7C. As shown in FIGS. 6, 7A, and 7C, registration observer 620 may receive eye tracking information from eye tracking module 614 (FIGS. 6 and 7A). As examples, registration observer 620 may receive information on a user's left and right eye centers of rotation (e.g., the three-dimensional positions of the user's left and right eye centers of rotations, which may be on a common coordinate system or have a common frame of reference with the head-mounted display system 600). As other examples, registration observer 620 may receive display extrinsics, fit tolerances, and an eye-tracking valid indicator. The display extrinsics may include information on the display (e.g., display 200 of FIG. 2) such as the field of view of the display, the size of one or more display surfaces, and the positions of the display surfaces relative to the head-mounted display system 600. The fit tolerances may include information on display registration volumes, which may indicate how far the user's left and right eyes may move from nominal positions before display performance is impacted. In addition, the fit tolerances may indicate the amount of display performance impact that is expected as a function of the positions of the user's eyes.

As shown in FIG. 7C, registration observer 620 may include a 3D positional fit module 770. The positional fit module 770 may obtain and analyze various pieces of data including, as examples, a left eye center of rotation 3D position (e.g., CoR Left), a right eye center of rotation 3D position (e.g., CoR Right), display extrinsics, and fit tolerances. The 3D positional fit module 770 may determine how far the user's left and right eyes are from the respective left and right eye nominal positions (e.g., may calculate 3D left error and 3D right error) and may provide the error distances (e.g., 3D left error and 3D right error) to device 3D fit module 772.

3D positional fit module 770 may also compare the error distances to the display extrinsics and the fit tolerances to determine if the users eye are within a nominal volume, a partially-degraded volume (e.g., a volume in which the performance of display 220 is partially degraded), or in a fully degraded or nearly fully degraded volume (e.g., a volume in which display 220 is substantially unable to provide content to the user's eyes). In at least some embodiments, 3D positional fit module 770 or 3D fit module 772 may provide an output qualitatively describing the fit of the HMD on the user, such as the Quality of Fit output shown in FIG. 7C. As an example, module 770 may provide an output indicating whether the current fit of the HMD on the user is good, marginal, or failed. A good fit may correspond to a fit that enables the user to view at least a certain percentage of the image (such as 90%), a marginal fit may enable the user to view at least a lower percentage of the image (such as 80%), while a failed fit may be a fit in which only an even lower percentage of the image is visible to the user.

As another example, the 3D positional fit module 770 and/or device 3D fit module 772 may calculate a visible area metric, which may be a percentage of the overall area (or pixels) of images display by display 220 that are visible to the user. Modules 770 and 772 may calculate the visible area metric by evaluating the positions of the user's left and right eyes (e.g., which may be based on the centers of rotation of the user's eyes) relative to display 220 and using one or more models (e.g., a mathematical or geometric model), one or more look-up tables, or other techniques or combinations of these and other techniques to determine what percentage of the images are visible to the user as a function of the positions of the user's eyes. Additionally, modules 770 and 772 may determine which regions or portions of the images display by display 220 are expected to be visible to the user as a function of the positions of the user's eyes.

Registration observer 620 may also include a device 3D fit module 772. Module 772 may receive data from 3D positional fit module 770 and may also receive an eye tracking valid indicator, which may be provided by eye tracking module 614 and may indicate whether the eye tracking system is currently tracking the positions of the user's eyes or if eye tracking data is unavailable or in an error condition (e.g., determined to be no reliable). Device 3D fit module 772 may, if desired, modify quality of fit data received from 3D positional fit module 770 depending on the state of the eye tracking valid data. For example, if the data from the eye tracking system is indicated to not be available or to have an error, the device 3D fit module 772 may provide a notification that there is an error and/or not provide output to the user regarding fit quality or fit errors.

In at least some embodiments, registration observer 620 may provide feedback to users on the quality of fit as well as details of the nature and magnitude of the error. As examples, the head-mounted display system may provide feedback to the user during calibration or fitting processes (e.g., as part of a setup procedure) and may provide feedback during operation (e.g., if the fit degrades due to slippage, the registration observer 620 may prompt the user to readjust the head-mounted display system). In some embodiments, the registration analysis may be performed automatically (e.g., during use of the head-mounted display system) and the feedback may be provided without user input. These are merely illustrative examples.

Example of Locating a User's Cornea with an Eye Tracking System

Figure 8A:
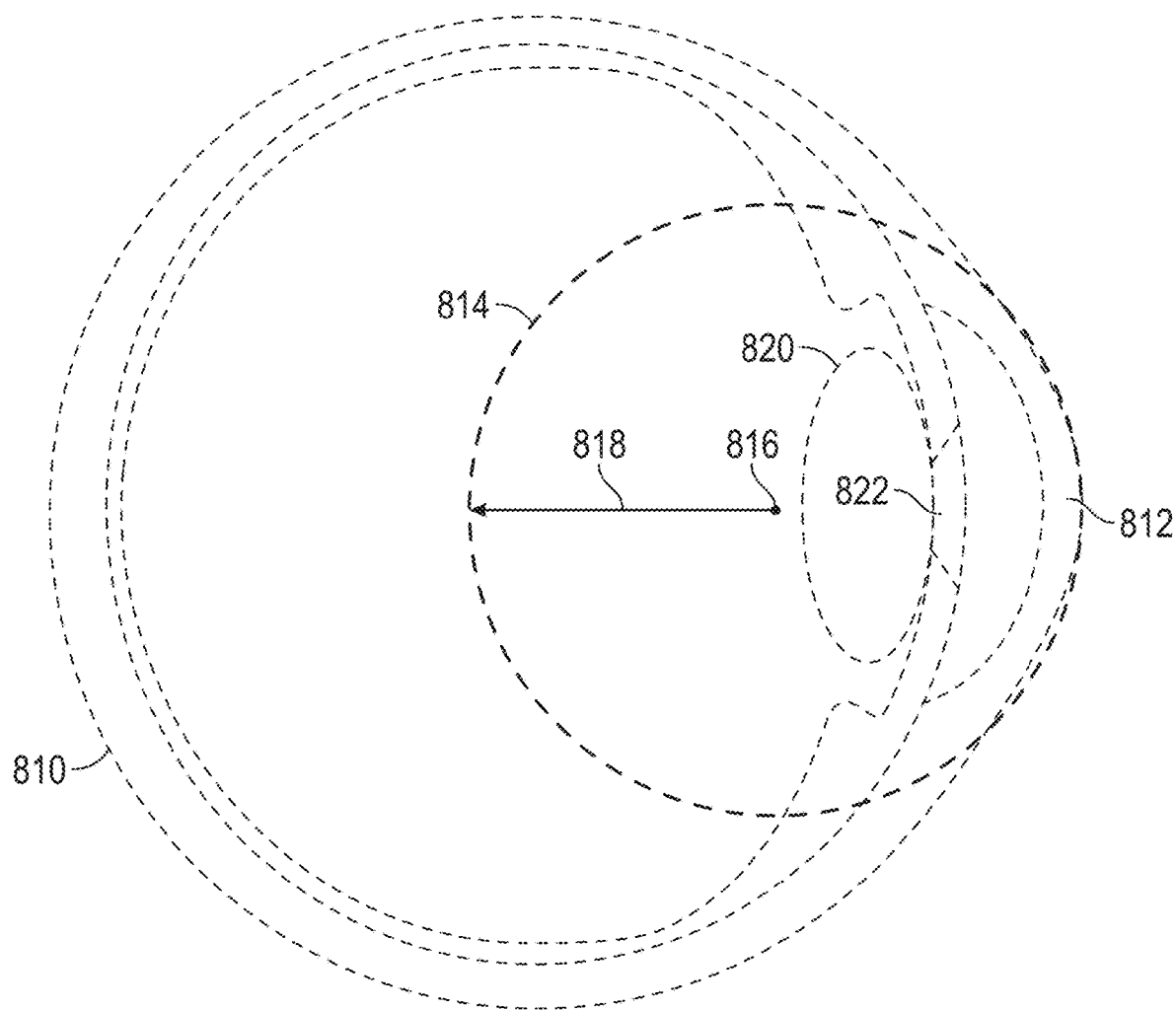
FIG. 8A is a schematic diagram of an eye showing the eye's corneal sphere.

FIG. 8A is a schematic diagram of an eye showing the eye's corneal sphere. As shown in FIG. 8A, a user's eye 810 may have a cornea 812, a pupil 822, and a lens 820. The cornea 812 may have an approximately spherical shape, shown by corneal sphere 814. Corneal sphere 814 may have a center point 816, also referred to as a corneal center, and a radius 818. The semispherical cornea of a user's eye may curve around the corneal center 816.

FIGS. 8B-8E illustrate an example of locating a user's corneal center 816 using 3D cornea center estimation module 716 and eye tracking module 614.

Figure 8B:
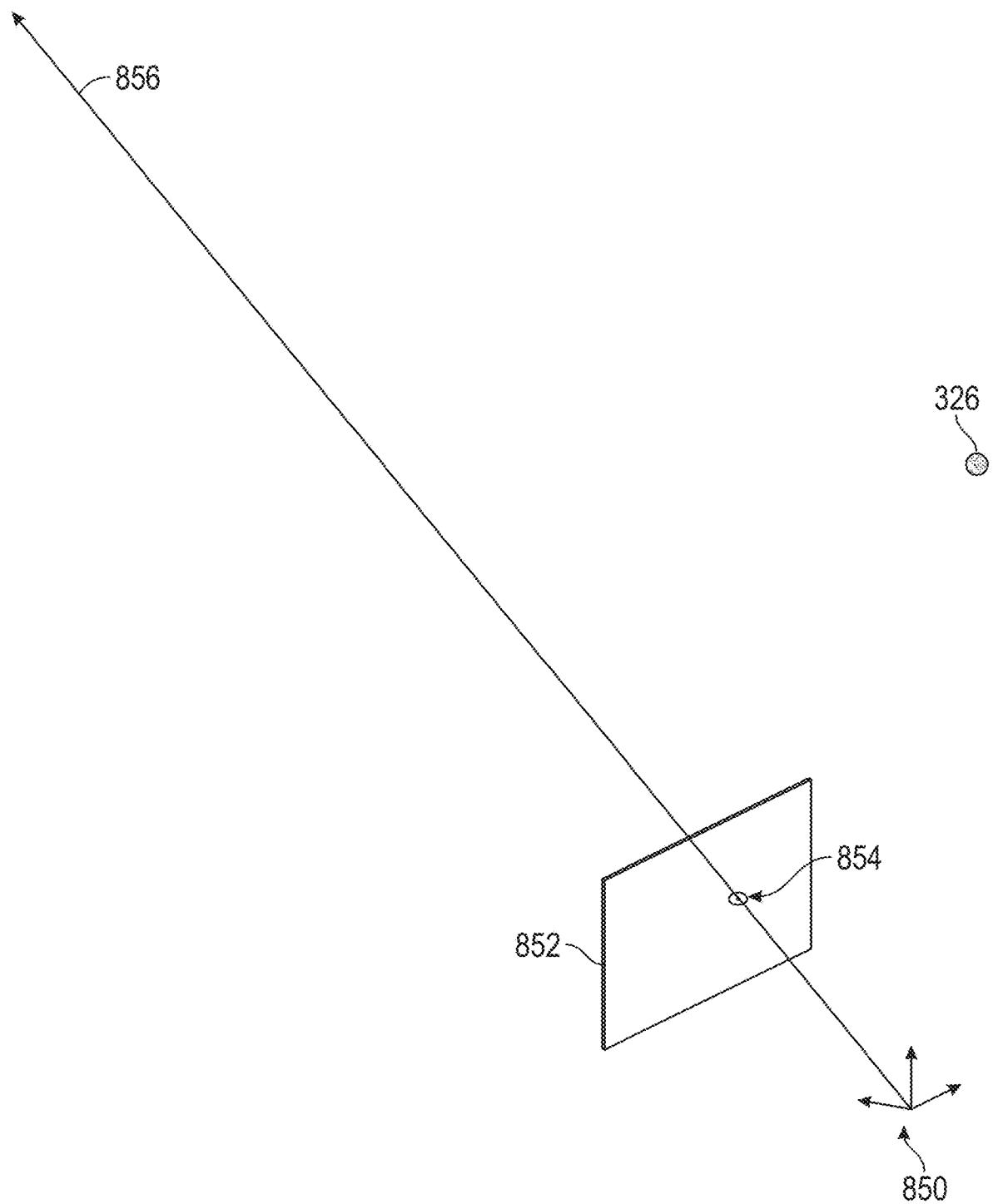
FIG. 8B illustrates an example corneal glint detected by an eye-tracking camera.

As shown in FIG. 8B, 3D cornea center estimation module 716 may receive an eye tracking image 852 that includes a corneal glint 854. The 3D cornea center estimation module 716 may then simulate, in an eye camera coordinate system 850, the known 3D positions of the eye camera 324 and light source 326 (which may be based on data in eye tracking extrinsics & intrinsics database 702, assumed eye dimensions database 704, and/or per-user calibration data 706) in order to cast a ray 856 in the eye camera coordinate system. In at least some embodiments, the eye camera coordinate system 850 may have its origin at the 3D position of the eye-tracking camera 324.

Figure 8C:
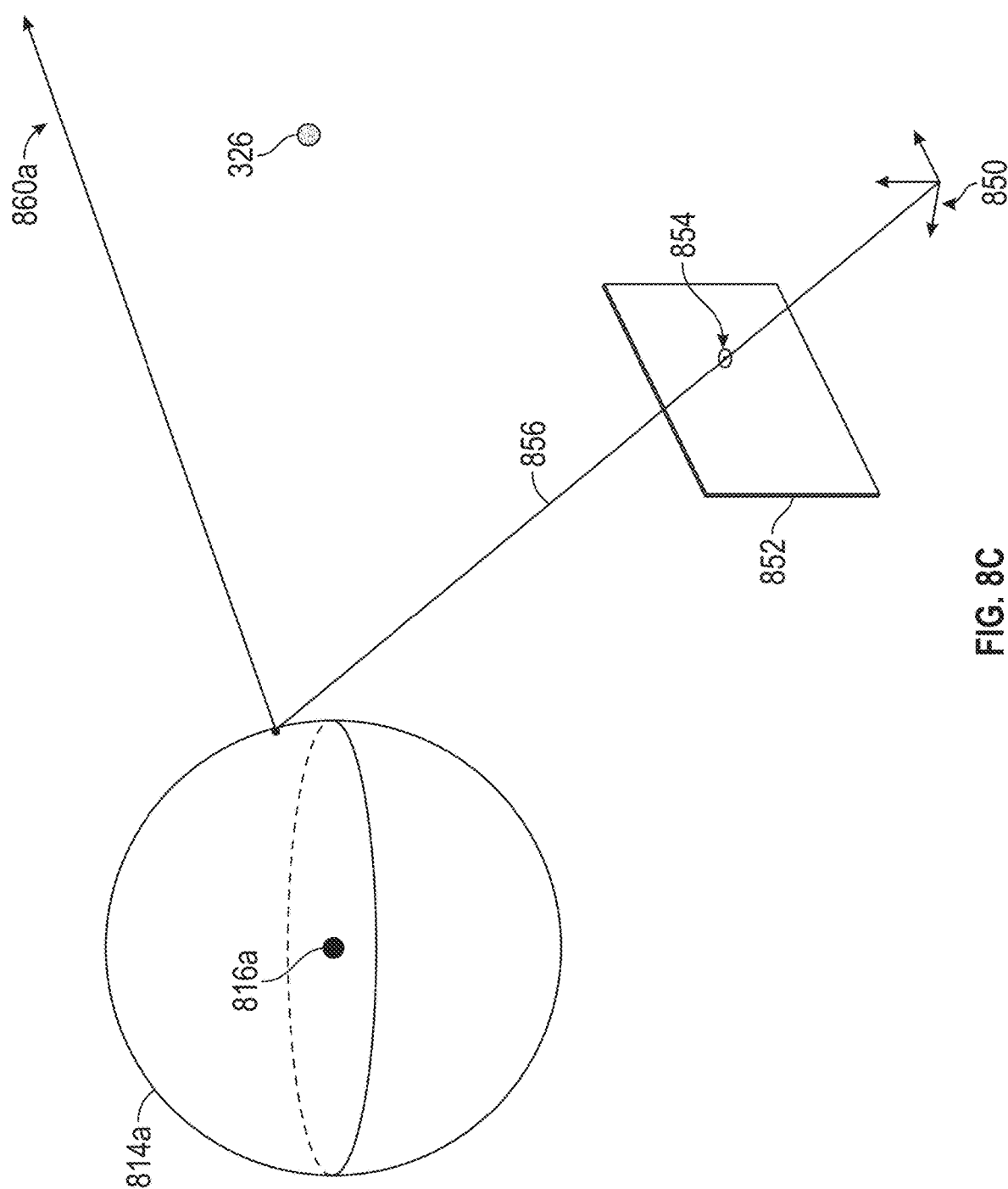

In FIG. 8C, 3D cornea center estimation module 716 simulates a corneal sphere 814a (which may be based on assumed eye dimensions from database 704) and corneal curvature center 816a at a first position. The 3D cornea center estimation module 716 may then check to see whether the corneal sphere 814a would properly reflect light from the light source 326 to the glint position 854. As shown in FIG. 8C, the first position is not a match as the ray 860a does not intersect light source 326.

Figure 8D:
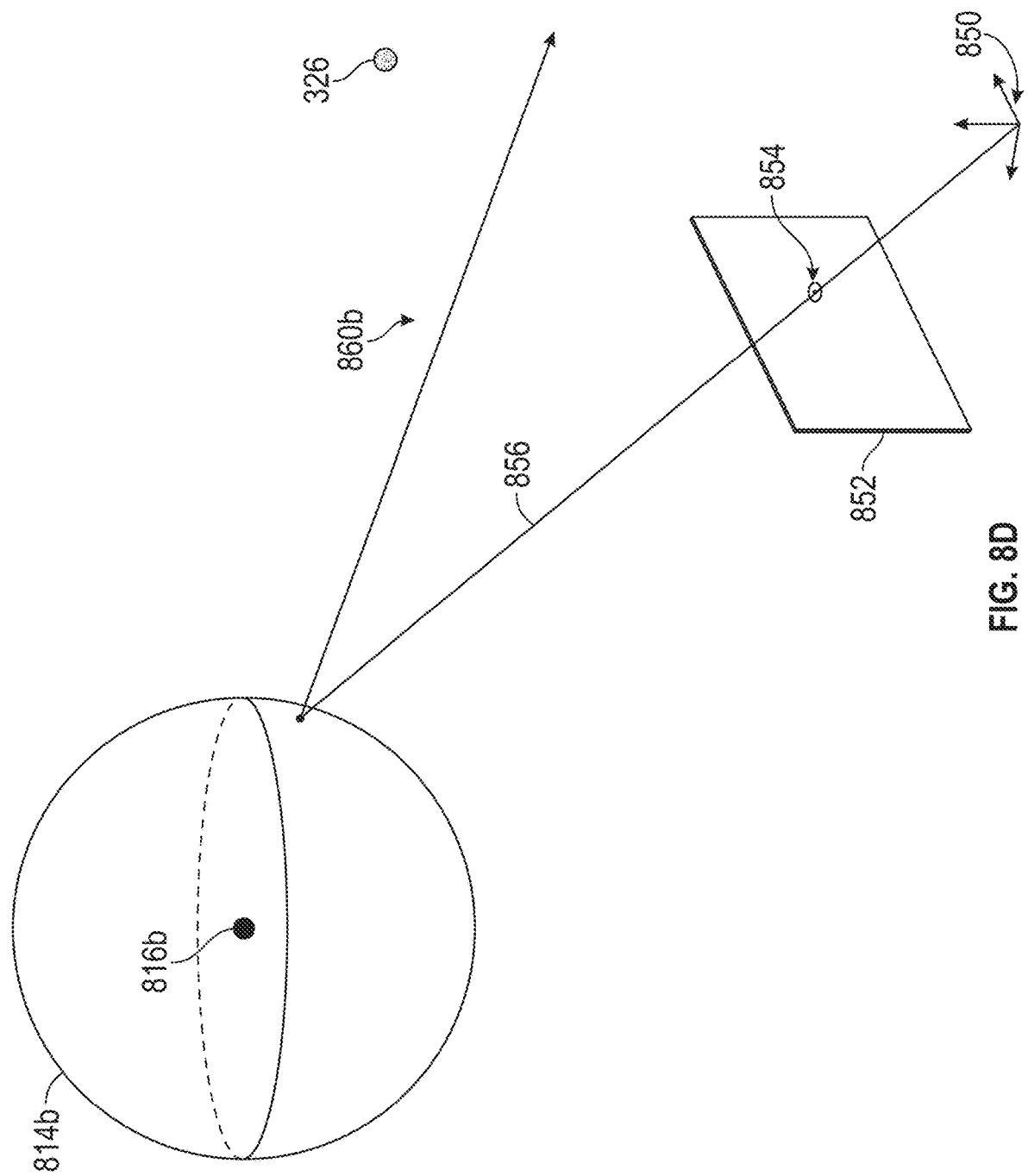

Similarly in FIG. 8D, 3D cornea center estimation module 716 simulates a corneal sphere 814b and corneal curvature center 816b at a second position. The 3D cornea center estimation module 716 then checks to see whether the corneal sphere 814b properly reflects light from the light source 326 to the glint position 854. As shown in FIG. 8D, the second position is also not a match.

As shown in FIG. 8E, the 3D cornea center estimation module 716 eventually is able to determine the correct position of the corneal sphere is corneal sphere 814c and corneal curvature center 816c. The 3D cornea center estimation module 716 confirms the illustrated position is correct by checking that light from source 326 will properly reflect off of the corneal sphere and be imaged by camera 324 at the correct location of glint 854 on image 852. With this arrangement and with the known 3D positions of the light source 326, the camera 324, and the optical properties of the camera (focal length, etc.), the 3D cornea center estimation module 716 may determine the 3D location of the cornea's center of curvature 816 (relative to the wearable system).

The processes described herein in connection with at least FIGS. 8C-8E may effectively be an iterative, repetitious, or optimization process to identify the 3D position of the user's cornea center. As such, any of a plurality of techniques (e.g., iterative, optimization techniques, etc.) may be used to efficiently and quickly prune or reduce the search space of possible positions. Moreover, in some embodiments, the system may include two, three, four, or more light sources such as light source 326 and some of all of these light sources may be disposed at different positions, resulting in multiple glints such as glint 854 located at different positions on image 852 and multiple rays such as ray 856 having different origins and directions. Such embodiments may enhance the accuracy of the 3D cornea center estimation module 716, as the module 716 may seek to identify a cornea position that results in some or all of the glints & rays being properly reflected between their respective light sources and their respective positions on image 852. In other words and in these embodiments, the positions of some or all of the light sources may be relied upon in the 3D cornea position determination (e.g., iterative, optimization techniques, etc.) processes of FIGS. 8B-8E.

Example of Normalizing the Coordinate System of Eye Tracking Images

Figure 9B:
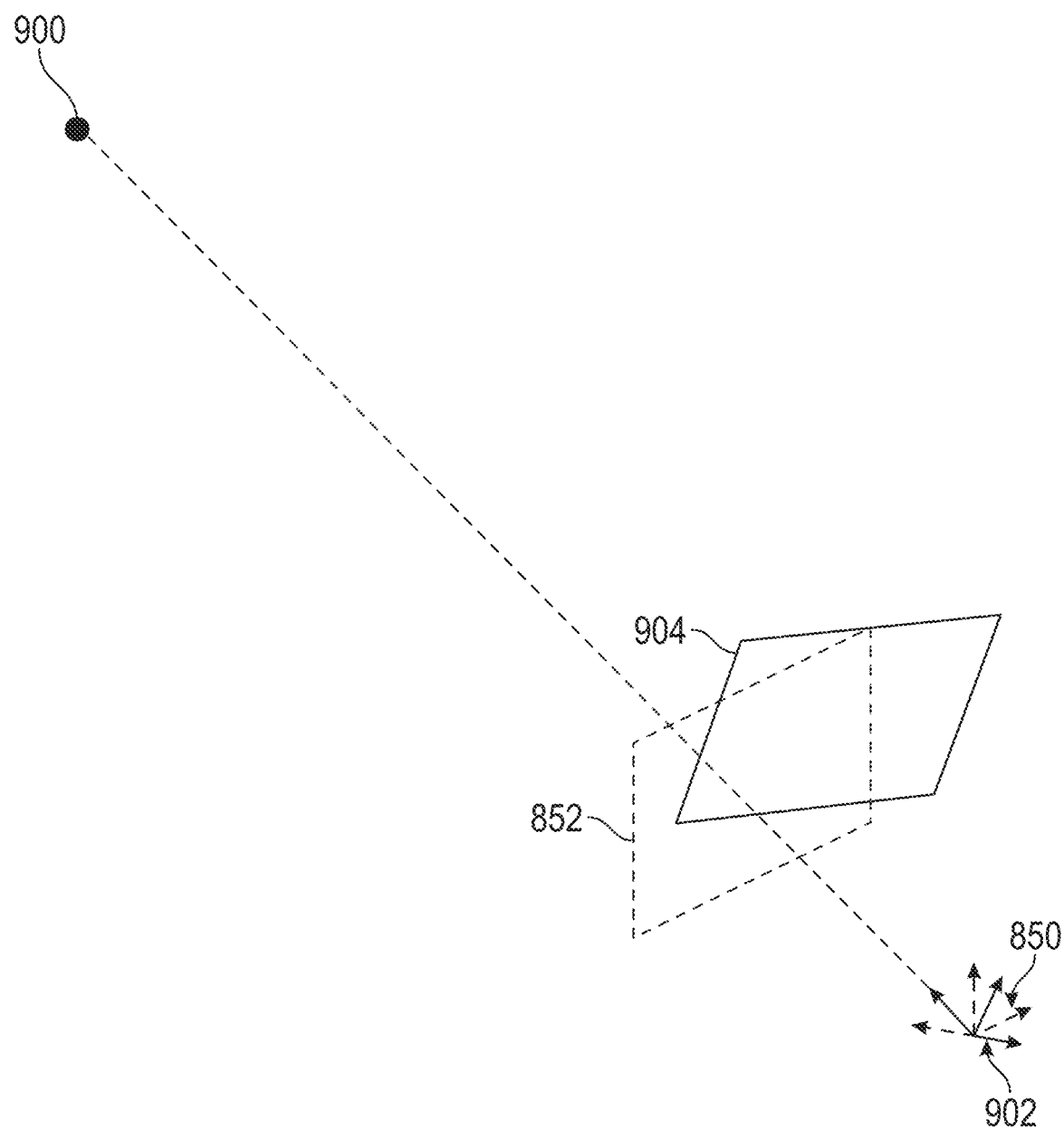
Figure 9C:
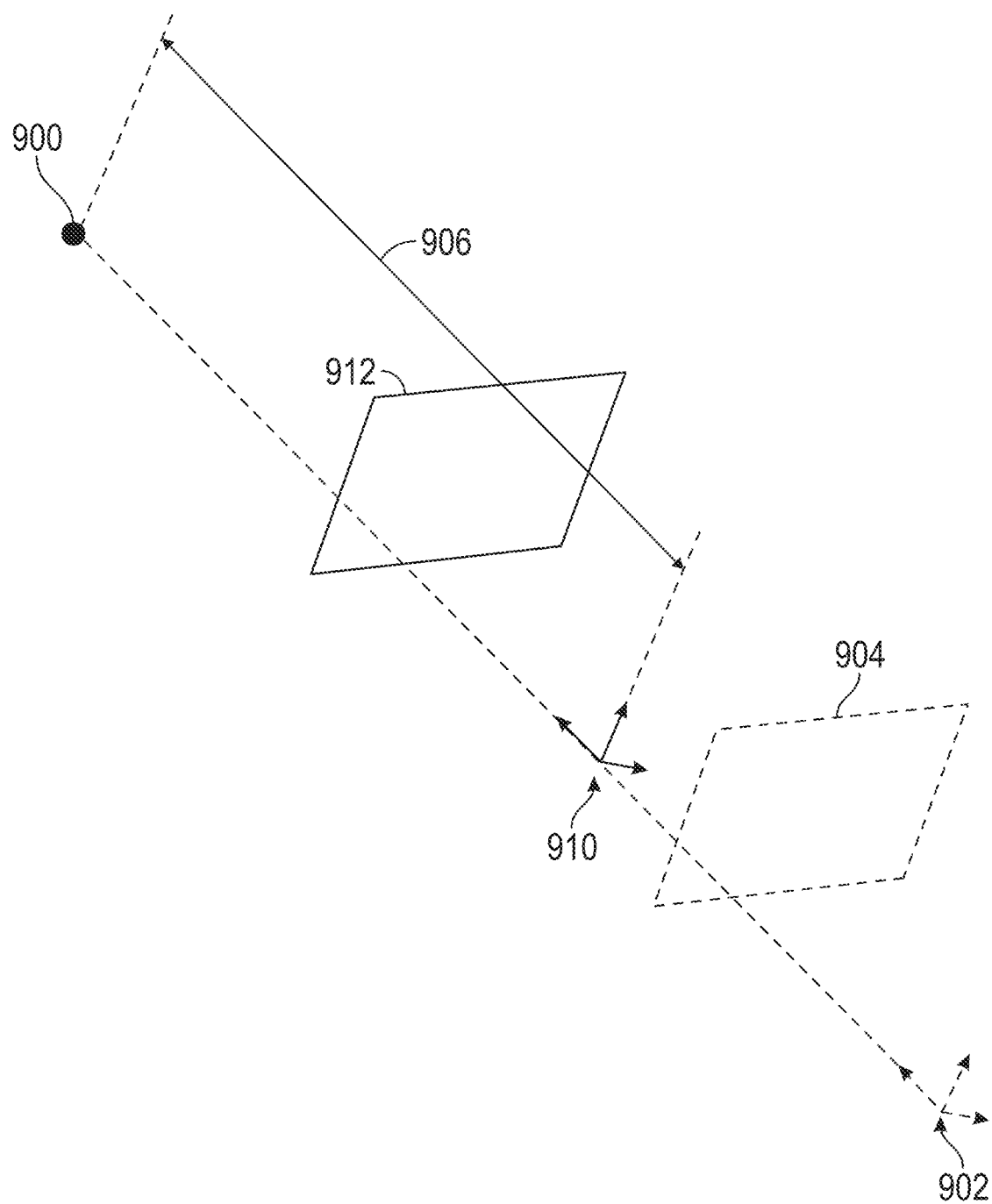

FIGS. 9A-9C illustrate an example normalization of the coordinate system of eye tracking images, by a component in the wearable system such as coordinate system normalization module 718 of FIG. 7A. Normalizing the coordinate system of eye tracking images relative to a user's pupil location may compensate for slippage of the wearable system relative to a user's face (i.e., headset slippage) and such normalization may establish a consistent orientation and distance between eye tracking images and a user's eyes.

As shown in FIG. 9A, coordinate system normalization module 718 may receive estimated 3D coordinates 900 of a user's center of corneal rotation and may receive un-normalized eye tracking images such as image 852. Eye tracking image 852 and coordinates 900 may be in an un-normalized coordinate system 850 that is based on the location of eye-tracking camera 324, as an example.

As a first normalization step, coordinate system normalization module 718 may rotate coordinate system 850 into rotated coordinate system 902, such that the z-axis (i.e., the vergence depth axis) of the coordinate system may be aligned with a vector between the origin of the coordinate system and cornea center of curvature coordinates 900, as shown in FIG. 9B. In particular, coordinate system normalization module 718 may rotate eye tracking image 850 into rotated eye tracking image 904, until the coordinates 900 of the user's corneal center of curvature are normal to the plane of the rotated image 904.

As a second normalization step, coordinate system normalization module 718 may translate rotated coordinate system 902 into normalized coordinate system 910, such that cornea center of curvature coordinates 900 are a standard, normalized distance 906 from the origin of normalized coordinate system 910, as shown in FIG. 9C. In particular, coordinate system normalization module 718 may translate rotated eye tracking image 904 into normalized eye tracking image 912. In at least some embodiments, the standard, normalized distance 906 may be approximately 30 millimeters. If desired, the second normalization step may be performed prior to the first normalization step.

Example of Locating a User's Pupil Centroid with an Eye Tracking System

FIGS. 9D-9G illustrate an example of locating a user's pupil center (i.e., the center of a user's pupil 822 as shown in FIG. 8A) using 3D pupil center locator module 720 and eye tracking module 614.

Figure 9D:
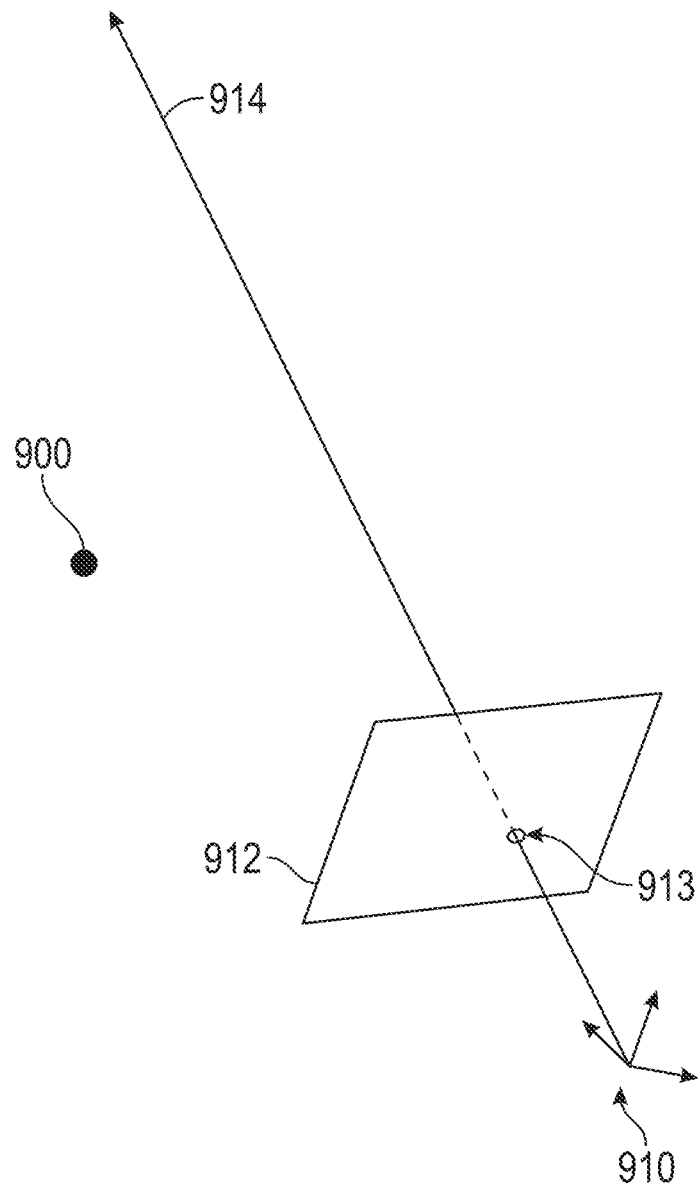
FIGS. 9D-9G illustrate example stages of locating a user's pupil center with an eye tracking module in a wearable system.

As shown in FIG. 9D, 3D pupil center locator module 720 may receive a normalized eye tracking image 912 that includes a pupil centroid 913 (i.e., a center of a user's pupil as identified by pupil identification module 712). The 3D pupil center locator module 720 may then simulate the normalized 3D position 910 of eye camera 324 to cast a ray 914 in the normalized coordinate system 910, through the pupil centroid 913.

Figure 9E:
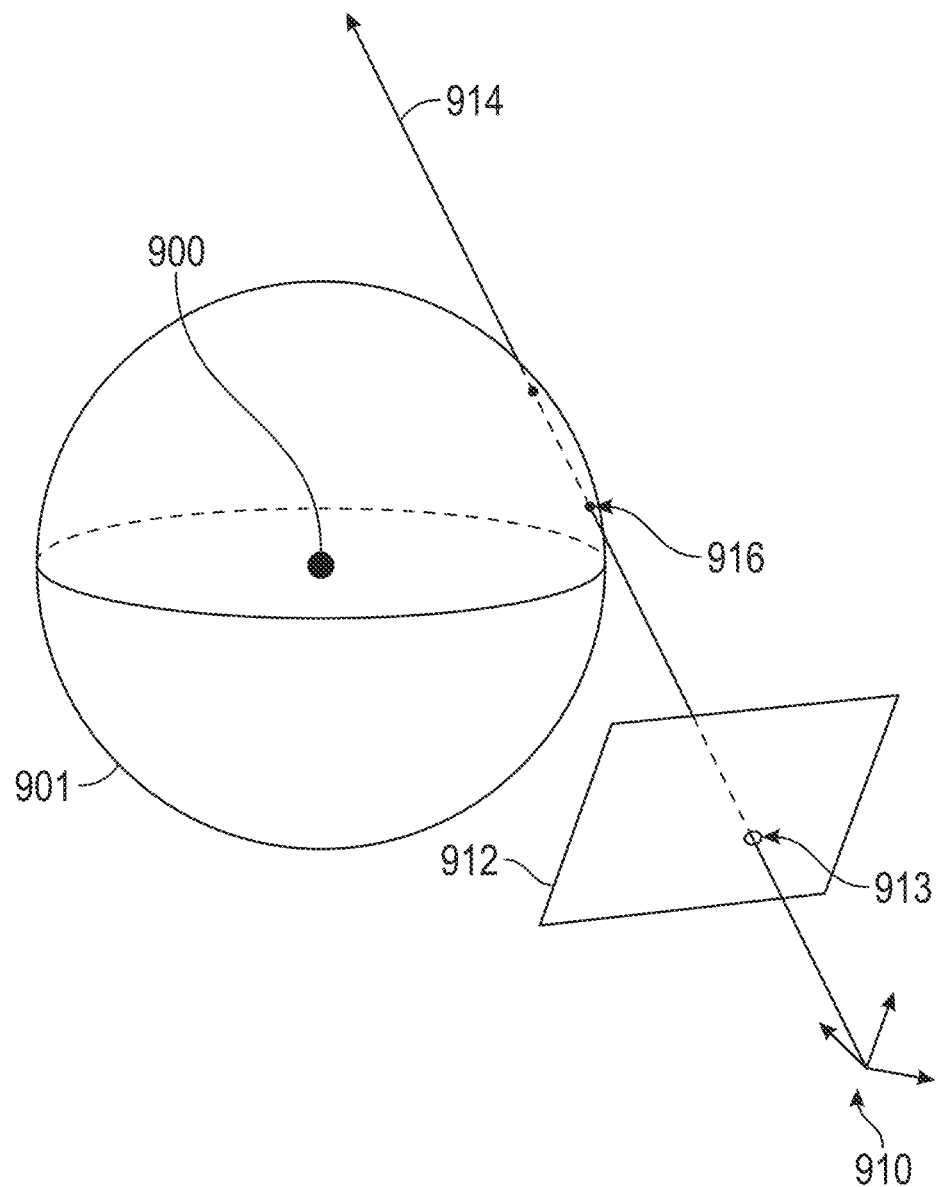

In FIG. 9E, 3D pupil center locator module 720 may simulate a corneal sphere such as corneal sphere 901 having center of curvature 900 based on data from 3D cornea center estimation module 716 (and as discussed in more detail in connection with FIGS. 8B-8E). As an example, the corneal sphere 901 may be positioned in the normalized coordinate system 910 based on the location of the center of curvature 816c identified in connection with FIG. 8E and based on the normalization processes of FIGS. 9A-9C. Additionally, 3D pupil center locator module 720 may identify a first intersection 916 between ray 914 (i.e., a ray between the origin of normalized coordinate system 910 and the normalized location of a user's pupil) and the simulated cornea, as shown in FIG. 9E.

Figure 9F:
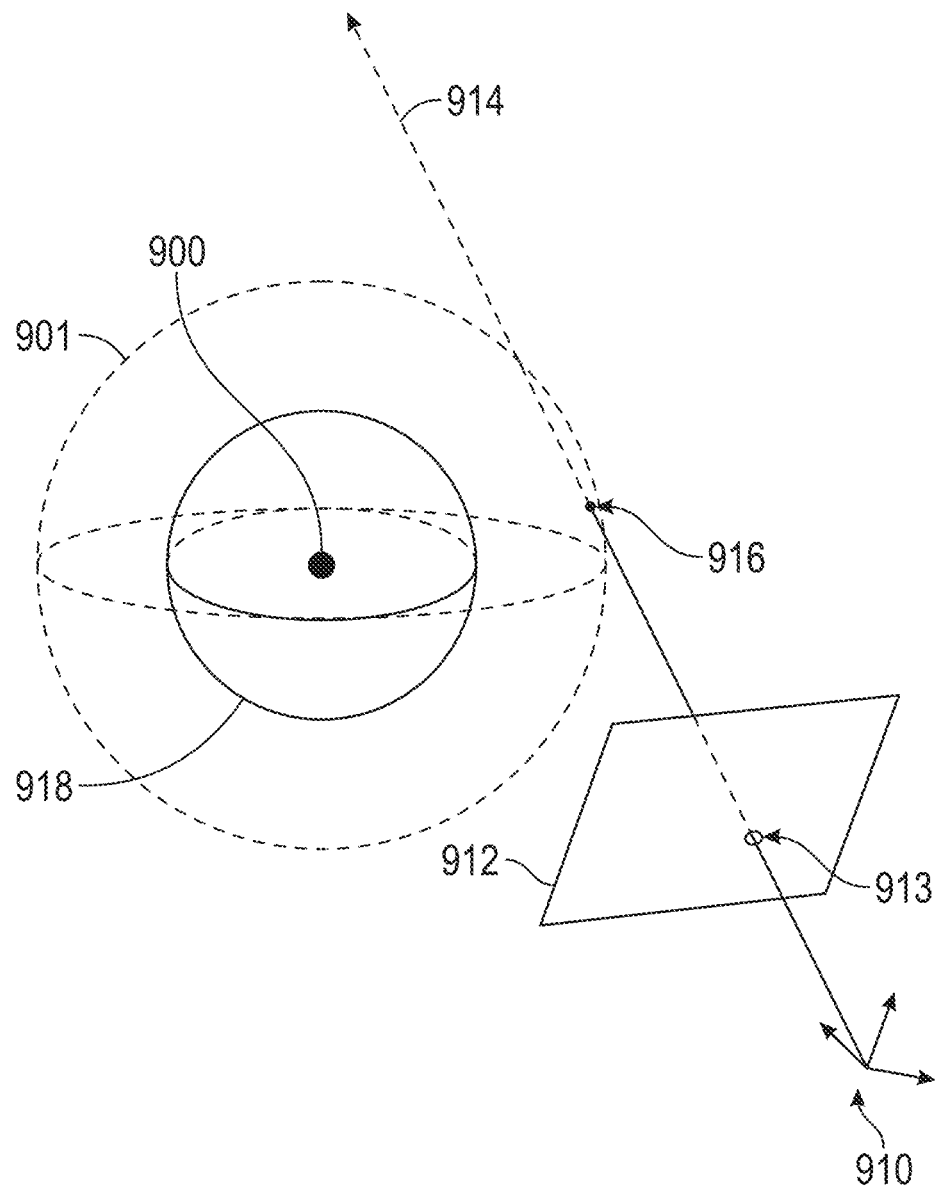

As shown in FIG. 9F, 3D pupil center locator module 720 may determine pupil sphere 918 based on corneal sphere 901. Pupil sphere 918 may share a common center of curvature with corneal sphere 901, but have a small radius. 3D pupil center locator module 720 may determine a distance between cornea center 900 and pupil sphere 918 (i.e., a radius of pupil sphere 918) based on a distance between the corneal center and the pupil center. In some embodiments, the distance between a pupil center and a corneal center of curvature may be determined from assumed eye dimensions 704 of FIG. 7A, from eye tracking extrinsics and intrinsics database 702, and/or from per-user calibration data 706. In other embodiments, the distance between a pupil center and a corneal center of curvature may be determined from per-user calibration data 706 of FIG. 7A.

Figure 9G:
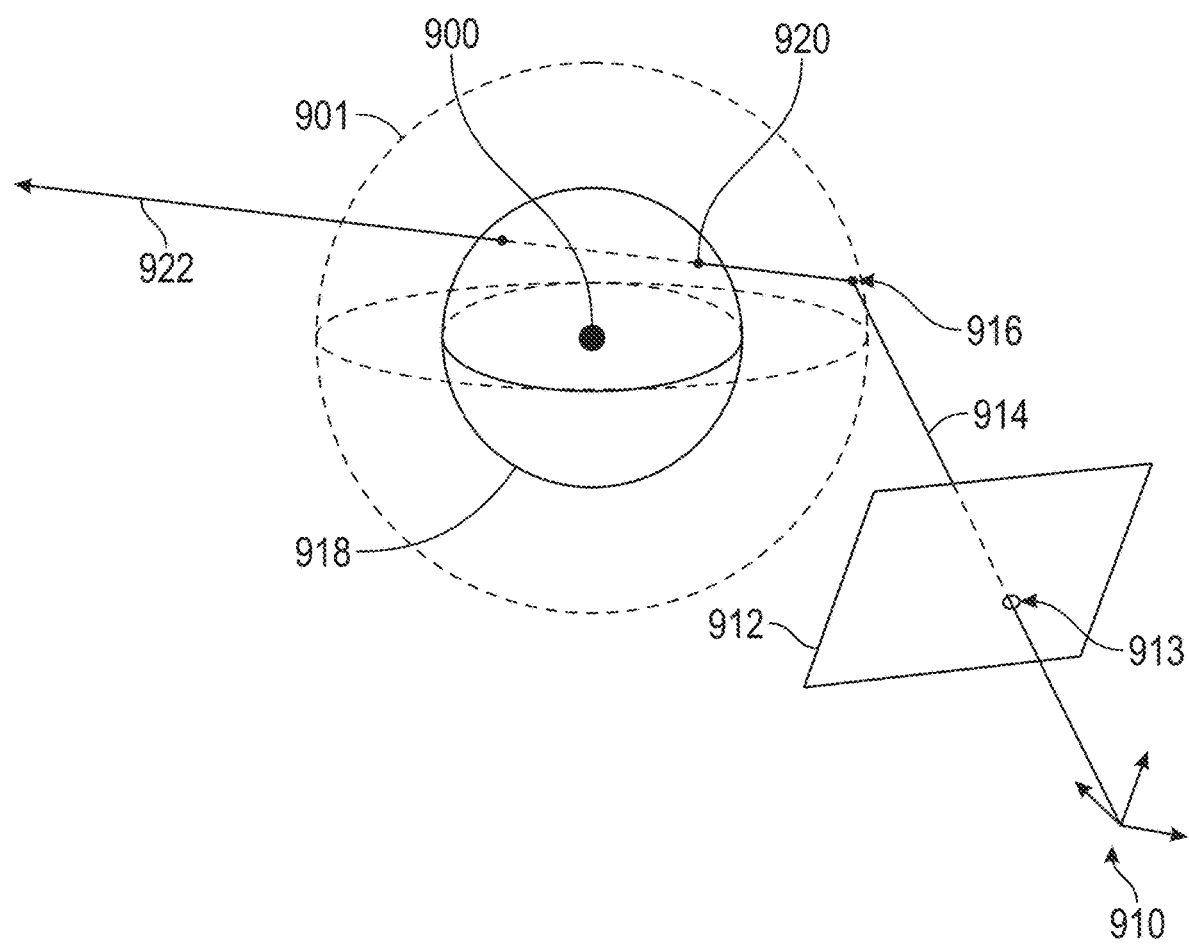

As shown in FIG. 9G, 3D pupil center locator module 720 may locate the 3D coordinates of a user's pupil center based on variety of inputs. As examples, the 3D pupil center locator module 720 may utilize the 3D coordinates and radius of the pupil sphere 918, the 3D coordinates of the intersection 916 between a simulated cornea sphere 901 and a ray 914 associated with a pupil centroid 913 in a normalized eye tracking image 912, information on the index of refraction of a cornea, and other relevant information such as the index of refraction of air (which may be stored in eye tracking extrinsics & intrinsics database 702) to determine the 3D coordinates of the center of a user's pupil. In particular, the 3D pupil center locator module 720 may, in simulation, bend ray 916 into refracted ray 922 based on refraction difference between air (at a first index of refraction of approximately 1.00) and corneal material (at a second index of refraction of approximately 1.38). After taking into account refraction caused by the cornea, 3D pupil center locator module 720 may determine the 3D coordinates of the first intersection 920 between refracted ray 922 and pupil sphere 918. 3D pupil center locator module 720 may determine that a user's pupil center 920 is located at approximately the first intersection 920 between refracted ray 922 and pupil sphere 918. With this arrangement, the 3D pupil center locator module 720 may determine the 3D location of the pupil center 920 (relative to the wearable system), in the normalized coordinate system 910. If desired, the wearable system may un-normalize the coordinates of the pupil center 920 into the original eye camera coordinate system 850. The pupil center 920 may be used together with the corneal curvature center 900 to determine, among other things, a user's optical axis using optical axis determination module 722 and a user's vergence depth by vergence depth estimation module 728.

Example of Differences Between Optical and Visual Axes

Figure 10:
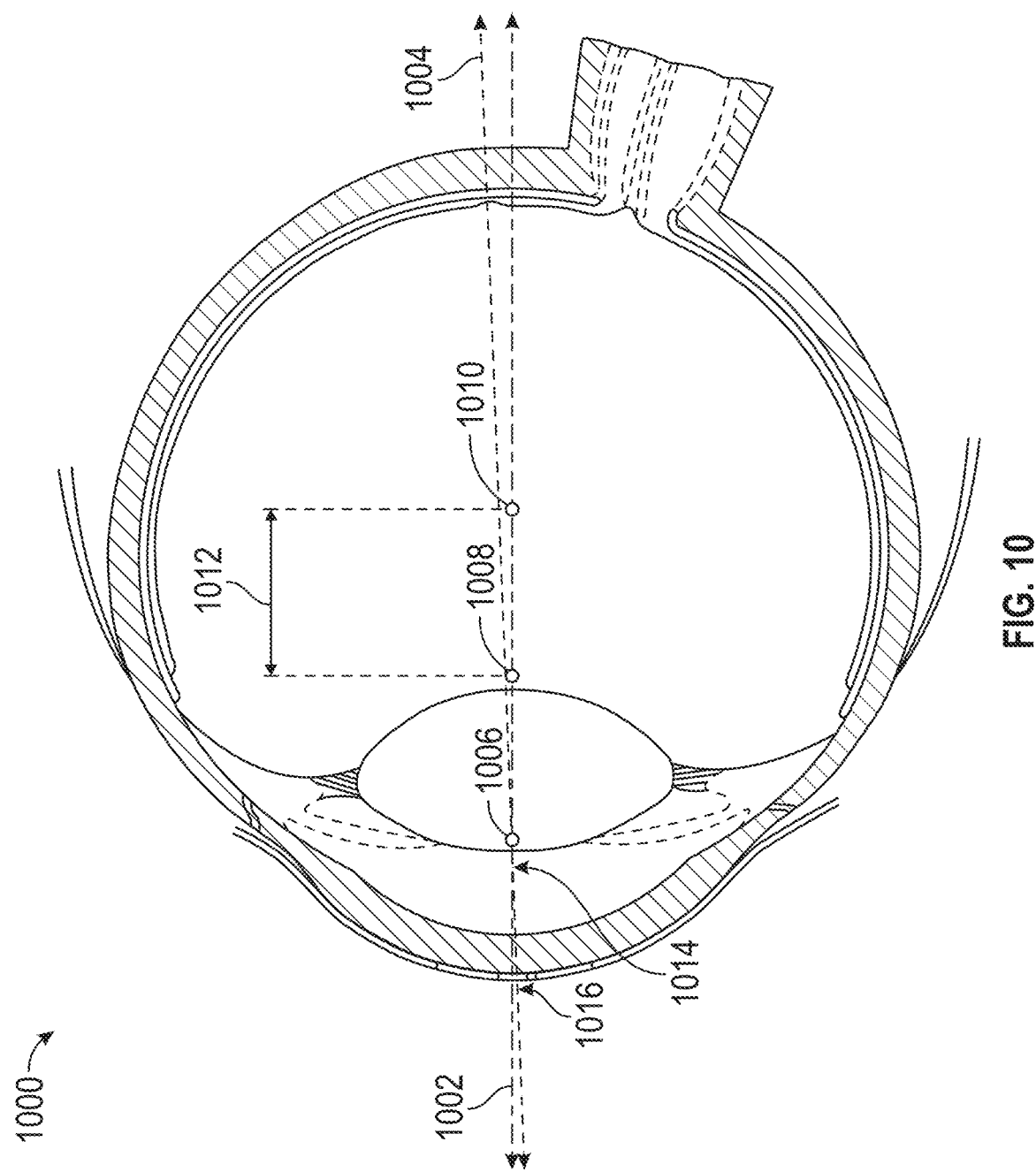
FIG. 10 illustrates an example of an eye including the eye's optical and visual axes and the eye's center of rotation.

As discussed in connection with optical to visual mapping module 730 of FIG. 7A, a user's optical and visual axes are generally not aligned, due in part to a user's visual axis being defined by their fovea and that foveae are not generally in the center of a person's retina. Thus, when a person desires to concentrate on a particular object, the person aligns their visual axis with that object to ensure that light from the object falls on their fovea while their optical axis (defined by the center of their pupil and center of curvature of their cornea) is actually slightly offset from that object. FIG. 10 is an example of an eye 1000 illustrating the eye's optical axis 1002, the eye's visual axis 1004, and the offset between these axes. Additionally, FIG. 10 illustrates the eye's pupil center 1006, the eye's center of cornea curvature 1008, and the eye's average center of rotation (CoR) 1010. In at least some populations, the eye's center of cornea curvature 1008 may lie approximately 4.7 mm in front, as indicated by dimension 1012, of the eye's average center of rotation (CoR) 1010. Additionally, the eye's center of perspective 1014 may lie approximately 5.01 mm in front of the eye's center of cornea curvature 1008, about 2.97 mm behind the outer surface 1016 of the user's cornea, and/or just in front of the user's pupil center 1006 (e.g., corresponding to a location within the anterior chamber of eye 1000). As additional examples, dimension 1012 may between 3.0 mm and 7.0 mm, between 4.0 and 6.0 mm, between 4.5 and 5.0 mm, or between 4.6 and 4.8 mm or any ranges between any values and any values in any of these ranges. The eye's center of perspective (CoP) 1014 may be a useful location for the wearable system as, in at least some embodiments, registering a render camera at the CoP may help to reduce or eliminate parallax artifacts.

FIG. 10 also illustrates such a within a human eye 1000 with which the pinhole of a render camera may be aligned. As shown in FIG. 10, the pinhole of a render camera may be registered with a location 1014 along the optical axis 1002 or visual axis 1004 of the human eye 1000 closer to the outer surface of the cornea than both (a) the center of the pupil or iris 1006 and (b) the center of cornea curvature 1008 of the human eye 1000. For example, as shown in FIG. 10, the pinhole of a render camera may be registered with a location 1014 along the optical axis 1002 of the human eye 1000 that is about 2.97 millimeters rearward from the outer surface of the cornea 1016 and about 5.01 millimeters forward from the center of cornea curvature 1008. The location 1014 of the pinhole of the render camera and/or the anatomical region of the human eye 1000 to which the location 1014 corresponds may be seen as representing the center of perspective of the human eye 1000. The optical axis 1002 of the human eye 1000 as shown in FIG. 10 represents the most direct line through the center of cornea curvature 1008 and the center of the pupil or iris 1006. The visual axis 1004 of the human eye 1000 differs from the optical axis 1002, as it represents a line extending from the fovea of the human eye 1000 to the center of the pupil or iris 1006.

Figure 11:
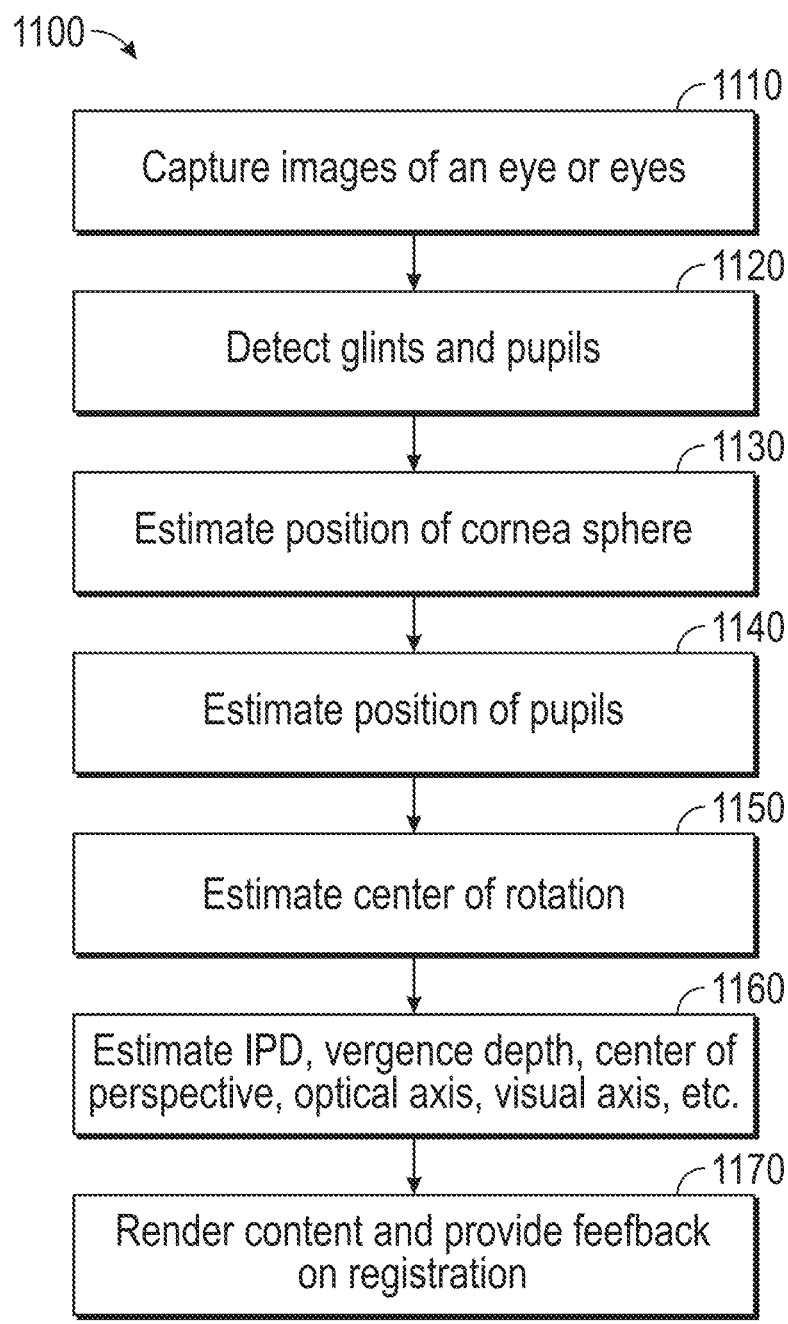
FIG. 11 is a process flow diagram of an example of a method for using eye tracking in rendering content and providing feedback on registration in a wearable device.

Example Processes of Rendering Content and Checking Registration Based on Eye Tracking FIG. 11 is a process flow diagram of an example method 1100 for using eye tracking in rendering content and providing feedback on registration in a wearable device. The method 1100 may be performed by the wearable system described herein. Embodiments of the method 1100 may be used by the wearable system to render content and provide feedback on registration (i.e., fit of the wearable device to the user) based on data from an eye tracking system.

At block 1110, the wearable system may capture images of a user's eye or eyes. The wearable system may capture eye images using one or more eye cameras 324, as shown at least in the example of FIG. 3. If desired, the wearable system may also include one or more light sources 326 configured to shine IR light on a user's eyes and produce corresponding glints in the eye images captured by eye cameras 324. As discussed herein, the glints may be used by an eye tracking module 614 to derive various pieces of information about a user's eye including where the eye is looking.

At block 1120, the wearable system may detect glints and pupils in the eye images captured in block 1110. As an example, block 1120 may include processing the eye images by glint detection & labeling module 714 to identify the two-dimensional positions of glints in the eye images and processing the eye images by pupil identification module 712 to identify the two-dimensional positions of pupils in the eye images.

At block 1130, the wearable system may estimate the three-dimensional positions of a user's left and right corneas relative to the wearable system. As an example, the wearable system may estimate the positions of the center of curvature of a user's left and right corneas as well as the distances between those centers of curvature and the user's left and right corneas. Block 1130 may involve 3D cornea center estimation module 716 identifying the position of the centers of curvature as described herein at least in connection with FIGS. 7A and 8A-8E.

At block 1140, the wearable system may estimate the three-dimensional positions of a user's left and right pupil centers relative to the wearable system. As an example, the wearable system and 3D pupil center locator module 720 in particular, may estimate the positions of the user's left and right pupil centers as described at least in connection with FIGS. 7A and 9D-9G, as part of block 1140.

At block 1150, the wearable system may estimate the three-dimensional positions of a user's left and right centers or rotation (CoR) relative to the wearable system. As an example, the wearable system and CoR estimation module 724 in particular, may estimate the positions of the CoR for the user's left and right eyes as described at least in connection with FIGS. 7A and 10. As a particular example, the wearable system may find the CoR of an eye by walking back along the optical axis from the center of curvature of a cornea towards the retina.

At block 1160, the wearable system may estimate a user's IPD, vergence depth, center of perspective (CoP), optical axis, visual axis, and other desired attributes from eye tracking data. As examples, IPD estimation module 726 may estimate a user's IPD by comparing the 3D positions of the left and right CoRs, vergence depth estimation module 728 may estimate a user's depth by finding an intersection (or near intersection) of the left and right optical axes or an intersection of the left and right visual axes, optical axis determination module 722 may identify the left and right optical axes over time, optical to visual axis mapping module 730 may identify the left and right visual axes over time, and the CoP estimation module 732 may identify the left and right centers of perspective, as part of block 1160.

At block 1170, the wearable system may render content and may, optionally, provide feedback on registration (i.e., fit of the wearable system to the user's head) based in part on the eye tracking data identified in blocks 1120-1160. As an example, the wearable system may identify a suitable location for a render camera and then generate content for a user based on the render camera's location, as discussed in connection with light-field render controller 618, FIG. 7B, and render engine 622. As another example, the wearable system may determine if it is properly fitted to the user, or has slipped from its proper location relative to the user, and may provide optional feedback to the user indicating whether the fit of the device needs adjustment, as discussed in connection with registration observer 620 and as discussed in connection with block 1608 of FIG. 16. In some embodiments, the wearable system may adjust rendered content based on improper or less than ideal registration in an attempt to reduce, minimize or compensate for the effects of improper or mis-registration, as discussed in connection with block 1610 of FIG. 16.

Overview of Device Registration

In order for the wearable system 200 described herein to output images of high perceived image quality, the display 220 of the wearable system 200 (FIG. 2) is preferably properly fitted to a user (e.g., positioned and oriented with respect to the user's head such that the inputs and outputs of system 200 interface appropriately with corresponding portions of the user's head and such that the device is stable and comfortable to wear and use). As an example, for display 220 to provide visual content to a user's eyes, the display 220 is preferably situated in front of the user's eyes and, depending on the relevant properties of the display 220, the user's eyes are preferably situated in a particular volume (see, e.g., the further discussion associated with FIGS. 13A and 13B). As additional examples, the speaker 240 is preferably situated near, on, or in the user's ears to provide high-quality audio content to the user, audio sensor (e.g., a microphone) 232 is preferably situated in a particular area to receive sound from the user, and inward-facing imaging system 462 (which may include one or more cameras 324 and one or more infrared light sources 326) is preferably properly situated in a position and orientation to obtain clear, unobstructed images of a user's eyes (which may be part of an eye tracking system). These are merely examples of various reasons why wearable system 200 are preferably properly fitted to users.

In order to ensure the wearable system 200 is properly registered to a user, the wearable system 200 may include a registration observer such as registration observer 620 of FIG. 6. In some embodiments, the properly registered wearable system 200 includes a display that is positioned so that one or more eyes of the user are able to receive sufficient image light to see substantially the entirety of the field of view provided by the display 220 of the wearable display system 200. For example, a properly registered display may allow an image to be seen across about 80% or more, about 85% or more, about 90% or more, or about 95% or more of the field of view of the display with a brightness uniformity of 80% or more, about 85% or more, about 90% or more, or about 95% or more. It will be appreciated that the brightness uniformity may be equal to 100% times the minimum luminance divided by the maximum luminance across the entirety of the field of view of the display ($100\% \times L_{min}/L_{max}$), when the display is displaying the same content throughout the field of view.

The registration observer 620 may determine how the wearable system 200 is fitted on the user (e.g., if the display 220 of the wearable system 200 is positioned on the user properly) using various sensors. As an example, the registration observer 620 may use an inward-facing imaging system 462, which may include an eye tracking system, to determine how relevant parts of the wearable system 200 are spatially oriented with respect to the user and, in particular, the user's eyes, ears, mouth, or other parts that interface with the wearable system 200.

The registration observer 620 may assist with a calibration process, such an initial or subsequent configuration or setup of the wearable system 200 for a particular user. As an example, registration observer 620 may provide feedback to a user during configuration or setup of the wearable system 200 for that particular user. Additionally or alternatively, the registration observer 620 may continuously, or intermittently, monitor registration of the wearable system 200 on a user to check for continued proper registration during use and may provide user feedback on the fly. Registration observer 620 may provide user feedback, either as part of a configuration process or as part of registration monitoring during use, that indicates when the wearable system 200 is properly registered and when the wearable system 200 is not properly registered. The registration observer 620 may also provide particular recommendations for how the user may correct any misregistration and achieve proper registration. As examples, the registration observer 620 may recommend the user to push the wearable device back up after detecting slippage of the wearable device (such as down the user's nasal bridge), may recommend that the user adjust some adjustable component of the wearable device (e.g., as described herein in connection with FIGS. 15A and 15B), etc.

Example of a Registration Coordinate System

Figure 12A:
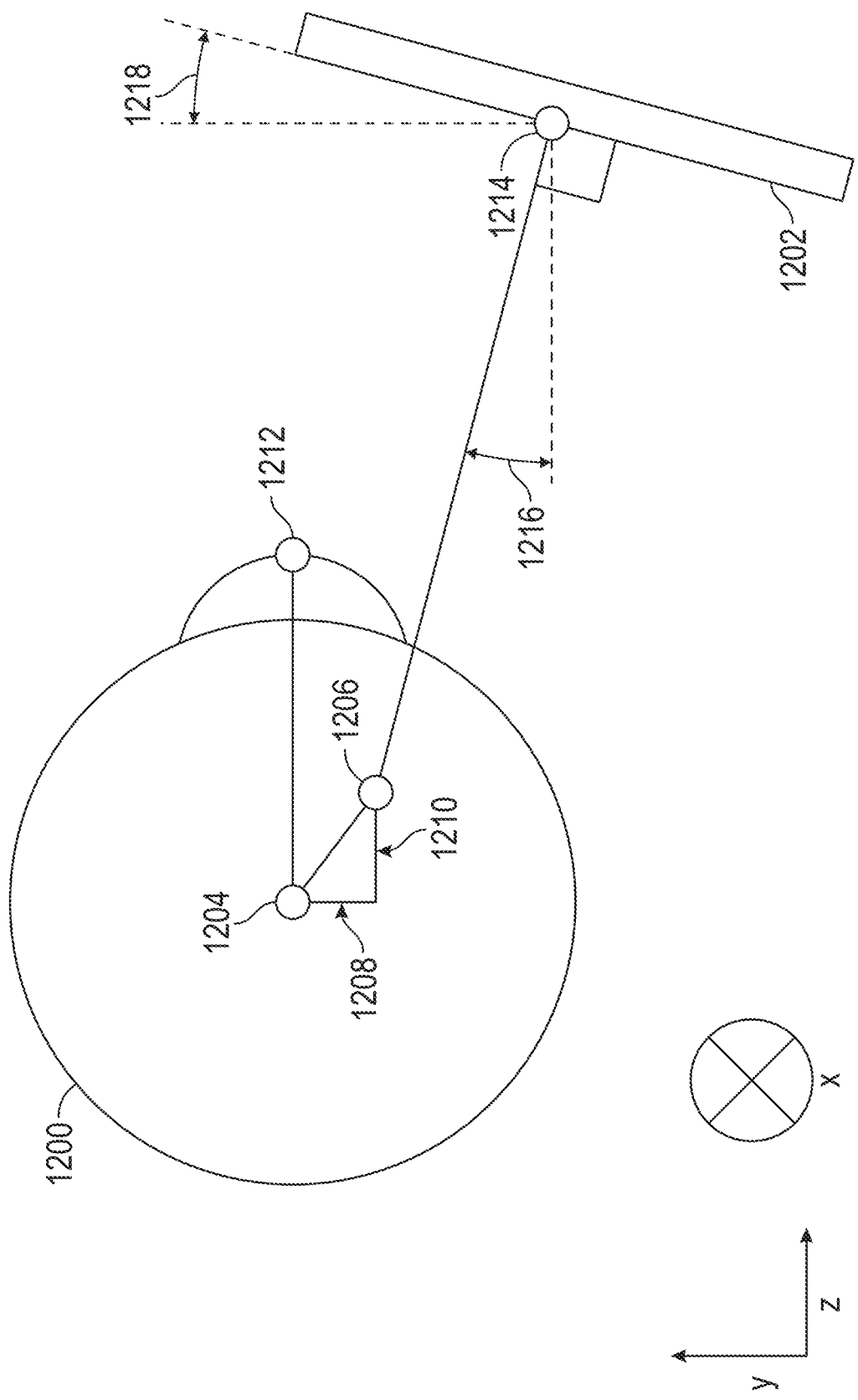

FIGS. 12A-12B illustrate an example eye position coordinate system, which may be used for defining three-dimensional positions of a user's left and right eyes relative to the display of the wearable system described herein. As examples, the coordinate system may include axis x, y, and z. Axis z of the coordinate system may correspond to depth, such the distance between the plane a user's eyes lie in and the plane that display 220 lies in (e.g., the direction normal to the plane of the front of a user's face). Axis x of the coordinate system may correspond to a left-right direction, such as the distance between the users left and right eyes. Axis y of the coordinate system may correspond to an up-down direction, which may be a vertical direction when the user is upright.

FIG. 12A illustrates a side view of a user's eye 1200 and a display surface 1202 (which may be a part of display 220 of FIG. 2), while FIG. 12B illustrates a top down view of the user's eye 1200 and the display surface 1202. Display surface 1202 may be located in front of the user's eyes and may output image light to the user's eyes. As an example, display surface 1202 may comprise one or more out-coupling light elements, active or pixel display elements, and may be part of a stack of waveguides, such as stacked waveguide assembly 480 of FIG. 4. In some embodiments, the display surface 1202 may be planar. In some other embodiments, the display surface 1202 may have other topologies (e.g., be curved). It will be appreciated that the display surface 1202 may be a physical surface of the display, or simply a plane or other imaginary surface from which image light is understood to propagate from the display 220 to the user's eyes.

As shown in FIG. 12A, the user's eye 1200 may have an actual position 1204 offset from a nominal position 1206 and the display surface 1202 may be at position 1214. FIG. 12A also illustrates the corneal apex 1212 of the user's eye 1200. The user's line of sight (e.g., their optical and/or visual axis) may be substantially along the line between the actual position 1204 and the corneal apex 1212. As shown in FIGS. 12A and 12B, the actual position 1204 may be offset from the nominal position 1206 by an z-offset 1210, a y-offset 1208, and an x-offset 1209. The nominal position 1206 may represent a preferred position (sometimes referred to as a design position, which may be generally centered within a desired volume) for the user's eye 1200 with respect to the display surface 1202. As the user's eye 1200 moves away from the nominal position 1206, the performance of display surface 1202 may be degraded, as discussed herein in connection with FIG. 14 for example.

In addition, it will be appreciated that the default position for a render camera may be the nominal position 1206. As discussed herein, the display system may be configured to render content from the perspective of the imaginary render camera. As a result, various parameters of the render camera, e.g., focal length, may impact the appearance of content provided to the user. For example, the focal length may determine the magnification and size of virtual content presented to the user. Thus, different focal lengths may be associated with different depth planes.

In some embodiments, the lens of the render camera may be positioned at the nominal position 1206 as a default, with the nominal position 1206 assumed to correspond to the center of rotation, which may be understood to be the point 1204 in this example. However, offsets of the center of rotation 1204 from the nominal position 1206 may cause undesirable viewer discomfort. For example, it will be appreciated that magnification errors can occur on a per-eye basis and virtual content may appear larger or smaller than intended. In one scenario, if the focal length of the render camera is shorter than expected (e.g., as a result of the center of rotation of the user's eye being positioned behind the nominal position, but without compensating for this displacement or offset in render space), then virtual content may appear smaller than intended. Similarly, if the focal length of the render camera is longer than expected (e.g., as a result of the center of rotation of the user's eye being positioned in front the nominal position, but without compensating for this displacement or offset in render space), then virtual content may appear larger than intended. If such magnification errors are different for each eye (e.g., as a result of the center of rotation of the one eye being positioned behind the nominal position and the center of rotation of the user's other eye being positioned in front of the nominal position, without proper compensation of these offsets in render space), the perceived size of the same virtual object may differ from eye-to-eye. This difference in size may cause the user to experience some level of discomfort (e.g., potential eye strain and/or headache from trying to reconcile binocular size discrepancies).

In some embodiments, the focal length of the render camera may be determined based upon the z-axis offset between the default position 1206 (the position assumed for the center of rotation) and the actual position of the center of rotation 1204. For example, if the center of rotation is positioned behind the nominal position, then the focal length of the render camera may be reduced (e.g., reduced by the offset amount). On the other hand, if the center of rotation is positioned in front of the nominal position, then the focal length may be increased (e.g., increased by the offset amount).

In addition, in some embodiments, the focal length of the render camera may also be calculated based upon the depth plane being used by the system. For example, in some embodiments, the optics of the render camera may be assumed to follow the thin lens equation ($1/o+1/i=1/f$), where o is the object distance (e.g., the depth plane on which content is being presented), i is a constant (e.g. the distance from the center of rotation to the user's retina), and f is the focal length. As discussed herein, the depth plane on which content is presented has a set distance from the user. As a result, since the quantities o and i are known, the focal length may be determined by solving for f. In some implementations, render camera focal length adjustments may be performed in connection with one or more operations described herein, such as step 1170, as described above with reference to FIG. 11, and step 1610, as described in further detail below with reference to FIG. 16. Examples of additional render camera adjustment schemes that may be employed by one or more of the systems described herein are provided in U.S. Patent Prov. App. 62/618,559, entitled "EYE CENTER OF ROTATION DETERMINATION, DEPTH PLANE SELECTION, AND RENDER CAMERA POSITIONING IN DISPLAY SYSTEMS" filed on Jan. 17, 2018 and U.S. Patent Prov. App. 62/702,849, entitled "EYE CENTER OF ROTATION DETERMINATION, DEPTH PLANE SELECTION, AND RENDER CAMERA POSITIONING IN DISPLAY SYSTEMS" and filed on Jul. 24, 2018, both of which are incorporated by reference herein in their entirety.

With continued reference to FIG. 12A, it will be appreciated that a point or volume associated with the user's eye 1200 may be used to represent the position of the user's eye in analyses of registration herein. The representative point or volume may be any point or volume associated with the eye 1200, and preferably is consistently used. For example, the point or volume may be on or in the eye 1200, or may be disposed away from the eye 1200. In some embodiments, the point or volume is the center of rotation of the eye 1200. The center of rotation may be determined as described herein and may have advantages for simplifying the registration analyses, since it is roughly symmetrically disposed on the various axes within the eye 1200 and allows a single display registration volume aligned with the optical axis to be utilized for the analyses.

FIG. 12A also illustrates that the display surface 1202 may be centered below the user's horizon (as seen along the y-axis when the user is looking straight ahead, with their optical axis parallel to the ground) and may be tilted (with respect to the y-axis). In particular, the display surface 1202 may be disposed somewhat below the user's horizon such that the user would have to look downward, at approximately the angle 1216, to look at the center of the display surface 1202, when the eye 1200 is at position 1206. This may facilitate a more natural and comfortable interaction with the display surface 1202, particularly when viewing content rendered at shorter depths (or distances from the user), as users may be more comfortable viewing content below their horizon than above their horizon. Additionally, display surface 1202 may be tilted, such as at angle 1218 (with respect to the y-axis) such that, when the user is looking at the center of the display surface 1202 (e.g., looking slightly below the user's horizon), the display surface 1202 is generally perpendicular to the user's line of sight. In at least some embodiments, the display surface 1202 may also be shifted left or right (e.g., along the x-axis)

relative to the nominal position of the user's eye. As an example, a left-eye display surface may be shifted rightwards and a right-eye display surface may be shifted leftwards (e.g., display surfaces 1202 may be shifted towards each other) such that the user's lines of sight hits the centers of the display surfaces when focused at some distance less than infinity, which may increase user comfort during typical usage on the wearable device.

Example of a Display Registration Volume

Figure 13B:
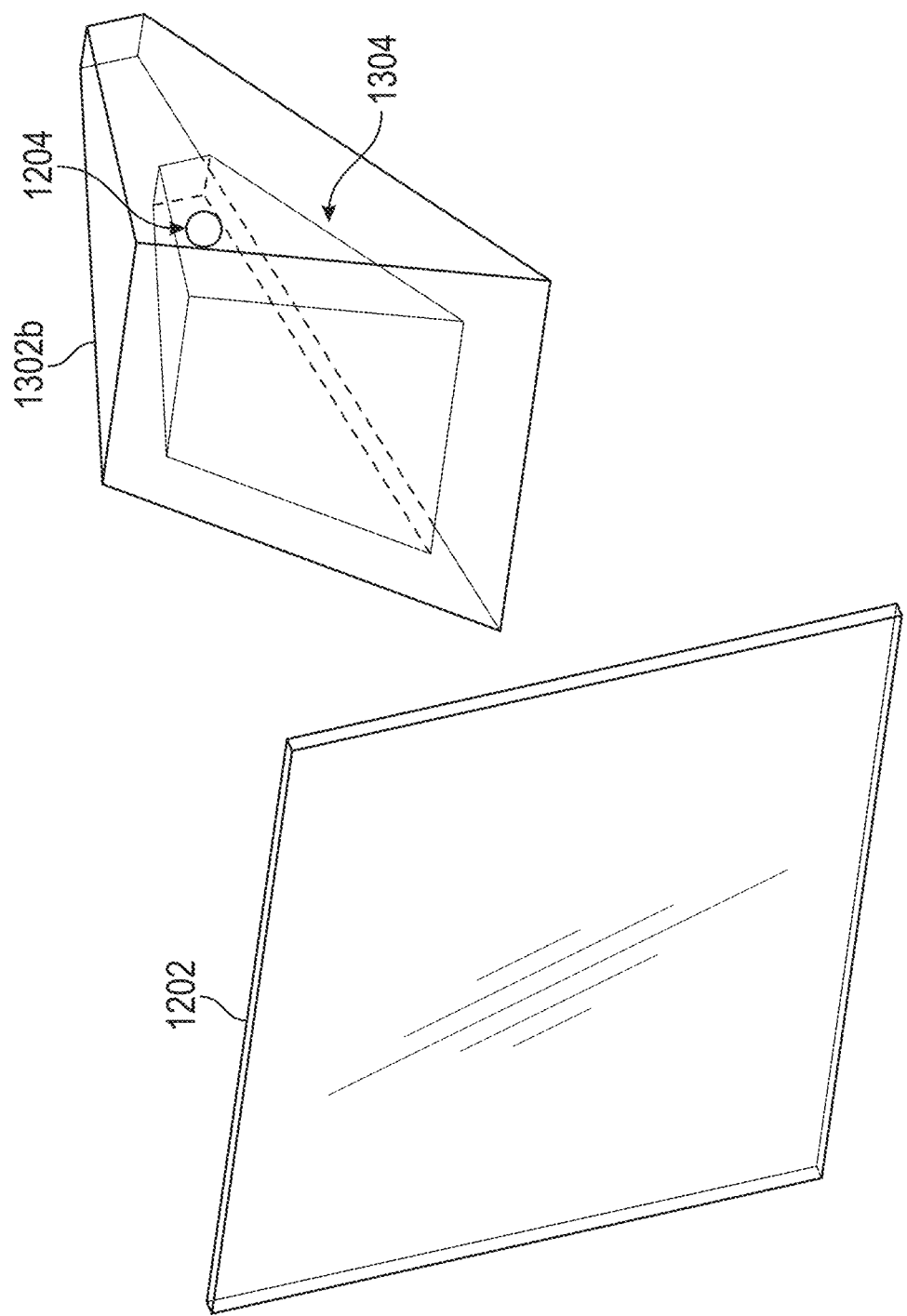

FIGS. 13A-13B illustrate an example display registration volume 1302*a*. The display registration volume 1302*a* may represent the spatial volume in which the eye 1200 is positioned so as to receive image light from the display device. In some embodiments, a center of rotation of a user's eye is preferably located so that the eye registers, or receives, image information from the display device. In some embodiments, when the center of rotation of the user's eyes is located within the display registration volume 1302*a*, the user is able to see the entirety of the image outputted by the display device with high brightness uniformity. For example, as described herein, a properly registered display may allow an image to be seen across about 80% or more, about 85% or more, about 90% or more, or about 95% or more of the field of view of the display, with a brightness uniformity of 80% or more, about 85% or more, about 90% or more, or about 95% or more. In other words, a display with a "good" registration (as determined by module 772 of FIG. 7C, as an example) may have a brightness uniformity of 90% or more, a display with a "marginal" registration may have a brightness uniformity of 80% or more, and a display with a "failed" registration may have a brightness uniformity of less than 80%.

As also described herein, the center of rotation 1204 may serve as a convenient reference point for referring to and determining the three-dimensional position of the user's eyes. The center of rotation of each of a user's eyes may be determined using the techniques described herein, such as by walking back from the center of curvature of a cornea to the center of rotation (CoR) along the user's optical axis. However, in general, any desired reference point associated with a user's eye may be utilized in the processes and systems described herein. The display registration volume 1203 may represent the volume of space in which display surface 1202 is able to operate at near full potential (e.g., without significant degradation, of the type described in connection with FIGS. 15A and 15B, of the performance of the display surface 1202). If the user's eye (e.g., the center of rotation 1204 of the user's eye) is not within the registration volume 1302*a*, the user may experience degraded performance and some or all of the content provided by display surface 1202 may be partially dimmed or completely invisible to the user.

As shown in FIG. 13A, the registration volume 1302*a* may have the shape of a frustum, which is the portion of a pyramid remaining after its upper portion has been cut off, typically by a plane parallel to its base. In other words, the registration volume 1302*a* may be larger along the x axis and the y axis (see, e.g., FIGS. 12A and 12B) when the user's eye is closer to the display surface 1202 and may be smaller along the x and y axis when the user's eye is further from the display surface 1202. A frustum is an example of a truncation in which the shearing plane (e.g., the line at which a portion of the original shape is cut off) is parallel to the base of the volume. In general, the registration volume such as volume 1302*a* may take the shape of a volume truncated in any manner, such as by one or more non-parallel shearing planes (e.g., such as shown in FIG. 13B) or by one or more non-planar shearings.

The dimensions of the registration volume may depend on the specific implementation of display surface 1202 and other elements of the wearable system. As an example, FIG. 13B illustrates that a registration volume 1302*b* that may be angled with respect to the display surface 1202. In the example of FIG. 13B, the portion of the registration volume 1302*b* closest to display surface 1202 may be angled away from the display surface 1202, such that as the user's eye moves vertically (in the y direction) at the front of the volume (the z position closest to the display surface 1202), the user's eye would need to move away from the display surface (along the z axis) to remain inside the registration volume 1302*b*. In some embodiments, the shape of the registration volume 1302*b* may be based on the capabilities of an eye tracking system, which may not be able to track the user's eyes outside the angled volume 1302*b* of FIG. 13B.

The dimensions and shape of the registration volume may also depend upon the properties of the various parts of display 220, which may include display surface 1202. As an example, display 220 may be a light field display with one or more waveguides (which may be stacked and which can provide multiple vergence cues to the user), in-coupling elements that receive light from an image injection device and couple the light into the waveguides, light distributing elements (sometimes referred to as orthogonal pupil expanders (OPE's)) disposed on the waveguide(s) that distribute light to out-coupling elements, and out-coupling elements (sometimes referred to as exit pupil expanders (EPE's)) that direct light towards a viewer's eye. In some embodiments, as noted herein, the display surface 1202 is a surface or portion of a surface from which light with image information is output from the display system to form images in the eye of the user. For example, the display surface 1202 may be the area on the waveguide surface defined by the out-coupling elements or EPE's, and the perimeter of the display surface 1202 is the perimeter of the area defined by the out-coupling elements or EPE's. Further examples and details of light field displays and the components of such displays are also described in connection with at least FIGS. 9A-9C U.S. Provisional Patent Application No. 62/642,761, filed Mar. 14, 2018, which is incorporated by reference herein in its entirety.

In some embodiments, the x dimensions of registration volume 1302*a* may span approximately 3.0 mm, 3.0 mm, 3.5 mm, 4.0 mm, 4.5 mm, 4.7 mm, 5.0 mm, 5.5 mm, or 6.0 mm; or may be less than 3.0 mm; or more than 6.0 mm along the back of the volume (e.g., at the largest distances along the z-axis from the display surface). Similarly, the y dimensions of the registration volume 1302*a* may span approximately 2.5 mm, 3.0 mm, 3.5 mm, 3.9 mm, 4.0 mm, 4.5 mm, 5.0 mm, 5.5 mm, or 6.0 mm; or may be less than 2.5 mm; or more than 6.0 mm along the back of the volume. At nominal x and y positions, the z dimensions of the registration volume 1302*a* may span approximately 7.0 mm, 7.5 mm, 8.0 mm, 8.5 mm, 9.0 mm, 9.5 mm, 10.0 mm, 10.5 mm, or 11.0 mm; or less than 7.0 mm; or more than 11.0 mm. The x and y dimensions may be larger at the front of the volume. As examples, the x and y dimensions of the registration volume at the front of the volume may be approximately 7.0 mm, 7.5 mm, 8.0 mm, 8.5 mm, 8.9 mm, 9.0 mm, 9.5 mm, 10.0 mm, 10.0 mm, 10.5 mm, 11.0 mm, 11.4 mm, 11.5 mm, 12.0 mm, or 12.5 mm; or less than 7.0 mm; or more than 12.5 mm. As specific examples, the dimensions of the registration volume may include a z-dimension of approximately 9 mm; an x-dimension of approximately 4.7 mm at the back of the volume and approximately 11.4 mm at the front of the volume; and a y-dimension of approximately 3.9 mm at the back of the volume and approximately 8.9 mm at the front of the volume.

In at least some embodiments, there may be multiple registration volumes, such as volumes 1302b and 1304, each of which is associated with a different minimum level of display performance. As an example, volume 1304 of FIG. 13B may be smaller than volume 1302 and may represent the volume in which the user perceives all of the content provided by display surface 1202 at 100% brightness uniformity, whereas the larger volume 1302b may represent the volume in which the user perceives at least 90% of the content provided by display surface 1202 at 100% brightness uniformity. Thus, in some embodiments, the display system may be configured to determine whether the user's eye is within a registration, or viewing, volume of the display, and/or may be configured to determine whether the user's eye is within a threshold distance from the registration volume. For example, in some embodiments, the smaller volume 1304 may be considered to be the baseline registration volume or viewing volume, and the boundaries of the larger volume 1302b may be considered to demarcate an acceptable threshold distance from the registration volume. In some embodiments, if the display system determines that the position of the eye is more than the threshold distance outside of the viewing volume of the display system, the display system may be configured to provide feedback to the user indicating that the display and the eye are not properly registered for output and/or to take actions to mitigate display degradation caused by misregistration, as discussed herein.

In some embodiments, the display registration volume may be determined at least in part based on an application that is currently running or will be run on the system. For example, a larger display registration volume (e.g., volume 1302b) may be employed by the display system when running an application in which only a portion of the field of view is utilized for displaying virtual content, such as a reading-based application in which the reading material may only occupy a portion (e.g., a central portion) of the display's field of view. As a result, the loss, due to misregistration, of the ability of the user to perceive image content at the periphery of the field of view may not be perceptible when running such a reading-based application, since the application may not present content at the periphery. As a result, the larger display registration volume may be utilized to, e.g., reduce unnecessary notifications to the user regarding misregistration when such image registration may not impact the content presented by the application being run on the display system. Similarly, in another example, a larger display registration volume (e.g., volume 1302b) may be employed by the display system when running an application in which the head-mounted display is expected to shift relative to the user's eyes, such as an exercise-oriented application or another application that requires a relatively high-level of user engagement and/or physical activity. In such applications, a notification regarding misregistration may be considered, e.g., distracting, or otherwise detract from the user experience; providing a larger display registration volume reduces the likelihood that the display system will generate such a modification for the user. In some other embodiments, a smaller display registration volume may be utilized (e.g., volume 1304) when running applications in which it is desired to provide content across the full field of view of the display or at peripheral portions of the field of view. Such applications may include immersive gaming applications in which content is displayed across the entirety of the display's field of view. In some implementations, a display registration volume may be determined based on other factors including user preferences, user vision prescription, operating conditions of the system, and the like.

Figure 13C:
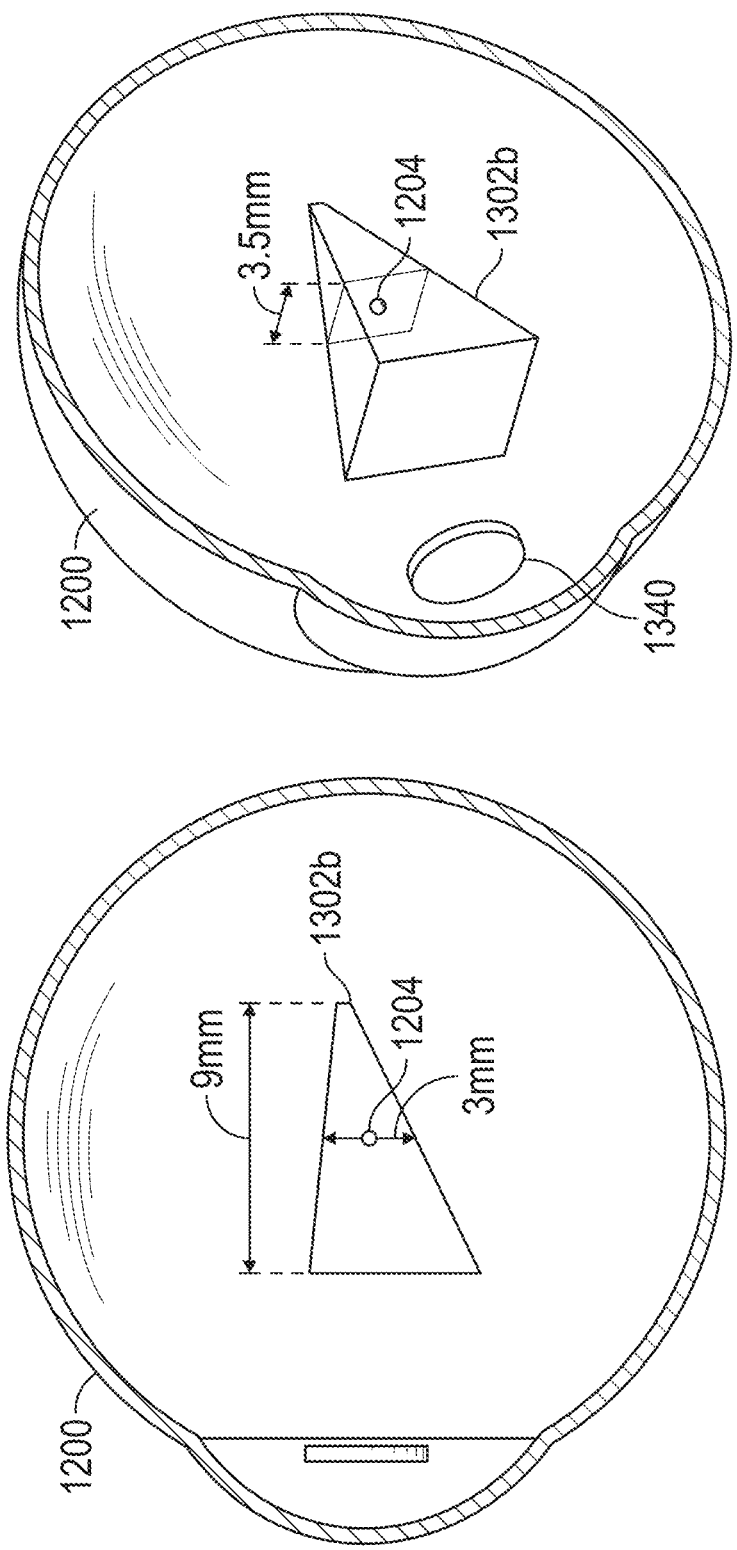
FIGS. 13C and 13D illustrate a display registration volume and a user's eye viewing content from a display.
Figure 13D:
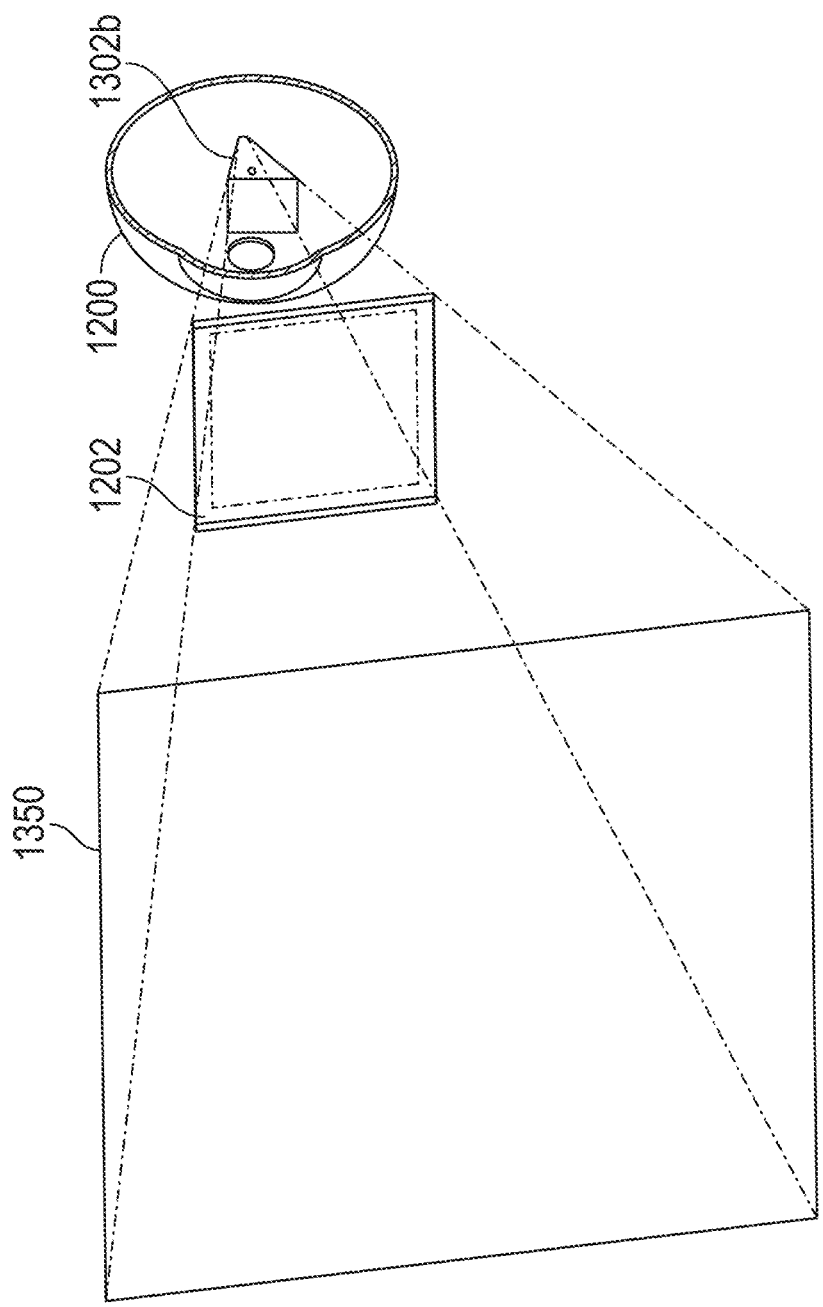

FIGS. 13C and 13D illustrate an example display registration volume, configured to use the center of rotation of an eye as a reference point indicative of the position of the eye, relative to the eye of a user and a display surface. In particular, FIG. 13C illustrates an example positioning of a display registration volume, such as registration volume 1302b, within a user's eye 1200. In the example of FIG. 13C, the center of rotation 1204 of the eye 1200 is roughly centered within the registration volume 1302b. Additionally, the registration volume 1302b is illustrated with example dimensions of approximately 9 mm of depth and, at the mid-point of the depth axis, approximately 3.5 mm of width and 3 mm of height. As discussed herein, the dimensions of registration volume may vary and may be related to the properties of various components of the wearable system. FIG. 13C also illustrates an eye structure 1340, which may be the lens or pupil of eye 1200.

FIG. 13D shows a larger context, in which the user's eye 1200 is generally positioned within registration volume 1302b and is looking through display surface 1202 at virtual content 1350. As discussed herein, virtual content such as the virtual content 1350 may be provided to the user with vergence and accommodation cues associated with greater depths than the depth of the display surface 1202. In other words, the virtual content 1350 may appear to the user with eye 1200 to be at a greater distance from the user than the display 1202. Such an arrangement is illustrated in the example of FIG. 13D.

With continued reference to FIG. 13D, it will be appreciated that the display registration volume 1302b may be an imaginary volume having boundaries defined by a projection from the perimeter of the display surface 1202 to a point inside the eye 1200. For example, the projection may define a pyramid and the display registration volume 1302b may be a frustum of that pyramid. Thus, the cross-sectional shape of the display registration volume 1302b, along planes facing the display surface 1202 on the optical axis, is similar to the shape made out by the perimeter of the display surface 1202. For example, as illustrated, where the display surface 1202 is square, the cross-sectional shape of the display registration volume 1302b is also square. In addition, as also illustrated, where the center of the display surface 1202 is below the user's horizon, a frustum may also be slanted such that a center of the front of the display registration volume 1302b is also below the user's horizon. It will be appreciated that, in some embodiments, the relevant perimeter of the display surface 1202 is the perimeter of the area of the display over which image light or display content is outputted. The boundaries of the display registration volume 1302b may be defined in the same coordinate system in which various features, such as the center of rotation 1204, of the eye 1200 are mapped, thereby allowing comparisons between the display registration volume 1302b and these various features.

In some embodiments, the center of rotation 1204 of the eye is centered within the frustum that defines the display registration volume 1302b. It will be appreciated, however, that the nominal placement of center of rotation 1204 of the eye and/or the overall shape of the frustum may be determined empirically or selected using criteria other than projection from the display surface 1202 so that the display system is able to properly register the display and to provide accurate feedback regarding the quality of the registration and the levels of registration that may be acceptable even if not ideal.

Examples of a Display Performance at Various Registration Positions

Figure 14:
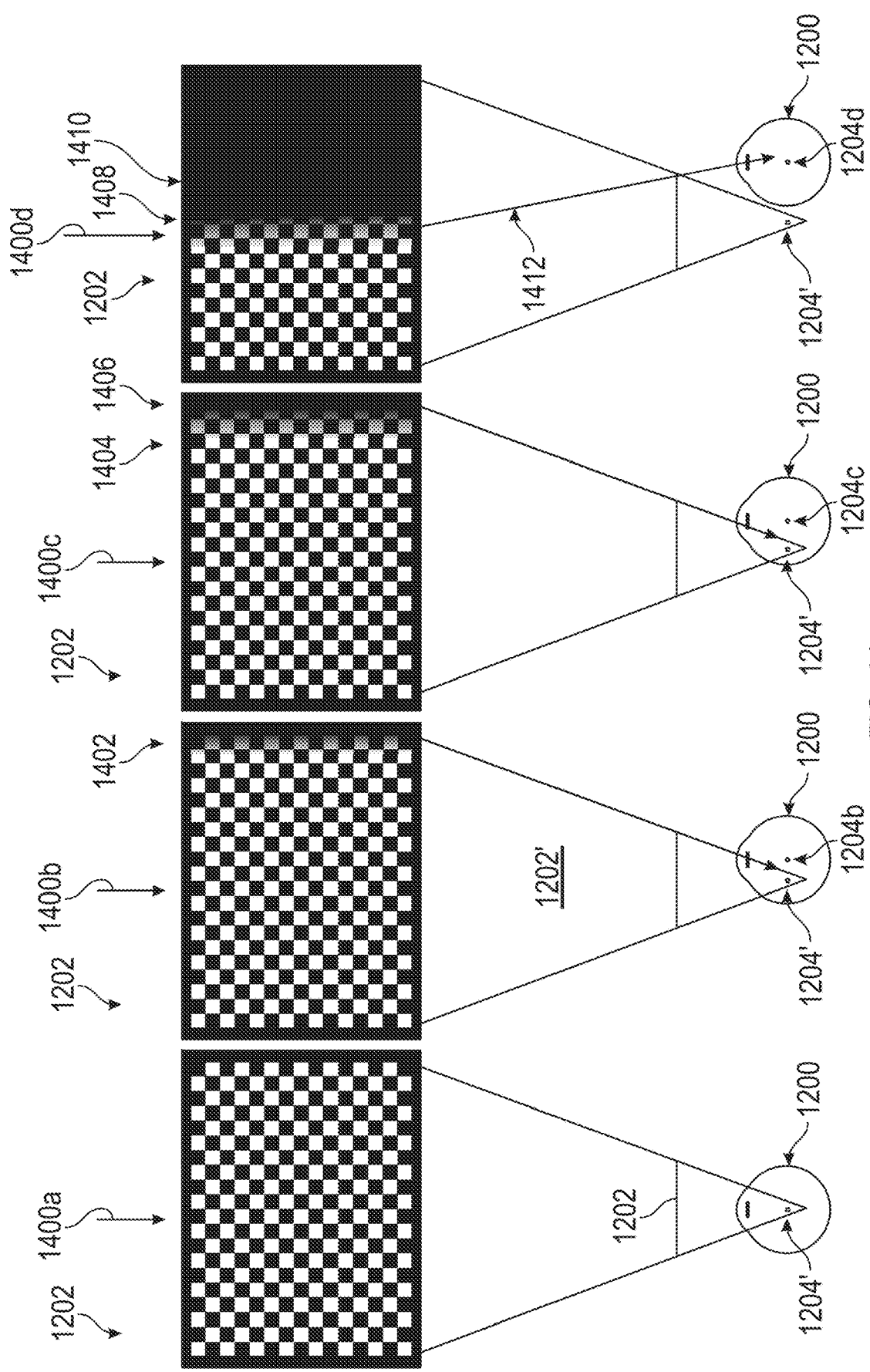
FIG. 14 illustrates an example of the perceived dimming of a display for various positions of a user's eye relative to the display.

FIG. 14 illustrates how the performance of display surface 1202 may vary with the position of the user's eye 1200. As illustrated, light rays from the display surface 1202 may be directed to the eye at an angle, such that light rays from the edges of the display surface 1202 propagate inwards towards the eye 1200. Thus, the cone 1202' represents a cone of light outputted by the display surface 1202 to the eye 1200 to form an image.

Consequently, as the display surface 1202 shifts relative to eye 1200, the exit pupils of pixels corresponding to a respective portion of the field of view do not reach the retina of eye 1200, and the image appears to dim at those portions of the field of view. The positions 1204a, 1204b, 1204c, and 1204d of the center of rotation of the eye are effectively shifted relative to the idealized position 1204' of the center of rotation; movement of the display surface 1202 relative to the eye 1200 may cause the center of rotation of the eye to possibly move outside of the display registration volumes 1302a, 1304, 1302b (FIGS. 13A and 13B) for the display surface 1202. As discussed herein, the display registration volumes may be tied to the display surface 1202, e.g., the display registration volumes may be defined by projections from the display surface 1202. Consequently, as the display surface 1202 moves relative to the eye 1200, so do the display registration volumes 1302a, 1302b (FIGS. 13A and 13B). FIG. 14 illustrates various positions (e.g., positions 1204a, 1204b, 1204c, and 1204d) of the center of rotation of a user's eyes, the relative position of a display surface 1202, and representations (e.g., representations 1400a, 1400b, 1400c, and 1400d) of how the content provided by display surface 1202 would be perceived by the user at each of the various positions.

In example 1400a, the center of rotation of the user's eye may be at position 1204a, which may be centered within a registration volume such as registration volume 1300b (e.g., a volume in which image quality is high due to the eye 1200 receiving on its retina nearly all of the image light outputted by the display surface 1202). Representation 1400a may represent the user's perception (or view) of the content provided by display surface 1202, when the user's eye is at position 1204a. As shown by representation 1400a, the luminance for substantially all of the content across the display surface 1202 is uniform and may be at or near full brightness levels.

In example 1400b, the center of rotation of the user's eye may be at position 1204b, which may be outside a preferred display registration volume such as volume 1304 (FIG. 13B) but inside a secondary registration volume such as volume 1302b (e.g., a volume in which display performance is only slightly degraded). Representation 1400b may represent the user's perception (or view) of the content provided by display surface 1202, when the center of rotation of the user's eye is at position 1204b. As shown by representation 1400b, the portion 1402 of the image along the right side of the display surface 1202 may have a perceived reduced brightness (e.g., a 50% brightness) due to misregistration of the user's eye relative to the display surface 1202.

In example 1400c, the center of rotation of the user's eye may be at position 1204c, which may be outside (or on the outside edge of) a second registration volume such as volume 1302b (FIG. 13B). Representation 1400c may represent the user's perception (or view) of the content provided by display surface 1202, when the center of rotation of the user's eye is at position 1204c. As shown by representation 1400c, a portion 1406 along the edge of the displayed image user's perception may appear completely (or nearly completely) dimmed and thus not seen by the user due to misregistration. In arrangements in which some pixels of the display are below a perceived luminance level, the display may provide a reduced field of view (e.g., the user may not be able to perceive the full field of view the display is otherwise capable of presenting). Additionally, there may be a band or portion 1404 of the image having progressively reduced brightness between the dark portion 1406 and the rest of the representation.

In example 1400d, the center of rotation of the user's eye may be at position 1204d, which may be well outside the desired registration volumes. Representation 1400d may represent the user's perception (or view) of the content provided by display surface 1202, when the center of rotation of the user's eye is at position 1204d. As shown by representation 1400d, large portions 1410 of the image may appear completely (or nearly completely) dark to the user and a substantial portion 1408 of the image may appear dimmed, due to the significant misregistration.

As discussed herein, it will be appreciated that the display system may be configured to increase the light output or perceived brightness of portions of the field of view of the display which undergo dimming due to misregistration. For example, upon determining that there is misregistration, as discussed herein, the display system may provide a notification in the form of a flag or instructions for the display to increase the amount of light outputted to the user for pixels expected to undergo dimming due to misregistration. For example, in example 1400b, pixels representing image information in portion 1402 may have their perceived brightness boosted to mitigate reductions in perceived brightness expected from misregistration.

It will be appreciated that the ability to boost brightness to compensate for dimming may diminish with high levels of misregistration. For example, in example 1400d, the area 1410 may be dark due to the eye 1200 not receiving any light from pixels in those areas. Consequently, while boosting brightness may mitigate dimming due to misregistration in the portion 1402 (example 1400b), boosting brightness may not be able to mitigate dimming in portions 1410 (example 1400d) of the display where misregistration prevents the eye from receiving light at all. The portion 1410 is larger than the portion 14 to and, as an approximation, the size of the portion expected to be dimmed may be indicative of whether or not boosting brightness is effective; that is, if the size of the portion (e.g., the number pixels) expected to be dimmed is sufficiently large, then, in some embodiments, it may be assumed that the misregistration is sufficiently great that boosting brightness will not be effective for most of those pixels. As a result, in some embodiments, the display system may be configured to compare the number pixels in the portions expected to be dimmed, and if that number exceeds a threshold, then provide feedback to the user indicating that the display and the eye are not properly registered.

Example of Interchangeable Fit Pieces for Wearable Systems

Figure 15A:
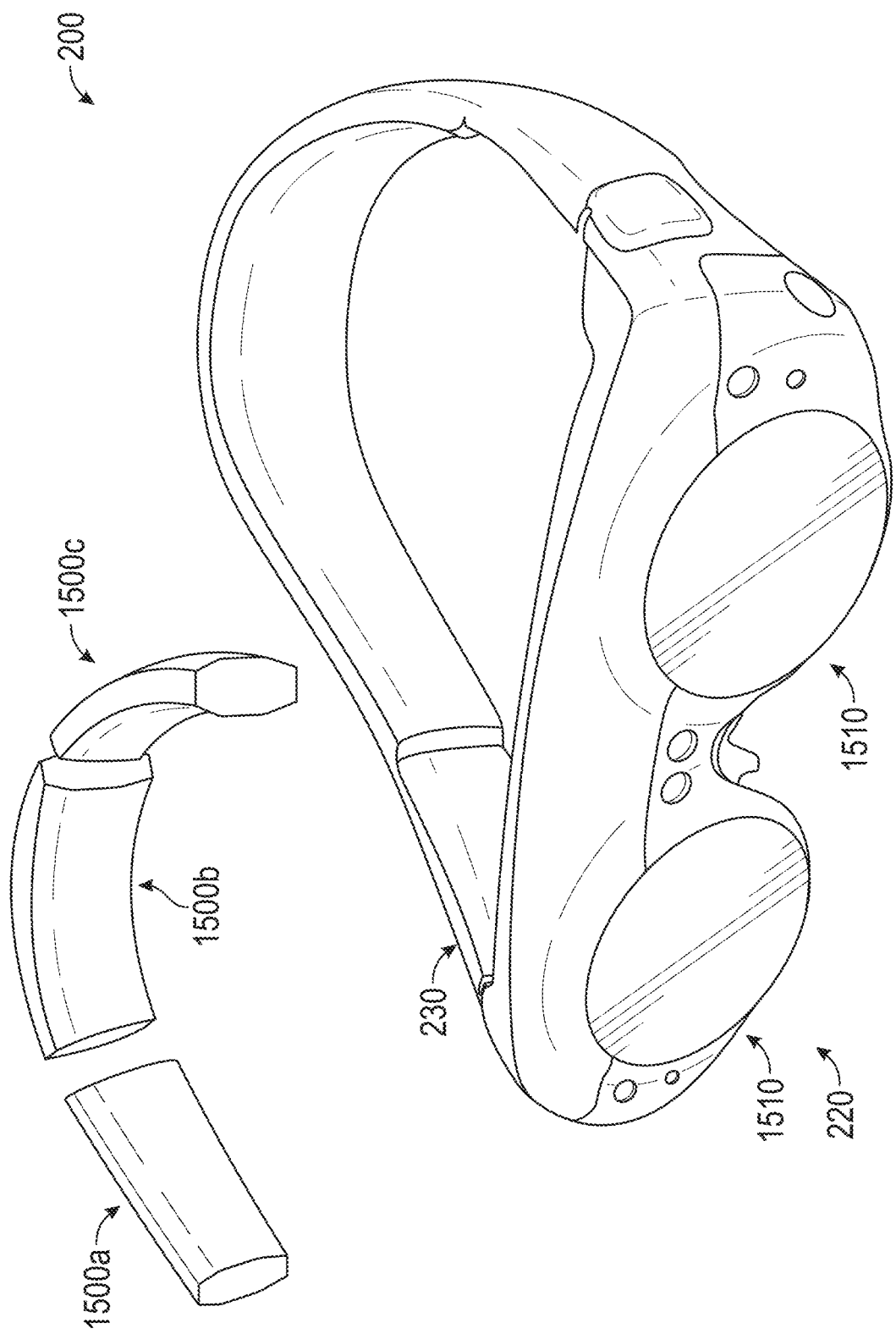
FIGS. 15A and 15B are exploded perspective views of a head-mounted display system having interchangeable pieces such as back pads, forehead pads, and nose bridge pads to adjust fit of a head-mounted display of the display system for different users.
Figure 15B:
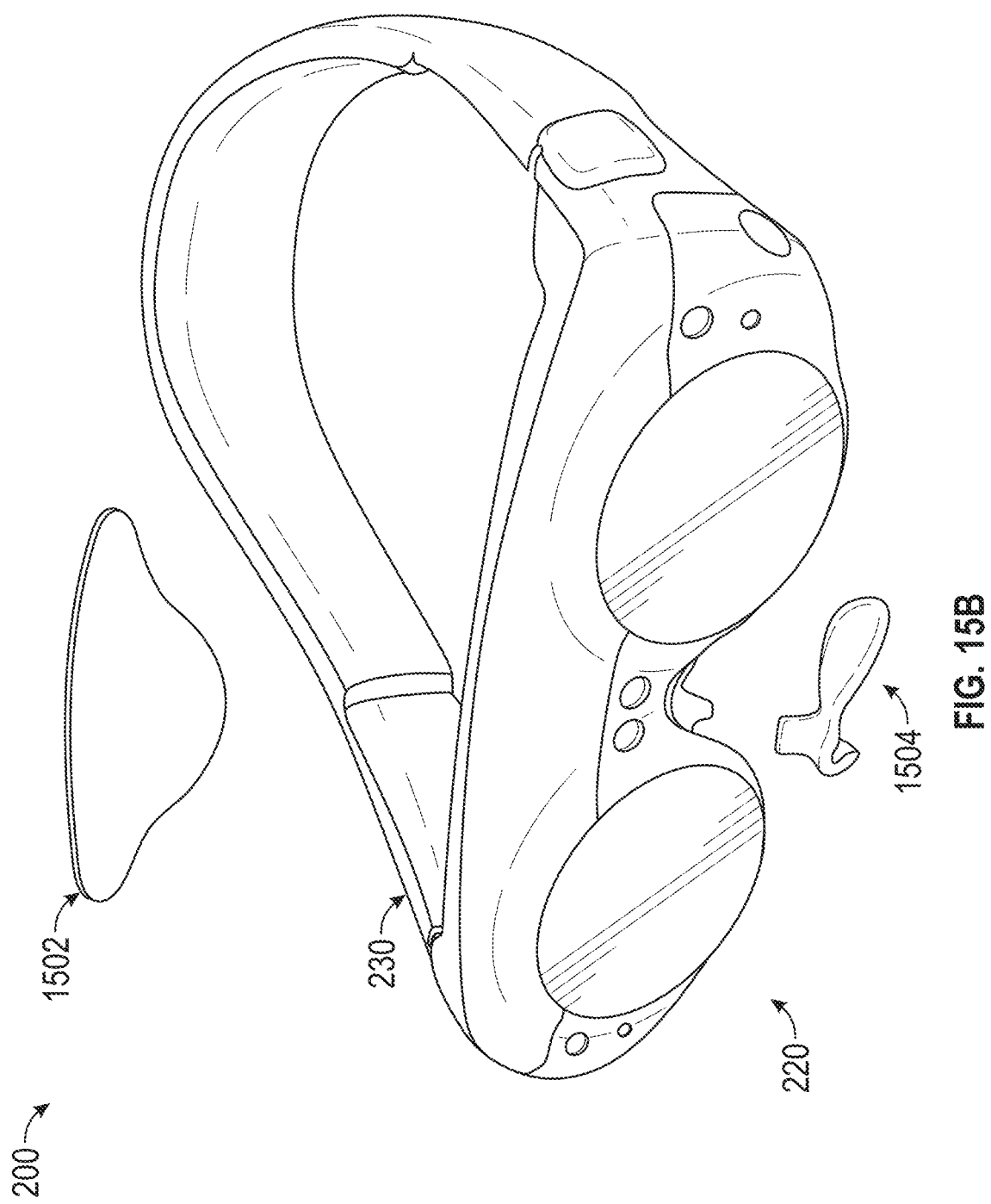

FIGS. 15A and 15B show exploded perspective views of the wearable system 220, which may include interchangeable fit pieces. In particular, FIG. 15A illustrates how the wearable system 200 may include interchangeable back padding such as pads 1500a, 1500b, and 1500c; while FIG. 15B illustrates how the system 200 may include interchangeable forehead pads such as pad 1502 and interchangeable nose bridge pads such as pad 1504. These interchangeable pads may be used to adjust the fit of the wearable system 200 for individual users, whom may have varying anatomical attributes (e.g., how the display 220 and frame 230 fit for various different users). As examples, users with relatively small heads may benefit from attaching relatively large back pads 1500*a*, 1500*b*, and 1500*c* to the frame 230, while users with relatively large heads may obtain better results (e.g., better optical performance and stability of the frame 300 on their head) by attaching relatively small back pads, or even omitting the back pads. Similarly, users with prominent noses and/or foreheads may benefit from smaller forehead pads 1502 and/or nose bridge pads 1504; while users with less prominent noses and/or foreheads may benefit from larger forehead pads 1502 and/or nose bridge pads 1504. These are merely illustrative examples and, in general, determining the set of interchangeable pads that result in the best fit for any particular user may be complex. As described herein, the display system may display a notification to the user indicating that a different interchangeable fit piece may be desirable to provide proper registration of the display to the user.

With reference to FIG. 15A, the wearable system may include one or more housing openings 1510. The housing openings 1510 may be openings in frame 230 and may, if desired, optionally include lenses or other structures, such as optically transmissive structures for mechanical protection of the waveguides of the display. Lenses in housing openings 1510 may be clear (e.g., fully or nearly fully transparent) or may be partially opaque (e.g., in order to reduce the level of ambient light that passes through the openings 1510). The openings in frame 230, while illustrated in FIG. 15A as being approximately circular, may have any desired shape.

Example Processes of Observing Device Registration

Figure 16:
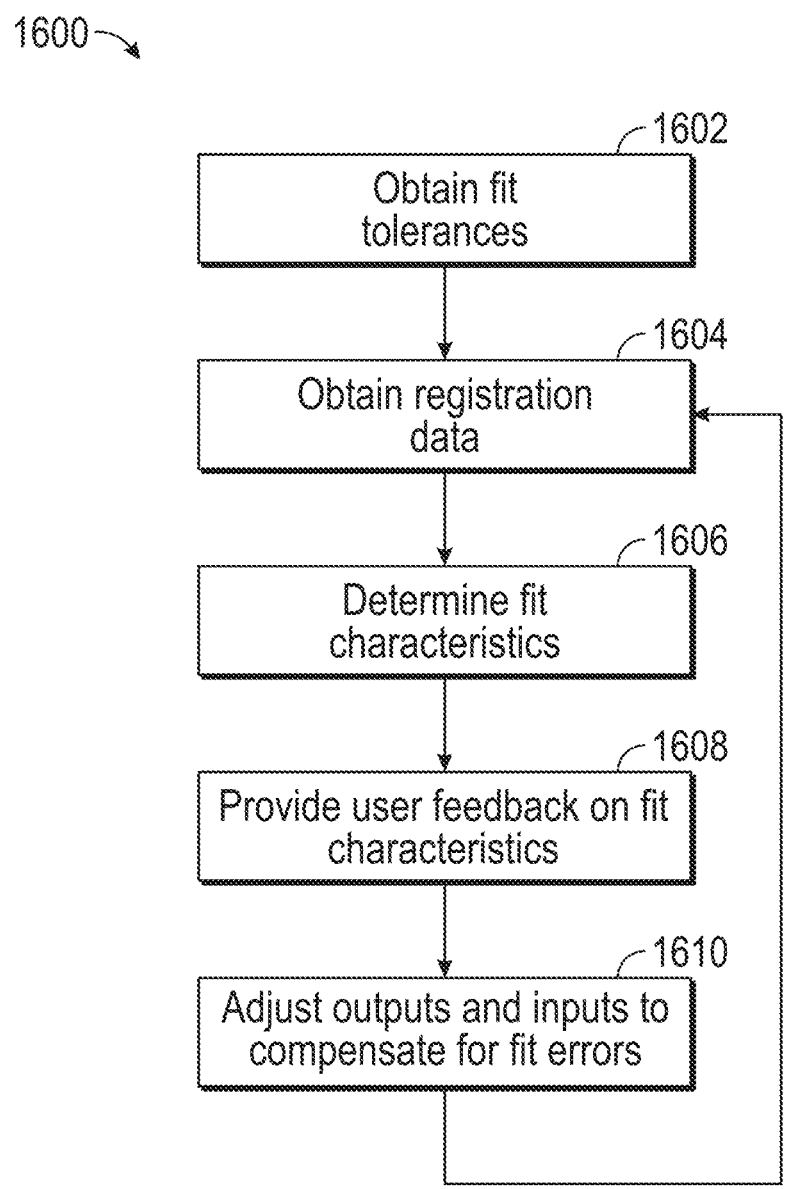
FIG. 16 is a process flow diagram of an example of a method for observing registration and providing feedback on registration with a head-mounted display system.

FIG. 16 is a process flow diagram of an example method 1600 for observing device registration and providing feedback on registration or compensation for misregistration in a wearable device. The method 1600 may be performed by the wearable systems described herein. Embodiments of the method 1600 may be used by the wearable system to provide feedback on registration (i.e., fit of the wearable device to the user) based on data from an eye tracking system and to adjust a display to attempt to compensate for fit errors (e.g., misregistration).

At block 1602, the wearable system may obtain fit tolerances. The fit tolerances may include information associated with display registration volumes such as volumes 1302*a*, 1302*b*, or 1304. In particular, the fit tolerances may include information associated with nominal (e.g., normal) positions of the user's eyes relative to the wearable device and may include information associated with how variances from the nominal positions impact device performance. As one example, the fit tolerances may include information on a range of nominal positions for which the wearable device is able to interface with a user at least a certain desired amount of performance (e.g., with no more than 50% dimming on any pixel in a display).

At block 1604, the wearable system may obtain registration data. The registration data may include spatial relationships between various components of the wearable system and associated portions of the user. As examples, the registration data may include one or more of the three-dimensional positions of a user's left eye relative to a left-eye display of the wearable system; 3D positions of the user's right eye relative to a right-eye display; and 3D positions of the user's ears relative to audio outputs (e.g., speakers, headphones, headsets, etc.) of the wearable system. The wearable system may obtain registration data using any suitable mechanisms. As an example, the wearable system may capture images of a user's eye or eyes using eye-tracking cameras 324 of the type shown in FIG. 3 (or other cameras, which may or may not be inward-facing cameras) to determine the relative positions of the user's eyes and the wearable system. As other examples, the wearable system may include depth sensors, pressure sensors, temperature sensors, light sensors, audio sensors, or other sensors to measure or obtain registration data such as the position of the wearable device relative to a user.

At block 1606, the wearable system may determine fit characteristics. As an example, the wearable system may determine whether the user's left eye lies within a left-eye registration volume (such as one of volumes 1302*a*, 1302*b*, or 1304 for the left eye) and whether the user's right eye lies within a right-eye registration volume (such as one of volumes 1302*a*, 1302*b*, or 1304 for the right eye). Block 1606 may also involve determining how far the user's eyes (or other body parts) are from their nominal positions. As an example, the wearable system, in block 1606, may determine that at least one of the user's eyes is outside of its respective the display registration volume, by how much and in which direction the user's eyes are outside of their display registration volumes. Information on the direction and magnitude of the misregistration (e.g., the distance between the registration volumes or nominal positions and the actual positions of the user's eyes or other body part) may be beneficially utilized in blocks 1608 and 1610.

At block 1608, the wearable system may provide a user (or some other entity) with feedback on the fit characteristics determined in block 1608. As an example, if the wearable system determines in block 1606 that the wearable device is too low relative to the user's eyes, the wearable system may provide the user, at block 1608, with a notification suggesting that the user utilize an appropriate nose bridge pad 1504 (e.g., to add a nose bridge pad if none were previously attached or to swap out an existing nose bridge pad for a larger or taller nose bridge pad). Conversely, if the wearable device determines it is too high relative to the user's eyes, the system may provide a suggestion to the user to use a smaller nose bridge pad or remove the pad altogether (if designed to be wearable without a pad). As other examples, the wearable system may provide the user with feedback suggesting a change to forehead pads such as pad 1502, back pads such as pads 1500*a*-1500*c*, a change to other adjustable components of the wearable system, a change to how the user is wearing the wearable system (e.g., instructions to move or rotate the system in a particular direction relative to the user). In general, user feedback may be generated based on the position(s) of the user's eye(s) relative to the display or other metrics such as the visible image portions identified by the system. As an example, when the system determines that the user's eye is above the registration volume, the system may recommend to the user that the user push the wearable device upwards along the bridge of their nose in order to correct the misregistration.

User feedback may be provided using any suitable device. As examples, user feedback may be provided via video presented by a display in the wearable device or an external display or via audio presented by the wearable device or by an external device. In various embodiments, the wearable device may provide an interactive guide for assisting the user in obtaining proper registration in a relatively intuitive manner. As an example, the wearable device could display two virtual targets, one representative of the position of the user's eyes and the other representative of the nominal registration position. Then, as the user moves the wearable device around and adjusts its fit, the user can perceive how their adjustments impact registration and the user can quickly and intuitively achieve proper registration.

In arrangements in which user feedback is provided by an output device, such as a display, that is part of the wearable device, the wearable device may provide the user feedback in a manner that ensures the user is able to perceive the feedback. Consider, as an example, representation 1400d of FIG. 14. In such an example, the wearable system may move user feedback into portion of the displayed image that is perceived by the user e.g., the left-half of the display, as opposed to the invisible right-half of the display in the example 1400d of FIG. 14.

In some embodiments, feedback of the type described herein may be provided to a sale associate in a retail environment and the feedback may be communicated over a network to the sale associate's computer or mobile device.

At block 1608, the wearable system may adjust its outputs and inputs to compensate for uncorrected fit errors. In some embodiments, block 1608 may be performed only after a user has failed to correct fit errors in response to feedback. In other embodiments, block 1608 may be performed until a user corrects fit errors. In some embodiments, block 1608 may be performed whenever the user decides to continue using the wearable system with fit errors. In some embodiments, block 1608 may be omitted.

As examples, the wearable system may adjust its outputs and inputs in block 1608 by adjusting portions of a displayed image (e.g., to compensate for misregistration-induced dimming, of the type shown in FIG. 14), by adjusting microphone inputs (e.g., boosting microphone gain when a user is too far from a microphone, or reducing microphone gain when the user is too close to the microphone), by adjusting speaker outputs (e.g., boosting or dimming speaker volume when a user is too close or too far, respectively, from a speaker in the wearable device), etc. As one particular examples, the wearable system may selectively boost the luminance of portions of the image, such as portions 1402, 1404, or 1408 of FIG. 14, in an attempt to reduce misregistration-induced dimming. In some other embodiments, the wearable system may recognize that certain portions of the image, such as portions 1406 or 1410 of FIG. 14. are not visible to the user and may reduce light output in those regions to reduce energy consumption by the wearable system. For example, in configurations where different portions of the image may have dedicated, selectively-activated light sources or portions of a light source, the one or more light sources or portions of a light source associated with the unseen portions of the image may have their light output reduced or turned off.

Example of Identifying a Display Registration Volume

FIGS. 17A-17H illustrate views of light fields projected by a display and how the intersections of the light fields may partly define a display registration volume. FIG. 18 illustrates a top-down view of overlapping light fields projected by a display and how the intersections of the light fields can partly define a display registration volume. As FIGS. 17A-17H and 18 illustrate, the size and shape of display registration volume can depend in part upon the geometry of the display (which can be display 220 of FIG. 2) as well as the angles at which out-coupled light propagates out of the display (e.g., out of the waveguide the display). It will be appreciated that the angles at which the light is output may define the FOV of the display; larger angles relative to the normal provide a larger FOV. In some embodiments, the display surface may output angles large enough to provide a desired FOV.

FIGS. 17A-17H and 18 illustrate display 220, which can be a light field display including elements such as waveguide 1701, in-coupling elements 1702, orthogonal pupil expanders (OPE's) 1704, and exit pupil expanders (EPE's) 1706 (which can form a display surface 1202, which is also illustrated in various other Figures herein including FIGS. 12A-14). As an example, the in-coupling elements 1702 can receive light from an image source and couple the light into waveguide 1701. The waveguide 1701 can convey the light to OPE's 1704, the OPEs 1704 may provide pupil expansion and direct the light to EPE's 1706, and the EPE's 1706 (which can be provided on display surface 1202) provide further pupil expansion and convey the light to the user's eye(s). Further examples and details of light field displays and the components of such displays are also described in connection with at least FIGS. 9A-9C U.S. Provisional Patent Application No. 62/642,761, filed Mar. 14, 2018, which is incorporated by reference herein in its entirety.

Figure 17A:
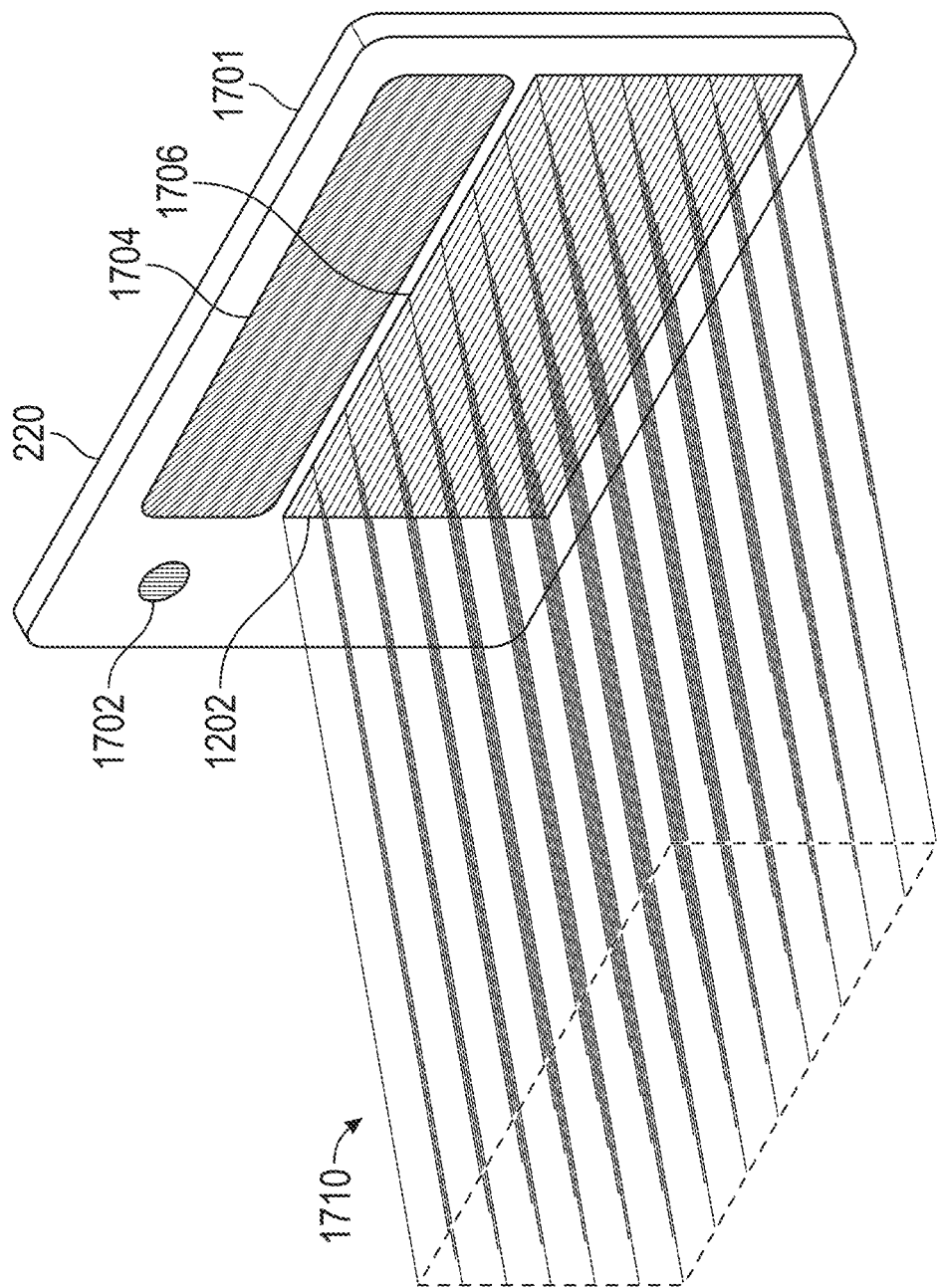
Figure 17C:
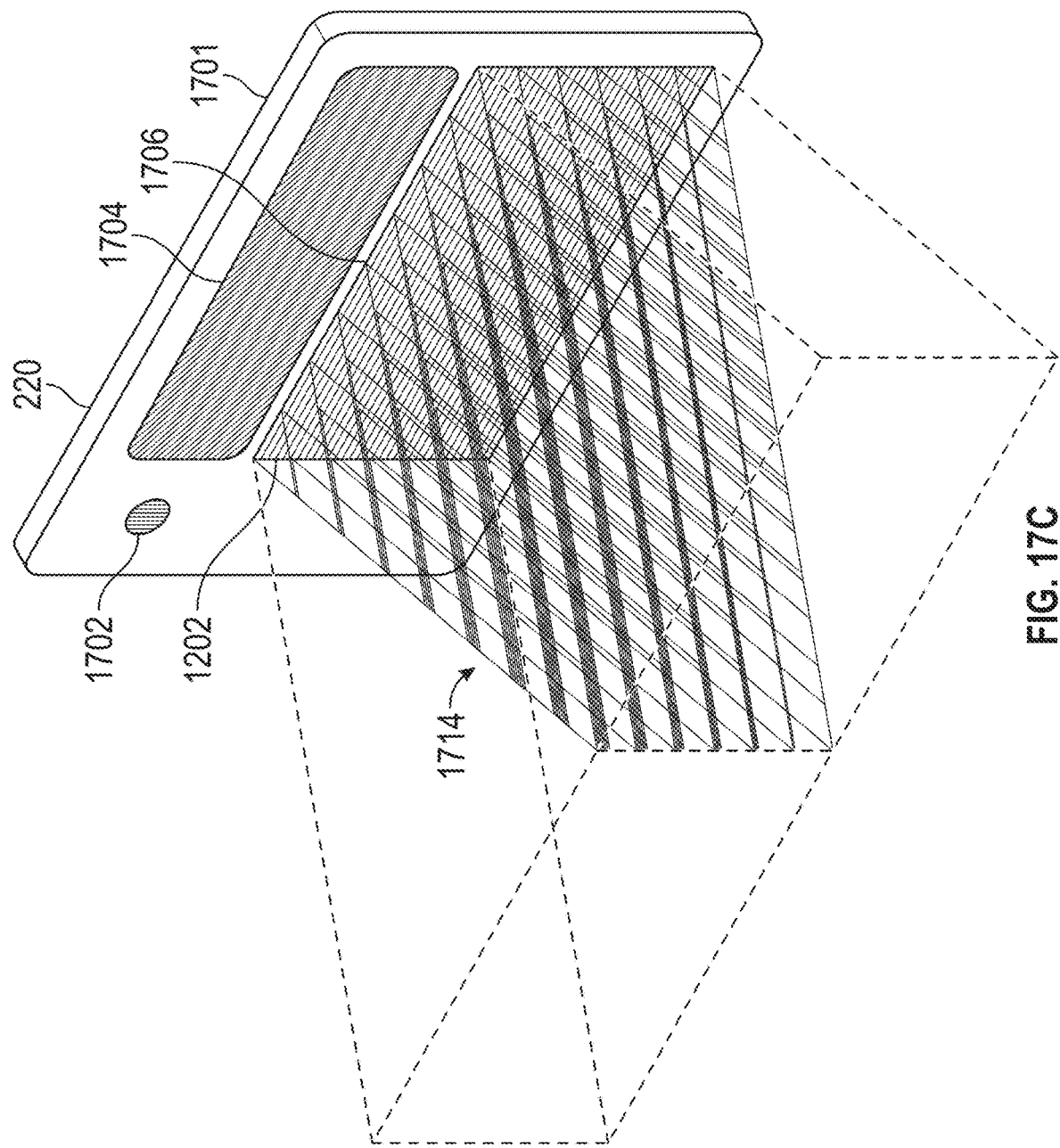

FIG. 17A illustrates an example in which the display 220 is projecting light 1710 associated with virtual image content at optical infinity and the right-most region (e.g., right-most pixel) of the FOV of the display. In contrast, FIG. 17B illustrates an example in which the display 220 is projecting light 1712 associated with an object at optical infinity and the left-most region (e.g., left-most pixel) of the FOV of the display. FIG. 17C illustrates the overlapping region 1714 of the light 1710 of FIG. 17A and the light 1712 of FIG. 17B. Region 1714 may be a horizontal registration volume. In particular, when the user's eye is disposed within region 1714 of FIG. 17C, the user is able to perceive (e.g., display 220 is able to provide the user with light from) objects at both the right-most region of the FOV (as in FIG. 17A) and the left-most region of the FOV (as in FIG. 17B).

Figure 17D:
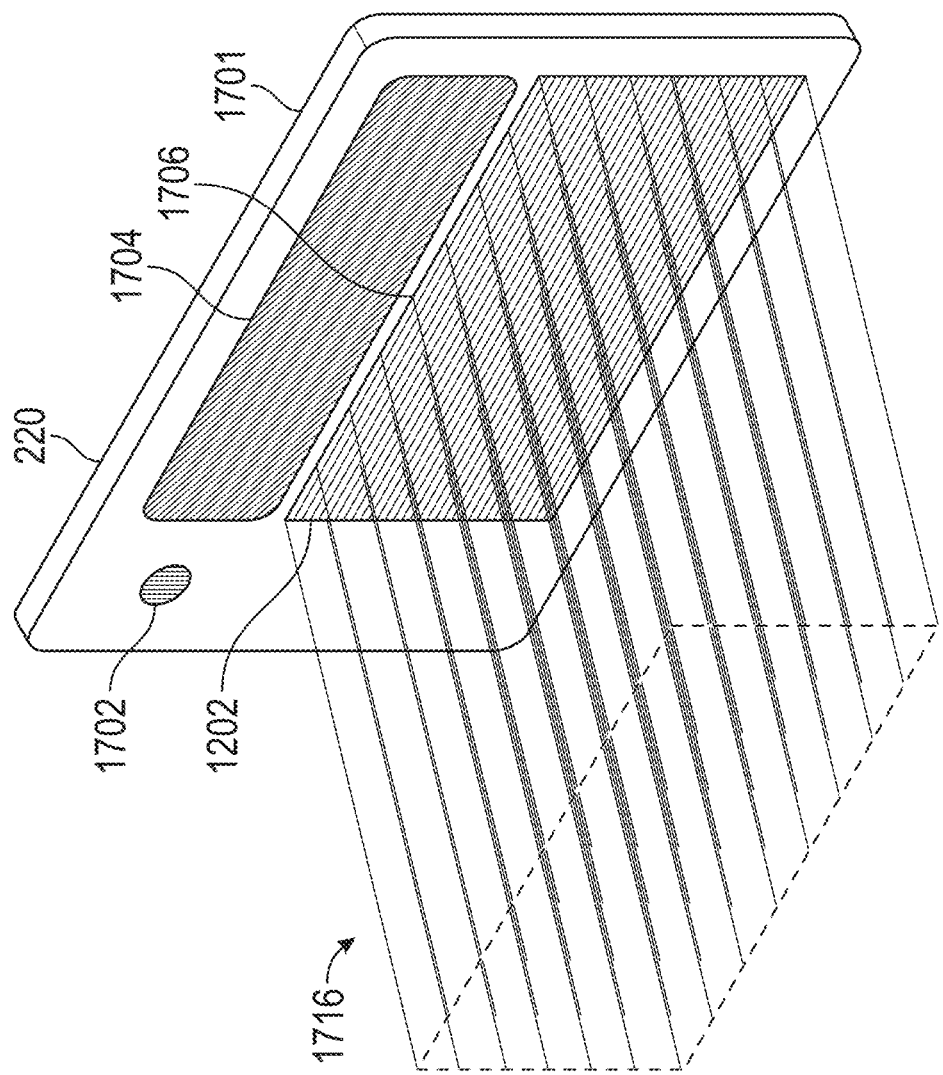
Figure 17E:
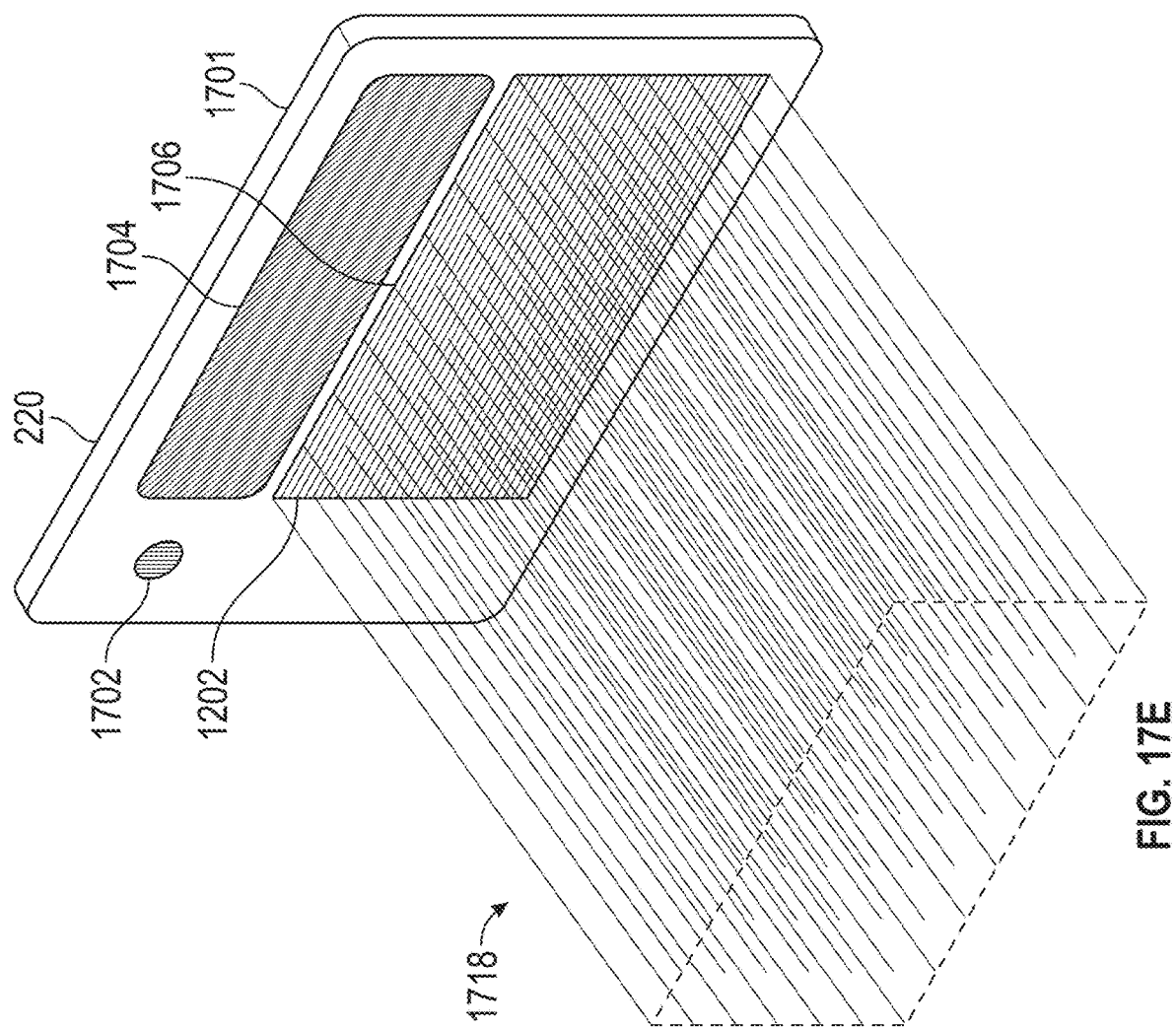
Figure 17F:
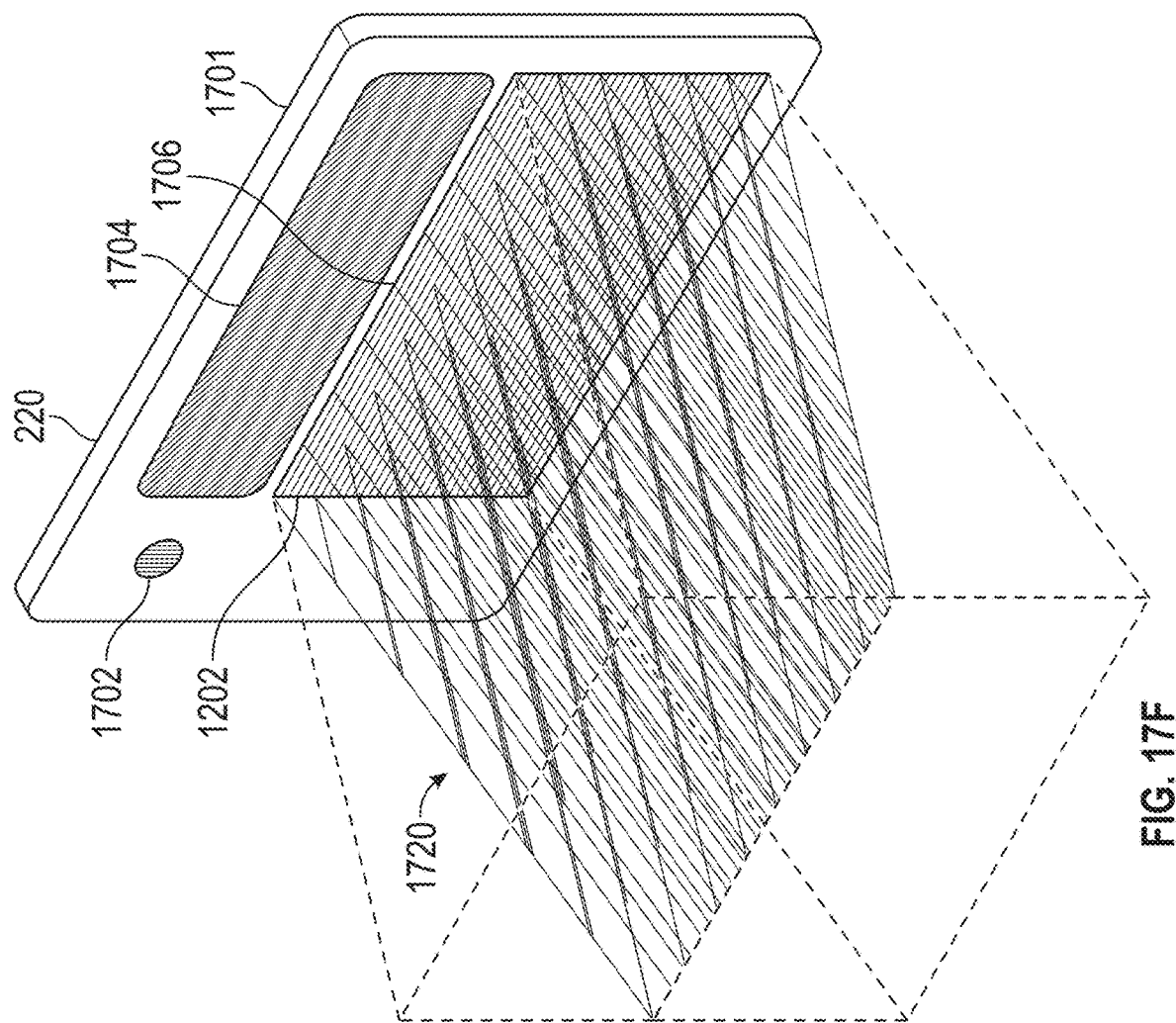

FIGS. 17D-F illustrate examples similar to those of FIGS. 17A-17E, except in the vertical direction. In particular, FIG. 17D illustrates an example in which the display 220 is projecting light 1716 associated with an object at optical infinity and the bottom-most region (e.g., bottom-most pixel) of the FOV of the display, while FIG. 17E illustrates an example in which the display 220 is projecting light 1718 associated with an object at optical infinity and the top-most region (e.g., bottom-most pixel) of the FOV of the display. Similarly, FIG. 17F illustrates the overlapping region 1720 of the light 1716 of FIG. 17D and the light 1718 of FIG. 17E. Region 1720 may be a vertical registration volume. In particular, when the user's eye is disposed within region 1720 of FIG. 17F, the user is able to perceive (e.g., display 220 is able to provide the user with light from) objects at both the bottom-most region of the FOV (as in FIG. 17D) and the top-most region of the FOV (as in FIG. 17E).

Figure 17G:
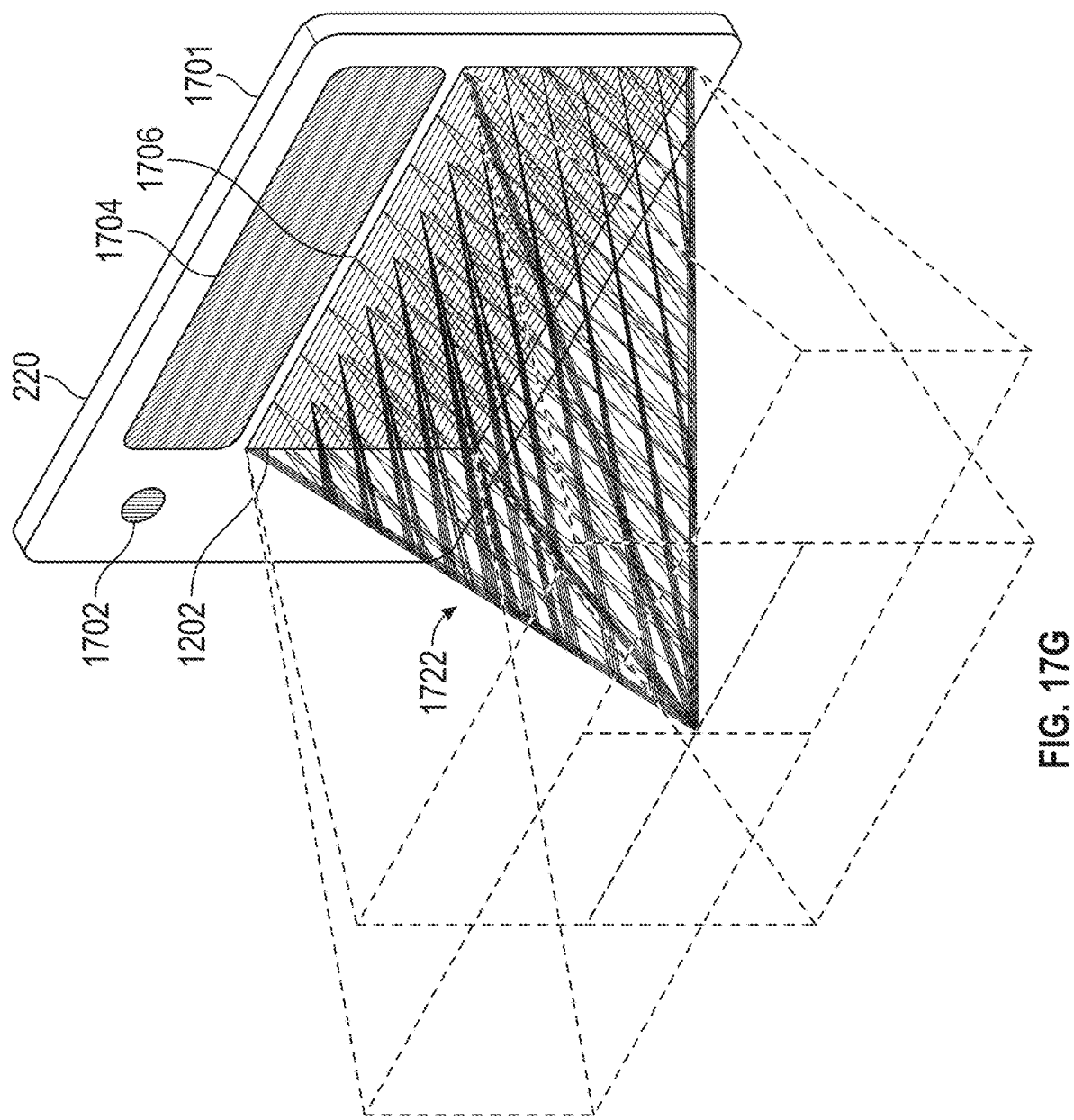
Figure 17H:
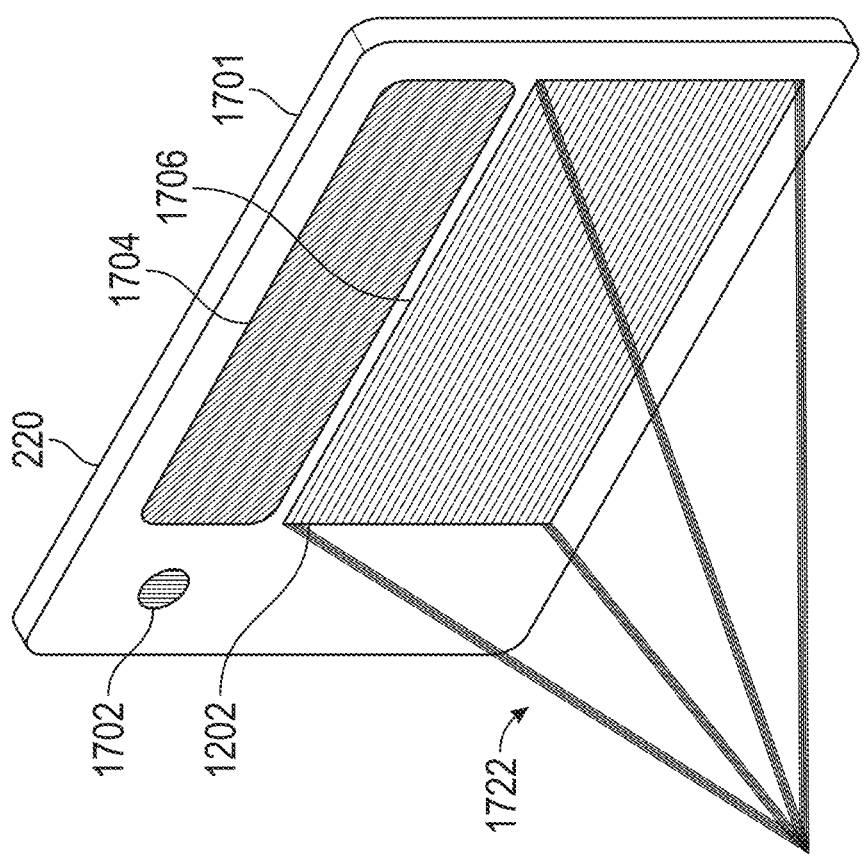

FIGS. 17G and 17H illustrate the intersection (as region 1722) of the regions 1714 of FIG. 17C and the region 1720 of FIG. 17F. In particular, FIG. 17G illustrates the region 1722 in which light from objects at the four corners of the FOV of display 220 overlaps. FIG. 17H illustrates just the outline of region 1722. As should be apparent, when the user's eye is disposed within region 1722, the user is able to perceive (e.g., display 220 is able to provide the user with light from) objects anywhere within the FOV of the display. In some embodiments, the registration volume of the display 220 may be understood to be a viewing volume of the head-mounted display through which light representing every pixel of virtual image content presented by the head-mounted display is expected to pass.

In some embodiments, increasing the FOV of display 220 (horizontally, vertically, or a combination thereof) while holding other attributes (such as display size) constant may have the effect of shrinking the relevant registration volume (e.g., the horizontal volume 1714, the vertical volume 1720, or the combined registration volume 1722). Consider, as an example, FIGS. 17A-C and the horizontal FOV and registration volume 1714. An increase in the horizontal FOV of display 220 means light 1710 from objects on the right horizontal edge is projected by display surface 1202 (e.g., EPE's 1706) at a sharper angle (e.g., a greater angle from normal to display surface 1202). Similarly, light 1712 from objects on the left horizontal edge is projected at a sharper angle. Thus, in the perspective of FIG. 17C, the apex of the horizontal registration volume 1714 moves toward display surface 1202 with increases in horizontal FOV, thereby shrinking volume 1714. Similar considerations may apply in some embodiments to the vertical FOV and the vertical registration volume, as well as the overall FOV and overall registration volume.

FIG. 18 shows a top-down view of display 220 including display surface 1202, which may have a rectangular shape and a particular FOV, as well as light rays produced by the display. In general, the registration volume of the display 220 of FIG. 18 may be the volume 1802, which appears triangular in the top-down perspective of FIG. 18. The volume 1802 may represent the volume where the various light fields formed by the light shown in FIGS. 17A-17G overlap. If a user's eye is located outside of volume 1802 (e.g., in volume 1804), it may be seen that light of light fields from at least some portion of the display 220 would fail to reach the user's eye, resulting in partial or complete dimming of a portion of the FOV.

It should be noted that a side-view of the display and registration volume would have much the same appearance (at least for a rectangular display) as that shown in FIG. 18, although the illustrated dimension of display 220 would be the height of the display 220 rather than its width and the illustrated FOV would be the vertical FOV rather than the horizontal FOV shown in FIG. 18. Thus, the volume 1802 may actually have a somewhat pyramidal shape. In other embodiments, the display may have non-rectangular shapes such as a circular shape, an elliptical shape, a free-form shape, or any other desired shape. In such embodiments, the corresponding registration volume may be determined by projecting light fields at the relevant FOV and identifying where those light fields intersect (which may correspond to volume 1802) and where the light fields do not intersect (which may correspond to volume 1804).

As discussed herein, the "base" of the pyramid may be truncated (which may help to move the user's eyes away from the display such that the user's eyelashes do not impact the display when properly registered) and the "top" of the pyramid may also be truncated (which may be helpful in reducing the impacts of noise in the location determination of the user's eyes, which might otherwise rapidly move into and out of registration at the "top" of a pyramidal shaped registration volume). It will be appreciated that the "top" is proximate the apex of the volume 1802, and the base is proximate the waveguide 1701. When the user's eyes are located in regions 1804 outside of the registration volume 1802, the user may perceive dimming of some or all of the pixels of display 220, as discussed herein (see, e.g. FIG. 14).

In general, the registration volume may be adjusted (e.g., truncated or otherwise reduced) in any number of ways for a variety of reasons. As an example, the registration volume may be truncated such that the volume has a minimum distance from display 220, to prevent the user's eyelashes or lids from impacting the display 220. Consequently, in some embodiments, the display system (e.g., processing electronics of the display system) may be configured to determine whether the user's eyes are inside of the registration volume 1802 by, at least in part, determining whether one or both eyes are less than a minimum threshold distance (e.g. a minimum allowable distance) from the display 220. If an eye is determined to be at less than the minimum threshold distance from the display, then the display system may interpret this result to mean that the eye is outside of the registration volume 1802 and, thus, the display and the eye are not properly registered. As a result, the display system may provide feedback to the user indicating that the registration is improper, and/or may be configured to take actions to mitigate display degradation caused by misregistration, as discussed herein. In some implementations, such a minimum threshold distance may vary in one or more dimensions. For example, the minimum threshold distance may linearly vary along the z-axis as a function of distance from the nominal position and/or the surface of the display.

In addition or as an alternative to determining whether the eye is within a minimum distance from the display 220, in some embodiments, the display system (e.g., processing electronics of the display system) may be configured to determine whether the user's eyes are inside of the registration volume 1802 by, at least in part, determining whether one or both eyes are more than a maximum threshold distance from the display 220. It will be appreciated that the maximum threshold distance may correspond to the distance at which the "top" of the pyramid 1802 noted above is truncated. If an eye is determined to be at more than the maximum threshold distance from the display, then the display system may interpret this result to mean that the eye is outside of the registration volume 1802 and, thus, the display and the eye are not properly registered. As a result, the display system may provide feedback to the user indicating that the registration is improper, and/or may be configured to take actions to mitigate display degradation caused by misregistration, as discussed herein.

In addition or as an alternative to determining whether the eye is within a minimum distance and/or beyond a maximum distance from the display 220, the wearable system may have an eye tracking system, including elements such as cameras 324 and light sources 326 of FIG. 6, which may only track the user's eyes if the user's eyes are within an eye tracking volume, which may not overlap exactly with the display registration volume. In some embodiments, the camera of the eye tracking system may have a field of view which encompasses the display registration volume. Thus, the display registration volume may be considered to be a subspace, or portion, of the camera's field of view. The display system may be configured to determine whether the user's eye is within that subspace, or within a threshold distance from that subspace, when imaged by the camera. If the eye is within the subspace or within a threshold distance from the subspace, then the display system may interpret this result to mean that the eye is within the display registration volume. If the eye is outside of the subspace or outside a threshold distance from the subject, then the display system may interpret this result to mean that the eye is outside of the display registration volume. If the display system determines that the eye is outside of the display registration volume, the display system may be configured to provide feedback to the user indicating that the display and the eye are not properly registered for output, and/or may be configured to take actions to mitigate display degradation caused by misregistration, as discussed herein.

Examples of a Housing Registration Volume and a System Registration Volume

Figure 19A:
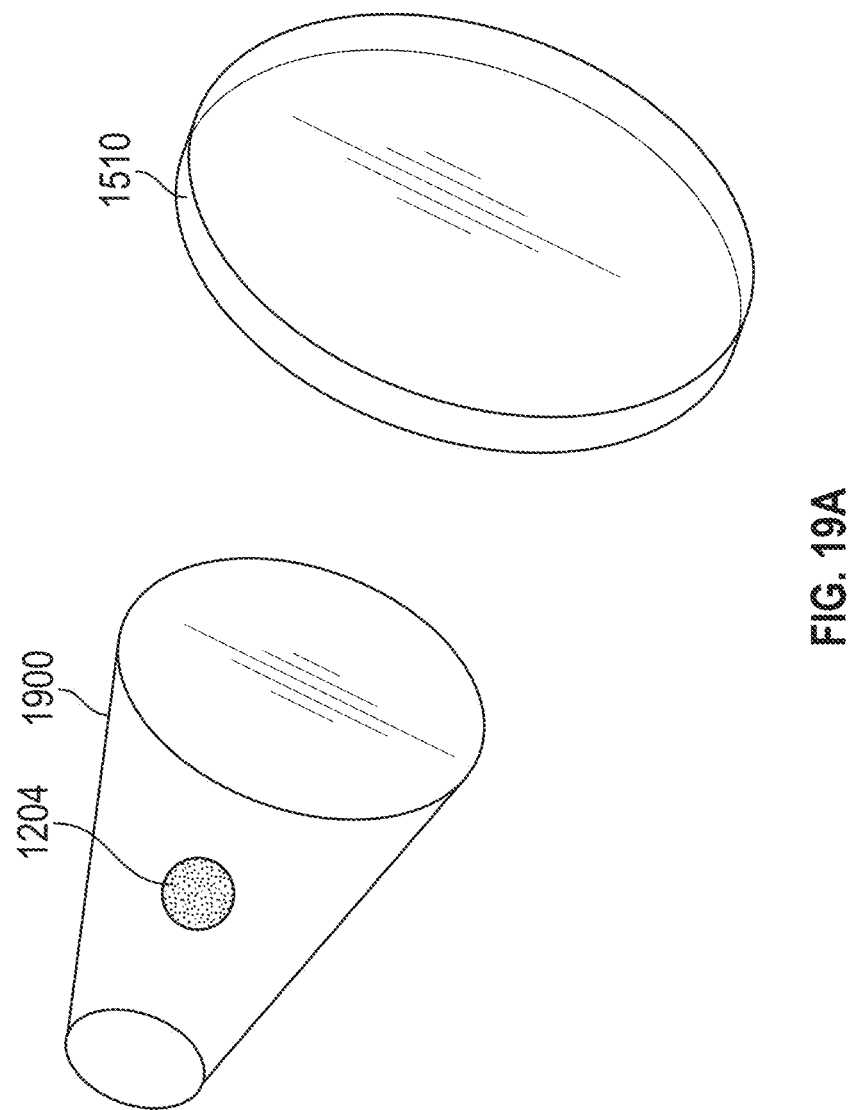
FIG. 19A illustrates a registration volume derived from a display housing of a head-mounted display system.

FIG. 19A illustrates an example housing registration volume 1900. Light from the ambient environment passes through the opening in the frame or housing of the display to reach the user. It will be appreciated that the frame or housing for the display may block some ambient light, from some angles, from reaching the eyes of the user. As a result, analogous to the display registration volume, and the housing registration volume 1900 may represent the spatial volume in which a user's eye is positioned so as to receive light from the external environment to make out the full field of view available through the housing or frame of the display. In some embodiments, a center of rotation of a user's eye is preferably located within the housing registration volume 1900 so that the eye receives light from the external environment at angles corresponding to the full available field of view. In some embodiments, when the center of rotation of the user's eye is located within the housing registration volume 1900, the user is able to see an acceptable portion of the world around them. Proper registration of the user's eye to the wearable system (e.g., by providing the center of rotation within the housing registration volume 1900) may help to reduce the likelihood that the user will be unable to see obstacles in their paths, may provide users with a left and right fields-of-view that overlap to facilitate binocular vision, and/or may provide a more comfortable visual experience for users.

As shown in FIG. 19A, the housing registration volume 1900 may be partially or wholly determined with reference to housing openings 1510, which may be openings (or lenses) in frame 230 of the wearable system as previously discussed in connection with FIG. 15A. The housing registration volume 1900 may, as an example, have a cone-like shape with a base defined by the shape and size of the housing openings 1510. Portions of the cone-like shape nearest the housing openings 1510 and portions farthest from the housing openings 1510 may be truncated (e.g., excluded from the housing registration volume 1900), which may help to move the user's eyes away from the display and housing openings 1510 such that the user's eyelashes do not impact the display when properly registered and may help reduce the impacts of noise in the location determination of the user's eyes, which might otherwise rapidly move into and out of registration in the small volume at the "top" of a cone-shaped registration volume. In some embodiments, the display system may be configured to determine whether the user's eyes (e.g., the centers of rotation of the eyes) are within the housing registration volume 1900 and to provide notifications of misregistration if the user's eyes are outside of the registration volume 1900.

Figure 19B:
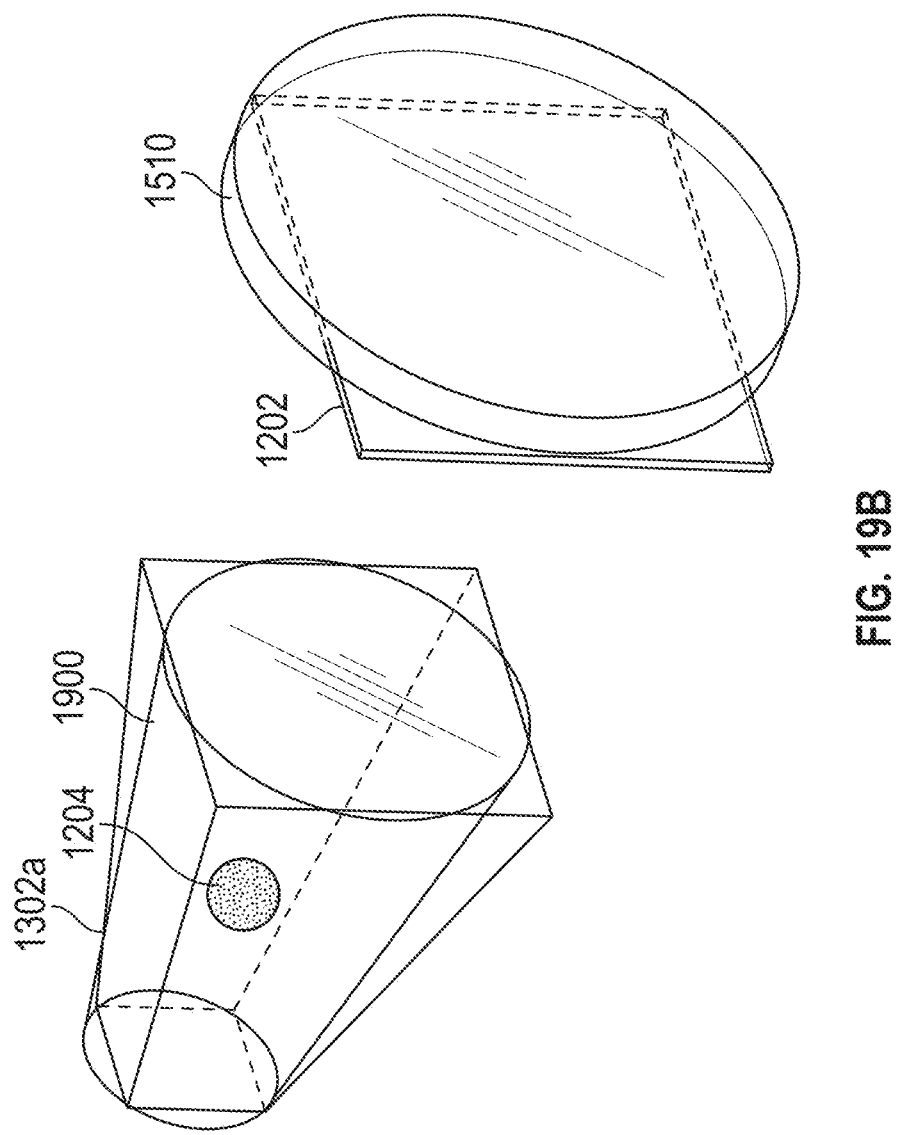
FIG. 19B illustrates superimposed registration volumes of a display housing and a display of a head-mounted display system.

FIG. 19B illustrates the display registration volume 1302a of FIG. 13A (associated with display surface 1202) superimposed on the housing registration volume 1900 of FIG. 1900 (associated with housing openings 1510). In at least some embodiments, it may be desirable for the center of rotation of a user's eye to be located within both the housing registration volume 1900 of FIG. 19A and the display registration volume such as the display registration volume 1302a of FIG. 13A (or any of the other display registration volumes discussed herein). When the user's eye is located within both the housing and display registration volumes, the user may be able to receive image information from the display device (with the full field of view provided by the display device) while also be able to view the full field of view of the external environment provided by the housing.

Figure 19C:
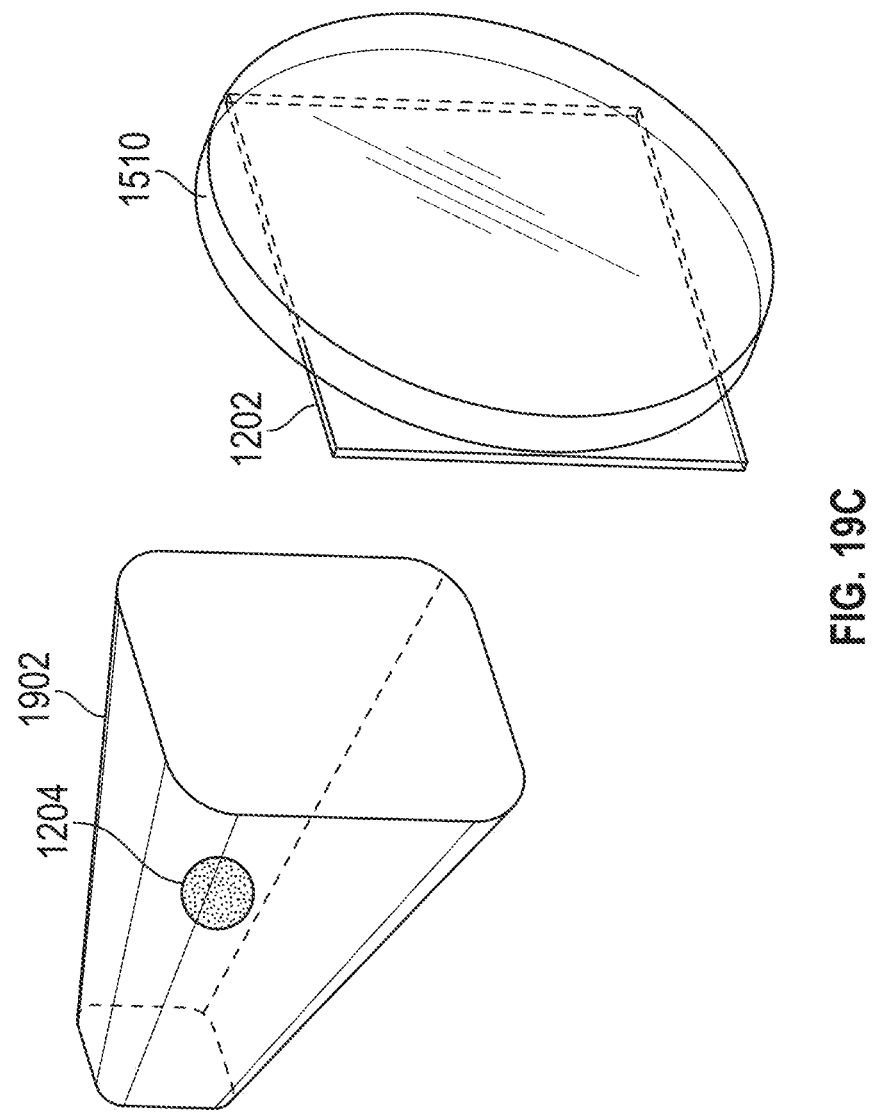
FIG. 19C illustrates an aggregate registration volume derived from the superimposed registration volumes of FIG. 19B.

FIG. 19C illustrates an example of a combined registration volume 1902, where every point in the combined registration volume 1902 lies within both the housing and display registration volumes (e.g., within displace registration volume 1302a and housing registration volume 1900). As shown in FIGS. 19B and 19C and in at least some embodiments, the display registration volume 1302a may be generally smaller than the housing registration volume 1900 (e.g., the housing registration volume 1900 may only be smaller at the corners of the display registration volume 1302a). In such embodiments, the combined registration volume 1902 may have a shape similar to a truncated pyramid having rounded corners, as illustrated in FIG. 19C. In some embodiments, the display system may be configured to determine whether the user's eyes (e.g., the centers of rotation of the eyes) are within the housing registration volume 1900, the display registration volume 1204, or both the housing registration volume 1900 and the display registration volume 1204. If the user's eyes are outside the particular volume being analyzed, the display system may be configured to provide notifications of misregistration if the user's eyes are outside of the registration volume being analyzed (e.g., the housing registration volume 1900, the display registration volume 1204, or both the housing registration volume 1900, the display registration volume 1204).

For example, in some embodiments, the combined overlapping registration volume defined by the housing registration volume 1900 and the display registration volume 1204 may be analyzed to determine whether the user's eyes are within this combined registration volume. In some embodiments, this may be understood to be a portion or subspace of the registration or viewing volume of the housing, which may also referred to as the outer housing. The display system may be configured to determine whether the user's eye is within this subspace (or an acceptable threshold distance outside of the subspace). If the display system determines that the position of the eye is more than the threshold distance outside of the subspace of the viewing volume of the outer housing of the display, and then it may provide feedback to the user indicating that the display and the eye are not properly registered.

Computer Vision to Detect Objects in Ambient Environment

As discussed above, the display system may be configured to detect objects in or properties of the environment surrounding the user. The detection may be accomplished using a variety of techniques, including various environmental sensors (e.g., cameras, audio sensors, temperature sensors, etc.), as discussed herein.

In some embodiments, objects present in the environment may be detected using computer vision techniques. For example, as disclosed herein, the display system's forward-facing camera may be configured to image the ambient environment and the display system may be configured to perform image analysis on the images to determine the presence of objects in the ambient environment. The display system may analyze the images acquired by the outward-facing imaging system to perform scene reconstruction, event detection, video tracking, object recognition, object pose estimation, learning, indexing, motion estimation, or image restoration, etc. As other examples, the display system may be configured to perform face and/or eye recognition to determine the presence and location of faces and/or human eyes in the user's field of view. One or more computer vision algorithms may be used to perform these tasks. Non-limiting examples of computer vision algorithms include: Scale-invariant feature transform (SIFT), speeded up robust features (SURF), oriented FAST and rotated BRIEF (ORB), binary robust invariant scalable keypoints (BRISK), fast retina keypoint (FREAK), Viola-Jones algorithm, Eigenfaces approach, Lucas-Kanade algorithm, Horn-Schunk algorithm, Mean-shift algorithm, visual simultaneous location and mapping (vSLAM) techniques, a sequential Bayesian estimator (e.g., Kalman filter, extended Kalman filter, etc.), bundle adjustment, Adaptive thresholding (and other thresholding techniques), Iterative Closest Point (ICP), Semi Global Matching (SGM), Semi Global Block Matching (SGBM), Feature Point Histograms, various machine learning algorithms (such as e.g., support vector machine, k-nearest neighbors algorithm, Naive Bayes, neural network (including convolutional or deep neural networks), or other supervised/unsupervised models, etc.), and so forth.

One or more of these computer vision techniques may also be used together with data acquired from other environmental sensors (such as, e.g., microphone) to detect and determine various properties of the objects detected by the sensors.

As discussed herein, the objects in the ambient environment may be detected based on one or more criteria. When the display system detects the presence or absence of the criteria in the ambient environment using a computer vision algorithm or using data received from one or more sensor assemblies (which may or may not be part of the display system), the display system may then signal the presence of the object.

Machine Learning

A variety of machine learning algorithms may be used to learn to identify the presence of objects in the ambient environment. Once trained, the machine learning algorithms may be stored by the display system. Some examples of machine learning algorithms may include supervised or non-supervised machine learning algorithms, including regression algorithms (such as, for example, Ordinary Least Squares Regression), instance-based algorithms (such as, for example, Learning Vector Quantization), decision tree algorithms (such as, for example, classification and regression trees), Bayesian algorithms (such as, for example, Naive Bayes), clustering algorithms (such as, for example, k-means clustering), association rule learning algorithms (such as, for example, a-priori algorithms), artificial neural network algorithms (such as, for example, Perceptron), deep learning algorithms (such as, for example, Deep Boltzmann Machine, or deep neural network), dimensionality reduction algorithms (such as, for example, Principal Component Analysis), ensemble algorithms (such as, for example, Stacked Generalization), and/or other machine learning algorithms. In some embodiments, individual models may be customized for individual data sets. For example, the wearable device may generate or store a base model. The base model may be used as a starting point to generate additional models specific to a data type (e.g., a particular user), a data set (e.g., a set of additional images obtained), conditional situations, or other variations. In some embodiments, the display system may be configured to utilize a plurality of techniques to generate models for analysis of the aggregated data. Other techniques may include using predefined thresholds or data values.

The criteria for detecting an object may include one or more threshold conditions. If the analysis of the data acquired by the environmental sensor indicates that a threshold condition is passed, the display system may provide a signal indicating the detection the presence of the object in the ambient environment. The threshold condition may involve a quantitative and/or qualitative measure. For example, the threshold condition may include a score or a percentage associated with the likelihood of the reflection and/or object being present in the environment. The display system may compare the score calculated from the environmental sensor's data with the threshold score. If the score is higher than the threshold level, the display system may detect the presence of the reflection and/or object. In some other embodiments, the display system may signal the presence of the object in the environment if the score is lower than the threshold. In some embodiments, the threshold condition may be determined based on the user's emotional state and/or the user's interactions with the ambient environment.

In some embodiments, the threshold conditions, the machine learning algorithms, or the computer vision algorithms may be specialized for a specific context. For example, in a diagnostic context, the computer vision algorithm may be specialized to detect certain responses to the stimulus. As another example, the display system may execute facial recognition algorithms and/or event tracing algorithms to sense the user's reaction to a stimulus, as discussed herein.

It will be appreciated that each of the processes, methods, and algorithms described herein and/or depicted in the figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some embodiments, particular operations and methods may be performed by circuitry that is specific to a given function.

Further, certain embodiments of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, a video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. In some embodiments, the non-transitory computer-readable medium may be part of one or more of the local processing and data module (140), the remote processing module (150), and remote data repository (160). The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the embodiments described herein is for illustrative purposes and should not be understood as requiring such separation in all embodiments. It should be understood that the described program components, methods, and systems may generally be integrated together in a single computer product or packaged into multiple computer products.

Other Considerations

Each of the processes, methods, and algorithms described herein and/or depicted in the attached figures may be embodied in, and fully or partially automated by, code modules executed by one or more physical computing systems, hardware computer processors, application-specific circuitry, and/or electronic hardware configured to execute specific and particular computer instructions. For example, computing systems may include general purpose computers (e.g., servers) programmed with specific computer instructions or special purpose computers, special purpose circuitry, and so forth. A code module may be compiled and linked into an executable program, installed in a dynamic link library, or may be written in an interpreted programming language. In some implementations, particular operations and methods may be performed by circuitry that is specific to a given function.

Further, certain implementations of the functionality of the present disclosure are sufficiently mathematically, computationally, or technically complex that application-specific hardware or one or more physical computing devices (utilizing appropriate specialized executable instructions) may be necessary to perform the functionality, for example, due to the volume or complexity of the calculations involved or to provide results substantially in real-time. For example, animations or video may include many frames, with each frame having millions of pixels, and specifically programmed computer hardware is necessary to process the video data to provide a desired image processing task or application in a commercially reasonable amount of time.

Code modules or any type of data may be stored on any type of non-transitory computer-readable medium, such as physical computer storage including hard drives, solid state memory, random access memory (RAM), read only memory (ROM), optical disc, volatile or non-volatile storage, combinations of the same and/or the like. The methods and modules (or data) may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The results of the disclosed processes or process steps may be stored, persistently or otherwise, in any type of non-transitory, tangible computer storage or may be communicated via a computer-readable transmission medium.

Any processes, blocks, states, steps, or functionalities in flow diagrams described herein and/or depicted in the attached figures should be understood as potentially representing code modules, segments, or portions of code which include one or more executable instructions for implementing specific functions (e.g., logical or arithmetical) or steps in the process. The various processes, blocks, states, steps, or functionalities may be combined, rearranged, added to, deleted from, modified, or otherwise changed from the illustrative examples provided herein. In some embodiments, additional or different computing systems or code modules may perform some or all of the functionalities described herein. The methods and processes described herein are also not limited to any particular sequence, and the blocks, steps, or states relating thereto may be performed in other sequences that are appropriate, for example, in serial, in parallel, or in some other manner. Tasks or events may be added to or removed from the disclosed example embodiments. Moreover, the separation of various system components in the implementations described herein is for illustrative purposes and should not be understood as requiring such separation in all implementations. It should be understood that the described program components, methods, and systems may generally be integrated together in a single computer product or packaged into multiple computer products. Many implementation variations are possible.

The processes, methods, and systems may be implemented in a network (or distributed) computing environment. Network environments include enterprise-wide computer networks, intranets, local area networks (LAN), wide area networks (WAN), personal area networks (PAN), cloud computing networks, crowd-sourced computing networks, the Internet, and the World Wide Web. The network may be a wired or a wireless network or any other type of communication network.

The systems and methods of the disclosure each have several innovative aspects, no single one of which is solely responsible or required for the desirable attributes disclosed herein. The various features and processes described above may be used independently of one another, or may be combined in various ways. All possible combinations and subcombinations are intended to fall within the scope of this disclosure. Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

What is claimed is:

1. A method for evaluating registration of virtual image content from a head-mounted display system by a user's eye, wherein the head-mounted display system comprises one or more eye-tracking cameras and at least one interchangeable fit piece, the method comprising:
   determining a position of the eye based on images of the eye obtained with the one or more eye-tracking cameras;
   determining whether the position of the eye is within a display registration volume of the head-mounted display system, wherein the display registration volume is an imaginary volume associated with proper fit of the head-mounted display system relative to the user's eye; and
   providing a notification based on a determination that the position of the eye is outside the display registration volume, where the notification indicates at least that the display and the eye are not properly registered.

2. The method of claim 1, wherein providing the notification comprises providing instructions causing the display system to boost a brightness of a plurality of pixels of the display relative to other pixels of the display, wherein the plurality of pixels with boosted brightness comprise pixels expected to undergo perceived dimming under improper registration.

3. The method of claim 1, wherein providing the notification comprises providing feedback to the user that the head-mounted display system is not properly adjusted to fit the user and providing a suggestion to the user to swap out a currently-installed interchangeable fit piece for another interchangeable fit piece.

4. The method of claim 1, wherein the head-mounted display system is configured to provide a first field of view when the position of the eye is inside the display registration volume and a second field of view when the position of the eye is outside the display registration volume, and further comprising changing a field of view of the head-mounted display system from the first field of view to the second field of view when the position of the eye is outside the display registration volume.

5. The method of claim 4, wherein providing the notification comprises displaying feedback to the user within the second field of view.

6. The method of claim 1, wherein the head-mounted display system comprises an eye-tracking camera, wherein determining the position of the eye comprises utilizing the eye-tracking camera to image the eye of the user.

7. The method of claim 6, wherein the position of the eye is a position of a center of rotation of the eye, and further comprising calculating the center of rotation of the eye based upon imaging of the eye by the eye-tracking camera.

8. The method of claim 6, further comprising continuously tracking the center of rotation of the eye while the head-mounted display system is in use and notifying the user when the center of rotation of the eye moves outside of the display registration volume.

9. The method of claim 1, wherein the head-mounted display system is configured to project light into the eye to display virtual image content in a field of view of the user, and further comprising displaying an indication that the display system is properly fitted, wherein displaying the indication comprises providing feedback to the user that the head-mounted display system is positioned such that the user's eye is within the display registration volume.

10. The method of claim 1, wherein, when the eye of the user is not within the display registration volume, dimming at least some pixels of the head-mounted display system, wherein the dimmed pixels correspond to portions of a possible field of view of the display system that are outside of a reduced field of view associated with the eye being outside the display registration volume.

11. A method for evaluating registration of virtual image content from a head-mounted display system by an eye of a user, wherein the head-mounted display system comprises a display disposed on a frame supported on a head of the user, the method comprising:
  determining a position of the eye based on images of the eye obtained with one or more eye-tracking cameras attached to the frame;
  determining whether the position of the eye is more than a first threshold distance outside of a viewing volume of the head-mounted display system; and
  in response to determining that the position of the eye is more than the first threshold distance outside of the viewing volume of the head-mounted display system, providing feedback to the user indicating that the display and the eye are not properly registered.

12. The method of claim 11, wherein determining whether the position of the eye is more than a first threshold distance outside of the viewing volume comprises:
  determining whether the position of the eye is less than a second threshold distance from the head-mounted display system; and
  in response to a determination that the position of the eye is less than the second threshold distance from the head-mounted display system, providing the feedback to the user indicating that the display and the eye are not properly registered.

13. The method of claim 11, further comprising obtaining a fit tolerance, wherein the fit tolerance comprises information associated with changes in registration of the virtual image content caused by variances of the user's eyes from a nominal position relative to the display system.

14. The method of claim 11, further comprising obtaining registration data, wherein obtaining the registration data comprises determining a spatial relationship between the display system and the user's eye.

15. The method of claim 11, further comprising:
  identifying an application running on the display system; and
  determining the first threshold distance based on the identified application.

16. A method for evaluating registration of virtual image content from a head-mounted display system by an eye of a user, wherein the head-mounted display system comprises a frame and a head-mounted display and at least one interchangeable fit piece attached to the frame, the method comprising:
  determining whether light projected by the head-mounted display is properly registered by the eye of the user, wherein the display is configured to project light into the user's eye to display the virtual image content with different amounts of wavefront divergence corresponding to different depth planes; and
  providing feedback to the user if the light projected by the head-mounted display is determined to not be properly registered, wherein the feedback comprises a suggestion to the user to swap out a currently-installed interchangeable fit piece for another interchangeable fit piece.

17. The method of claim 16, wherein the at least one interchangeable fit piece comprises an interchangeable nose bridge pad configured to adjust a fit between the frame and a nose bridge of the user.

18. The method of claim 17, further comprising determining that the user's eye is above a display registration volume of the head-mounted display system, wherein the display registration volume is an imaginary volume associated with proper fit of the head-mounted display system relative to the user's eye, and wherein providing the feedback to the user comprises prompting the user to install a larger nose bridge pad.

19. The method of claim 16, wherein the at least one interchangeable fit piece comprises an interchangeable forehead pad configured to adjust a fit of the frame and a forehead of the user.

20. The method of claim 16, wherein the at least one interchangeable fit piece comprises an interchangeable back pad configured to adjust a fit of the frame and a back of the head of the user.

* * * * *